(12) United States Patent
Kingsman et al.

(10) Patent No.: US 7,635,687 B2
(45) Date of Patent: *Dec. 22, 2009

(54) VECTOR SYSTEM

(75) Inventors: Alan John Kingsman, Oxford (GB); Christopher Robert Bebbington, San Mateo, CA (US); Miles William Carroll, Oxon (GB); Fiona Margaret Ellard, Oxford (GB); Susan Mary Kingsman, Oxford (GB); Kevin Alan Myers, Oxford (GB); Abigail Lamikanra, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 1213 days.

This patent is subject to a terminal disclaimer.

(21) Appl. No.: 10/334,235

(22) Filed: Dec. 30, 2002

(65) Prior Publication Data

US 2004/0131591 A1    Jul. 8, 2004

Related U.S. Application Data

(63) Continuation-in-part of application No. 10/060,585, filed on Jan. 29, 2002, now Pat. No. 7,276,488, and a continuation-in-part of application No. PCT/GB00/04317, filed on Nov. 13, 2000, and a continuation-in-part of application No. 09/445,375, filed on Dec. 6, 1999, now Pat. No. 6,852,703.

(30) Foreign Application Priority Data

| | | |
|---|---|---|
| Jun. 4, 1997 | (GB) | 9711579.4 |
| Jun. 20, 1997 | (GB) | 9713150.2 |
| Jul. 4, 1997 | (GB) | 9714230.1 |
| Nov. 18, 1999 | (GB) | PCT/GB99/03859 |
| Feb. 15, 2000 | (GB) | 0003527.9 |
| Mar. 2, 2000 | (GB) | 0005071.6 |

(51) Int. Cl.
*A61K 31/70* (2006.01)
(52) U.S. Cl. ........................................................ 514/44
(58) Field of Classification Search .................... 514/44
See application file for complete search history.

(56) References Cited

U.S. PATENT DOCUMENTS

| | | | | |
|---|---|---|---|---|
| 6,143,520 A | * | 11/2000 | Marasco et al. | 435/69.1 |
| 6,277,633 B1 | * | 8/2001 | Olsen | 435/320.1 |
| 6,277,972 B1 | * | 8/2001 | Afar et al. | 536/23.1 |
| 6,514,498 B1 | * | 2/2003 | Antonsson et al. | 424/178.1 |
| 6,852,703 B1 | * | 2/2005 | Kingsman et al. | 514/44 |
| 7,074,909 B2 | * | 7/2006 | Kingsman et al. | 536/23.1 |

OTHER PUBLICATIONS

Greco et al. (Frontiers in Biosci. 2002; 7:d1516-1524).*
Anderson (Nature, vol. 392 (suppl), 1998; pp. 25-30).*

* cited by examiner

*Primary Examiner*—J. E Angell
(74) *Attorney, Agent, or Firm*—Marshall, Gerstein & Borun LLP

(57) ABSTRACT

The present invention provides a vector system comprising a nucleotide sequence coding for an antibody. In particular, the present invention relates to the use of such a vector system in a subject, where the nucleotide sequence is expressed in vivo to produce said antibody.

7 Claims, 26 Drawing Sheets

FIGURE 1A-1

```
  1   GAGGTCCAGC TTCAGCAGTC TGGACCTGAC CTGGTGAAGC CTGGGGCTTC
        E  V  Q  L  Q  Q  S  G  P  D  L  V  K  P  G  A  S

51   AGTGAAGATA TCCTGCAAGG CTTCTGGTTA CTCATTCACT GGCTACTACA
        V  K  I  S  C  K  A  S  G  Y  S  F  T  G  Y  Y

101   TGCACTGGGT GAAGCAGAGC CATGGAAAGA GCCTTGAGTG GATTGGACGT
        M  H  W  V  K  Q  S  H  G  K  S  L  E  W  I  G  R

151   ATTAATCCTA ACAATGGTGT TACTCTCTAC AACCAGAAAT TCAAGGACAA
        I  N  P  N  N  G  V  T  L  Y  N  Q  K  F  K  D  K

201   GGCCATATTA ACTGTAGACA AGTCATCCAC CACAGCCTAC ATGGAGCTCC
        A  I  L  T  V  D  K  S  S  T  T  A  Y  M  E  L

251   GCAGCCTGAC ATCTGAGGAC TCTGCGGTCT ATTACTGTGC AAGATCTACT
        R  S  L  T  S  E  D  S  A  V  Y  Y  C  A  R  S  T

301   ATGATTACGA ACTATGTTAT GGACTACTGG GGTCAAGTAA CCTCAGTCAC
        M  I  T  N  Y  V  M  D  Y  W  G  Q  V  T  S  V  T

351   CGTCTCCTCA GGTGGTGGTG GGAGCGGTGG TGGCGGCACT GGCGGCGGCG
             V  S  S  G  G  G  G  S  G  G  G  T  G  G  G

401   GATCTAGTAT TGTGATGACC CAGACTCCCA CATTCCTGCT TGTTTCAGCA
        G  S  S  I  V  M  T  Q  T  P  T  F  L  L  V  S  A

451   GGAGACAGGG TTACCATAAC CTGCAAGGCC AGTCAGAGTG TGAGTAATGA
        G  D  R  V  T  I  T  C  K  A  S  Q  S  V  S  N  D

501   TGTAGDTTGG   TACCAACAGA AGCCAGGGCA GTCTCCTACA CTGCTCATAT
        V  A  W     Y  Q  Q  K  P  G  Q  S  P  T  L  L  I
```

FIGURE 1A-2

```
551   CCTATACATC CAGTCGCTAC GCTGGAGTCC CTGATCGCTT CATTGGCAGT
       S  Y  T  S   S  R  Y   A  G  V    P  D  R  F   I  G  S

601   GGATATGGGA CGGATTTCAC TTTCACCATC AGCACTTTGC AGGCTGAAGA
          G  Y  G   T  D  F  T   F  T  I    S  T  L   Q  A  E  D

651   CCTGGCAGTT TATTTCTGTC AGCAAGATTA TAATTCTCCT CCGACGTTCG
            L  A  V   Y  F  C   Q  Q  D  Y   N  S  P   P  T  F

701   GTGGAGGCAC CAAGCTGGAA ATCAAACGG  (SEQ ID NO:1)
         G  G  G  T   K  L  E   I  K  R  (SEQ ID NO:37)
```

FIGURE 1B-1

```
1    AAGCTTCCAC CATGGGATGG AGCTGTATCA TCCTCTTCTT GGTAGCAACA
          A  S  T  M  G  W  S  C  I  I  L  F  L  V  A  T

51   GCTACAGGTG TCCACTCCGA GGTCCAGCTT CAGCAGTCTG GACCTGACCT
       A  T  G  V  H  S  E  V  Q  L  Q  Q  S  G  P  D  L

101  GGTGAAGCCT  GGGGCTTCAG TGAAGATATC CTGCAAGGCT TCTGGTTACT
        V  K  P  G  A  S  V  K  I  S  C  K  A  S  G  Y

151  CATTCACTGG  CTACTACATG CACTGGGTGA AGCAGAGCCA TGGAAAGAGC
       S  F  T  G  Y  Y  M  H  W  V  K  Q  S  H  G  K  S

201  CTTGAGTGGA TTGGACGTAT TAATCCTAAC AATGGTGTTA CTCTCTACAA
        L  E  W  I  G  R  I  N  P  N  N  G  V  T  L  Y  N

251  CCAGAAATTC AAGGACAAGG CCATATTAAC TGTAGACAAG TCATCCACCA
        Q  K  F  K  D  K  A  I  L  T  V  D  K  S  S  T

301  CAGCCTACAT GGAGCTCCGC AGCCTGACAT CTGAGGACTC TGCGGTCTAT
        T  A  Y  M  E  L  R  S  L  T  S  E  D  S  A  V  Y

351  TACTGTGCAA GATCTACTAT GATTACGAAC TATGTTATGG ACTACTGGGG
        Y  C  A  R  S  T  M  I  T  N  Y  V  M  D  Y  W  G

401  TCAAGTAACC TCAGTCACCG TCTCCTCAGG TGGTGGTGGG AGCGGTGGTG
        Q  V  T  S  V  T  V  S  S  G  G  G  S  G  G
```

FIGURE 1B-2

```
451  GCGGCACTGG CGGCGGCGGA TCTAGTATTG TGATGACCCA GACTCCCACA
      G  G  T  G  G  G  S  S  I  V  M  T  Q  T  P  T

501  TTCCTGCTTG TTTCAGCAGG AGACAGGGTT ACCATAACCT GCAAGGCCAG
      F  L  L  V  S  A  G  D  R  V  T  I  T  C  K  A  S

551  TCAGAGTGTG AGTAATGATG TAGCTTGGTA CCAACAGAAG CCAGGGCAGT
       Q  S  V  S  N  D  V  A  W  Y  Q  Q  K  P  G  Q

601  CTCCTACACT GCTCATATCC TATACATCCA GTCGCTACGC TGGAGTCCCT
      S  P  T  L  L  I  S  Y  T  S  S  R  Y  A  G  V  P

651  GATCGCTTCA TTGGCAGTGG ATATGGGACG GATTTCACTT TCACCATCAG
      D  R  F  I  G  S  G  Y  G  T  D  F  T  F  T  I  S

701  CACTTTGCAG GCTGAAGACC TGGCAGTTTA TTTCTGTCAG CAAGATTATA
       T  L  Q  A  E  D  L  A  V  Y  F  C  Q  Q  D  Y

751  ATTCTCCTCC GACGTTCGGT GGAGGCACCA AGCTGGAAAT CAAACGGGCC
      N  S  P  P  T  F  G  G  G  T  K  L  E  I  K  R  A

801  TCCACCAAGG GCCCATCGGT CTTCCCCCTG GCACCCTCCT CCAAGAGCAC
       S  T  K  G  P  S  V  F  P  L  A  P  S  S  K  S  T

851  CTCTGGGGGC ACAGCGGCCC TGGGCTGCCT GGTCAAGGAC TACTTCCCCG
       S  G  G  T  A  A  L  G  C  L  V  K  D  Y  F  P
```

FIGURE 1B-3

```
901   AACCGGTGAC GGTGTCGTGG AACTCAGGCG CCCTGACCAG CGGCGTGCAC
       E   P   V   T   V   S   W   N   S   G   A   L   T   S   G   V   H

951   ACCTTCCCGG CTGTCCTACA GTCCTCAGGA CTCTACTCCC TCAGCAGCGT
       T   F   P   A   V   L   Q   S   S   G   L   Y   S   L   S   S   V

1001  GGTGACCGTG CCCTCCAGCA GCTTGGGCAC CCAGACCTAC ATCTGCAACG
       V   T   V   P   S   S   S   L   G   T   Q   T   Y   I   C   N

1051  TGAATCACAA GCCCAGCAAC ACCAAGGTGG ACAAGAAAGT TGAGCCCAAA
       V   N   H   K   P   S   N   T   K   V   D   K   K   V   E   P   K

1101  TCTTGTGACA AAACTCACAC ATGCCCACCG TGCCCAGCAC CTGAACTCCT
       S   C   D   K   T   H   T   C   P   P   C   P   A   P   E   L   L

1151  GGGGGGACCG TCAGTCTTCC TCTTCCCCCC AAAACCCAAG GACACCCTCA
       G   G   P   S   V   F   L   F   P   P   K   P   K   D   T   L

1201  TGATCTCCCG GACCCCTGAG GTCACATGCG TGGTGGTGGA CGTGAGCCAC
       M   I   S   R   T   P   E   V   T   C   V   V   V   D   V   S   H

1251  GAAGACCCTG AGGTCAAGTT CAACTGGTAC GTGGACGGCG TGGAGGTGCA
       E   D   P   E   V   K   F   N   W   Y   V   D   G   V   E   V   H

1301  TAATGCCAAG ACAAAGCCGC GGGAGGAGCA GTACAACAGC ACGTACCGTG
       N   A   K   T   K   P   R   E   E   Q   Y   N   S   T   Y   R
```

FIGURE 1B-4

```
1351 TGGTCAGCGT CCTCACCGTC CTGCACCAGG ACTGGCTGAA TGGCAAGGAG
      V  V  S  V   L  T  V   L  H  Q   D  W  L   N  G  K  E

1401 TACAAGTGCA AGGTCTCCAA CAAAGCCCTC CCAGCCCCCA TCGAGAAAAC
      Y  K  C   K  V  S  N   K  A  L   P  A  P   I  E  K  T

1451 CATCTCCAAA GCCAAAGGGC AGCCCCGAGA ACCACAGGTG TACACCCTGC
      I  S  K   A  K  G   Q  P  R  E   P  Q  V   Y  T  L

1501 CCCCATCCCG GGATGAGCTG ACCAAGAACC AGGTCAGCCT GACCTGCCTG
      P  P  S  R   D  E  L   T  K  N   Q  V  S  L   T  C  L

1551 GTCAAAGGCT TCTATCCCAG CGACATCGCC GTGGAGTGGG AGAGCAATGG
      V  K  G   F  Y  P  S   D  I  A   V  E  W   E  S  N  G

1601 GCAGCCGGAG AACAACTACA AGACCACGCC TCCCGTGCTG GACTCCGACG
      Q  P  E   N  N  Y   K  T  T  P   P  V  L   D  S  D

1651 GCTCCTTCTT CCTCTACAGC AAGCTCACCG TGGACAAGAG CAGGTGGCAG
      G  S  F  F   L  Y  S   K  L  T   V  D  K  S   R  W  Q

1701 CAGGGGAACG  TCTTCTCATG CTCCGTGATG CATGAGGCTC TGCACAACCA
      Q  G  N   V  F  S  C   S  V  M   H  E  A   L  H  N  H

1751 CTACACGCAG  AAGAGCCTCT CCCTGTCTCC GGGTAAATGA GTGCGACGGC
      Y  T  Q   K  S  L   S  L  S  P   G  K  -    V  R  R

1801 CAAGCTT (SEQ ID NO:2)
      P  S    (SEQ ID NO:38)
```

FIGURE 2A

| | |
|---|---|
| ATGGGCCACA CACGGAGGCA GGGAACATCA CCATCCAAGT GTCCATACCT | 50 |
|   M  G  H   T   R   R   Q   G   T   S   P   S   K   C   P   Y   L | |
| CAATTTCTTT CAGCTCTTGG TGCTGGCTGG TCTTTCTCAC TTCTGTTCAG | 100 |
|   N  F  F   Q   L   L   V   L   A   G   L   S   H   F   C   S | |
| GTGTTATCCA CGTGACCAAG GAAGTGAAAG AAGTGGCAAC GCTGTCCTGT | 150 |
|   G  V  I   H   V   T   K   E   V   K   E   V   A   T   L   S   C | |
| GGTCACAATG TTTCTGTTGA AGAGCTGGCA CAAACTCGCA TCTACTGGCA | 200 |
|   G  H  N   V   S   V   E   E   L   A   Q   T   R   I   Y   W   Q | |
| AAAGGAGAAG AAAATGGTGC TGACTATGAT GTCTGGGGAC ATGAATATAT | 250 |
|   K  E  K   K   M   V   L   T   M   M   S   G   D   M   N   I | |
| GGCCCGAGTA CAAGAACCGG ACCATCTTTG ATATCACTAA TAACCTCTCC | 300 |
|   W  P  E   Y   K   N   R   T   I   F   D   I   T   N   N   L   S | |
| ATTGTGATCC TGGCTCTGCG CCCATCTGAC GAGGGCACAT ACGAGTGTGT | 350 |
|   I  V  I   L   A   L   R   P   S   D   E   G   T   Y   E   C   V | |
| TGTTCTGAAG TATGAAAAAG ACGCTTTCAA GCGGGAACAC CTGGCTGAAG | 400 |
|   V  L  K   Y   E   K   D   A   F   K   R   E   H   L   A   E | |
| TGACGTTATC AGTCAAAGCT GACTTCCCTA CACCTAGTAT ATCTGACTTT | 450 |
|   V  T  L   S   V   K   A   D   F   P   T   P   S   I   S   D   F | |
| GAAATTCCAA CTTCTAATAT TAGAAGGATA ATTTGCTCAA CCTCTGGAGG | 500 |
|   E  I  P   T   S   N   I   R   R   I   I   C   S   T   S   G   G | |

FIGURE 2B

| | |
|---|---|
| TTTTCCAGAG CCTCACCTCT CCTGGTTGGA AAATGGAGAA GAATTAAATG | 550 |
|   F   P   E    P  H  L    S  W  L    E    N    G    E    E    L    N | |
| CCATCAACAC AACAGTTTCC CAAGATCCTG AAACTGAGCT CTATGCTGTT | 600 |
| A  I  N    T    V    S    Q    D    P    E    T    E    L    Y    A    V | |
| AGCAGCAAAC TGGATTTCAA TATGACAACC AACCACAGCT TCATGTGTCT | 650 |
| S  S  K    L    D    F    N    M    T    T    N    H    S    F    M    C    L | |
| CATCAAGTAT GGACATTTAA GAGTGAATCA GACCTTCAAC TGGAATACAA | 700 |
| I  K  Y    G  H  L    R    V    N    Q    T    F    N    W    N    T | |
| CCAAGCAAGA GCATTTTCCT GATGGAGGCG GGGGATCCGA GGTCCAGCTT | 750 |
| T  K  Q  E    H    F    P    D  G    G    G    S    E    V    Q    L | |
| CAGCAGTCTG GACCTGACCT GGTGAAGCCT GGGGCTTCAG TGAAGATATC | 800 |
| Q  Q  S    G    P    D    L    V    K    P    G    A    S    V    K    I    S | |
| CTGCAAGGCT TCTGGTTACT CATTCACTGG CTACTACATG CACTGGGTGA | 850 |
| C  K  A    S    G    Y    S    F    T    G    Y    Y    M    H    W    V | |
| AGCAGAGCCA TGGAAAGAGC CTTGAGTGGA TTGGACGTAT TAATCCTAAC | 900 |
| K  Q  S    H    G    K    S    L    E    W    I    G    R    I    N    P    N | |
| AATGGTGTTA CTCTCTACAA CCAGAAATTC AAGGACAAGG CCATATTAAC | 950 |
| N  G  V    T    L    Y    N    Q    K    F    K    D    K    A    I    L    T | |
| TGTAGACAAG TCATCCACCA CAGCCTACAT GGAGCTCCGC AGCCTGACAT | 1000 |
| V  D  K    S    S    T    T    A    Y    M    E    L    R    S    L    T | |

FIGURE 2C

```
CTGAGGACTC TGCGGTCTAT TACTGTGCAA GATCTACTAT GATTACGAAC         1050
 S  E  D  S  A  V  Y  Y  C  A  R  S  T  M  I  T  N

TATGTTATGG ACTACTGGGG TCAAGTAACC TCAGTCACCG TCTCCTCAGG         1100
 Y  V  M  D  Y  W  G  Q  V  T  S  V  T  V  S  S  G

TGGTGGTGGG AGCGGTGGTG GCGGCACTGG CGGCGGCGGA TCTAGTATTG         1150
 G  G  G  S  G  G  G  G  T  G  G  G  G  S  S  I

TGATGACCCA GACTCCCACA TTCCTGCTTG TTTCAGCAGG AGACAGGGTT         1200
 V  M  T  Q  T  P  T  F  L  L  V  S  A  G  D  R  V

ACCATAACCT GCAAGGCCAG TCAGAGTGTG AGTAATGATG TAGCTTGGTA         1250
 T  I  T  C  K  A  S  Q  S  V  S  N  D  V  A  W  Y

CCAACAGAAG CCAGGGCAGT CTCCTACACT GCTCATATCC TATACATCCA         1300
 Q  Q  K  P  G  Q  S  P  T  L  L  I  S  Y  T  S

GTCGCTACGC TGGAGTCCCT GATCGCTTCA TTGGCAGTGG ATATGGGACG         1350
 S  R  Y  A  G  V  P  D  R  F  I  G  S  G  Y  G  T

GATTTCACTT TCACCATCAG CACTTTGCAG GCTGAAGACC TGGCAGTTTA         1400
 D  F  T  F  T  I  S  T  L  Q  A  E  D  L  A  V  Y

TTTCTGTCAG CAAGATTATA ATTCTCCTCC GACGTTCGGT GGAGGCACCA         1450
 F  C  Q  Q  D  Y  N  S  P  P  T  F  G  G  T

AGCTGGAAAT CAAATAA  (SEQ ID NO:3)
 K  L  E  I  K     (SEQ ID NO:39)
```

FIGURE 4A

```
1    ATGGGACTGA GTAACATTCT CTTTGTGATG GCCTTCCTGC TCTCTGGTGC
      M  G  L   S  N  I  L   F  V  M   A  F  L  L   S  G  A

51   TGCTCCTCTG AAGATTCAAG CTTATTTCAA TGAGACTGCA GACCTGCCAT
       A  P  L   K  I  Q   A  Y  F  N   E  T  A   D  L  P

101  GCCAATTTGC AAACTCTCAA AACCAAAGCC TGAGTGAGCT AGTAGTATTT
      C  Q  F   A  N  S   Q  N  Q  S   L  S  E  L   V  V  F

151  TGGCAGGACC AGGAAAACTT GGTTCTGAAT GAGGTATACT TAGGCAAAGA
      W  Q  D   Q  E  N  L   V  L  N   E  V  Y   L  G  K  E

201  GAAATTTGAC AGTGTTCATT CCAAGTATAT GGGCCGCACA AGTTTTGATT
       K  F  D   S  V  H   S  K  Y  M   G  R  T   S  F  D

251  CGGACAGTTG GACCCTGAGA CTTCACAATC TTCAGATCAA GGACAAGGGC
       S  D  S  W   T  L  R   L  H  N   L  Q  I  K   D  K  G

301  TTGTATCAAT  GTATCATCCA TCACAAAAAG CCCACAGGAA TGATTCGCAT
       L  Y  Q    C  I  I   H  H  K  K   P  T  G   M  I  R  I

351  CCACCAGATG  AATTCTGAAC TGTCAGTGCT TGCTAACTTC AGTCAACCTG
       H  Q  M   N  S  E    L  S  V  L   A  N  F  S   Q  P

401  AAATAGTACC AATTTCTAAT ATAACAGAAA ATGTGTACAT AAATTTGACC
       E  I  V  P   I  S  N   I  T  E   N  V  Y  I   N  L  T

451  TGCTCATCTA TACACGGTTA CCCAGAACCT AAGAAGATGA GTGTTTTGCT
       C  S  S   I  H  G  Y   P  E  P   K  K  M   S  V  L  L
```

FIGURE 4B

```
501 AAGAACCAAG AATTCAACTA TCGAGTATGA TGGTATTATG CAGAAATCTC
      R   T  K    N  S  T    I  E  Y  D    G  I  M  Q    K  S

551 AAGATAATGT CACAGAACTG TACGACGTTT CCATCAGCTT GTCTGTTTCA
      Q  D  N  V    T  E  L    Y  D  V  F    P  S  A  C    L  F  Q

601 TTCCCTGATG TTACGAGCAA TATGACCATC TTCTGTATTC TGGAAACTGA
       F  P  D    V  T  S    N  M  T  I    F  C  I    L  E  T  D

651 CAAGACGCGG    CTTTTATCTT CACCTTTCTC TATAGAGCTT GAGGACCCTC
       K  T  R     L  L  S    P  F  S    I  E    L  E  D  P

701 AGCCTCCCCC AGACCACATT CCTGGAGGCG GGGGATCC    (SEQ ID NO:4)
       Q  P  P    P  D  H  I    P  G  G    G  G  S    (SEQ ID NO:40)
```

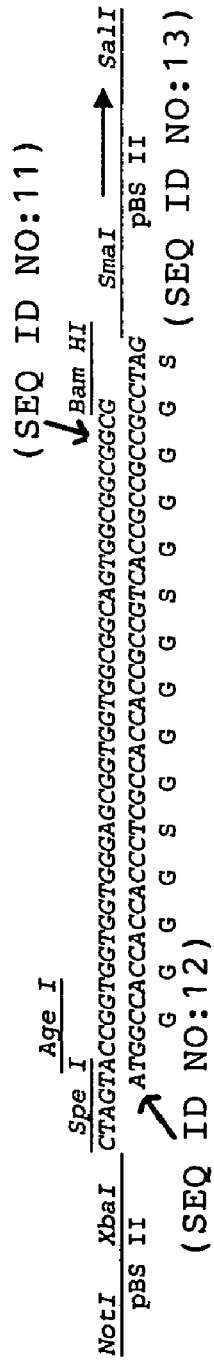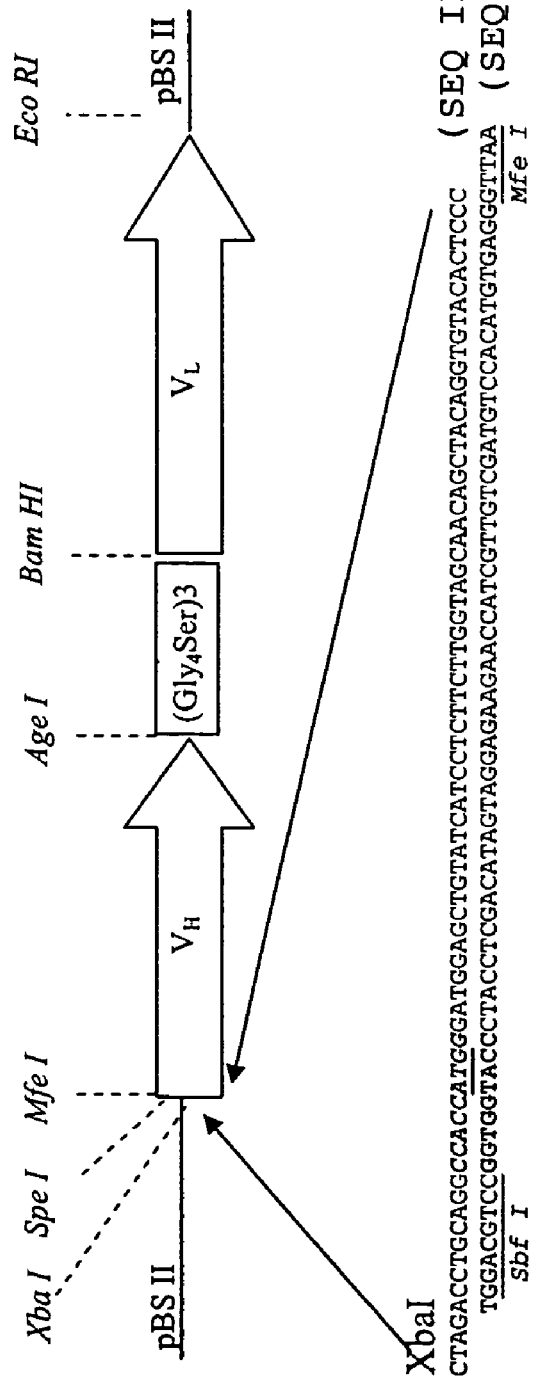

Figure 11
anti B7.1
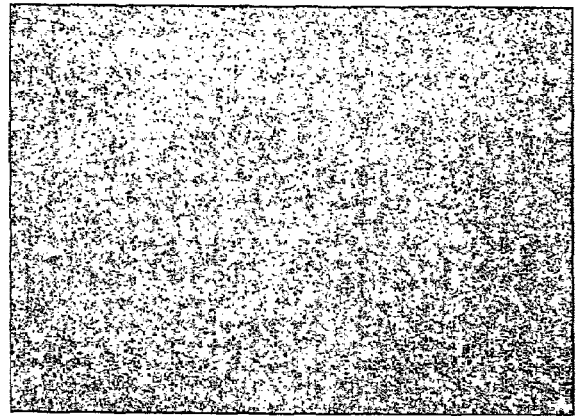
anti c-myc
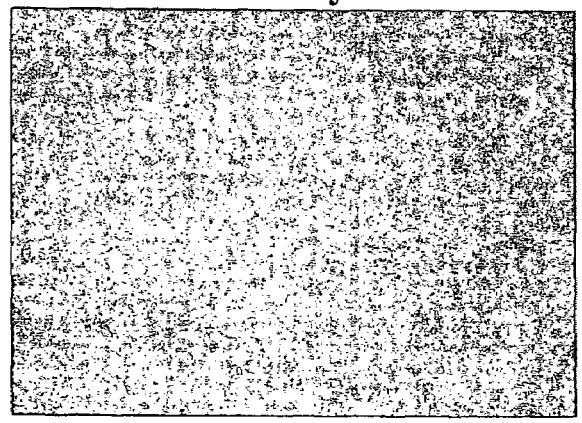
X-gal stain
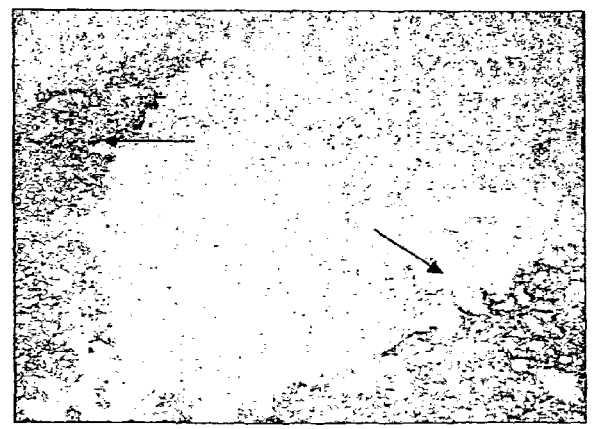

Figure 12
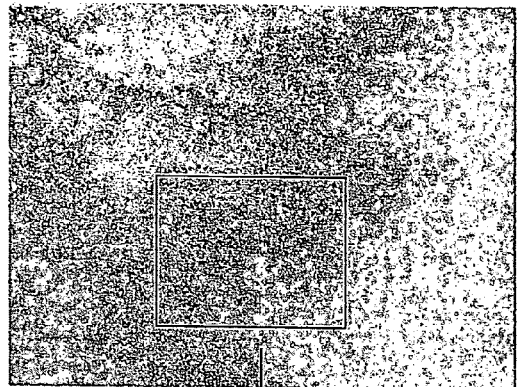
anti B7.1
X 100 mag
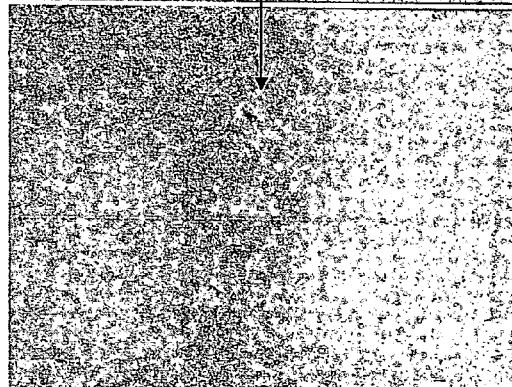
X 200 mag
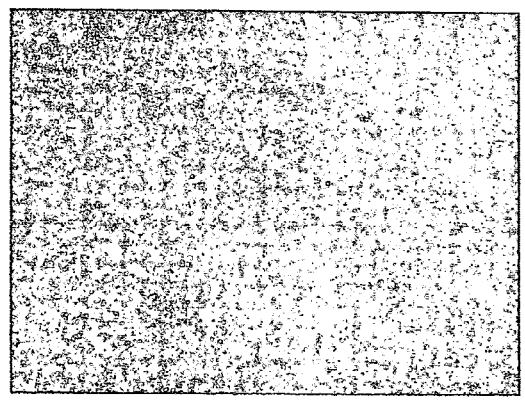
secondary alone
anti c-myc
X 100 mag
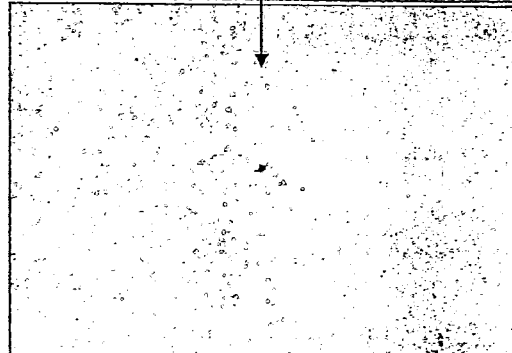
X 200 mag
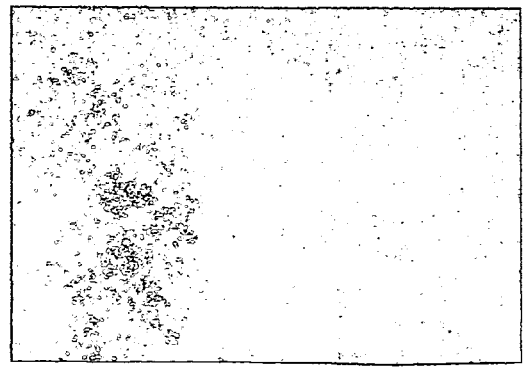
secondary alone

Figure 13A

```
   1  agatcttgaa taataaaatg tgtgtttgtc cgaaatacgc
  41  gttttgagat ttctgtcgcc gactaaattc atgtcgcgcg
  81  atagtggtgt ttatcgccga tagagatggc gatattggaa
 121  aaattgatat ttgaaaatat ggcatattga aaatgtcgcc
 161  gatgtgagtt tctgtgtaac tgatatcgcc atttttccaa
 201  aagtgatttt tgggcatacg cgatatctgg cgatagcgct
 241  tatatcgttt acggggatg gcgatagacg actttggtga
 281  cttggcgat tctgtgtgtc gcaaatatcg cagtttcgat
 321  ataggtgaca gacgatatga ggctatatcg ccgatagagg
 361  cgacatcaag ctggcacatg gccaatgcat atcgatctat
 401  acattgaatc aatattggcc attagccata ttattcattg
 441  gttatatagc ataaatcaat attggctatt ggccattgca
 481  tacgttgtat ccatatcgta atatgtacat ttatattggc
 521  tcatgtccaa cattaccgcc atgttgacat tgattattga
 561  ctagttatta atagtaatca attacggggt cattagttca
 601  tagcccatat atggagttcc gcgttacata acttacggta
 641  aatggcccgc ctggctgacc gcccaacgac ccccgcccat
 681  tgacgtcaat aatgacgtat gttcccatag taacgccaat
 721  agggactttc cattgacgtc aatgggtgga gtatttacgg
 761  taaactgccc acttggcagt acatcaagtg tatcatatgc
 801  caagtccgcc ccctattgac gtcaatgacg gtaaatggcc
 841  cgcctggcat tatgcccagt acatgaccctt acgggacttt
 881  cctacttggc agtacatcta cgtattagtc atcgctatta
 921  ccatggtgat gcggttttgg cagtacacca atgggcgtgg
 961  atagcggttt gactcacggg gatttccaag tctccacccc
1001  attgacgtca atgggagttt gttttggcac caaaatcaac
1041  gggactttcc aaaatgtcgt aacaactgcg atcgcccgcc
1081  ccgttgacgc aaatgggcgg taggcgtgta cggtgggagg
1121  tctatataag cagagctcgt ttagtgaacc gggcactcag
1161  attctgcggt ctgagtccct tctctgctgg gctgaaaagg
1201  cctttgtaat aaatataatt ctctactcag tccctgtctc
1241  tagtttgtct gttcgagatc ctacagttgg cgcccgaaca
1281  gggacctgag aggggcgcag accctacctg ttgaacctgg
1321  ctgatcgtag gatccccggg acagcagagg agaacttaca
1361  gaagtcttct ggaggtgttc ctggccagaa cacaggagga
1401  caggtaagat tgggagaccc tttgacattg gagcaaggcg
1441  ctcaagaagt tagagaaggt gacggtacaa gggtctcaga
1481  aattaactac tggtaactgt aattgggcgc taagtctagt
1521  agacttattt catgatacca actttgtaaa agaaaaggac
1561  tggcagctga gggatgtcat tccattgctg gaagatgtaa
1601  ctcagacgct gtcaggacaa gaaagagagg cctttgaaag
1641  aacatggtgg gcaatttctg ctgtaaagat gggcctccag
1681  attaataatg tagtagatgg aaaggcatca ttccagctcc
1721  taagagcgaa atatgaaaag aagactgcta ataaaagca
1761  gtctgagccc tctgaagaat atctctagag tcgacgctct
1801  cattacttgt aacaaaggga gggaaagtat gggaggacag
1841  acaccatggg aagtatttat cactaatcaa gcacaagtaa
1881  tacatgagaa acttttacta cagcaagcac aatcctccaa
1921  aaaatttgt ttttacaaaa tccctggtga acatggtcga
1961  ctctagaact agtggatccc ccgggctgca ggagtgggga
2001  ggcacgatgg ccgctttggt cgaggcggat ccggccatta
2041  gccatattat tcattggtta tatagcataa atcaatattg
2081  gctattggcc attgcatacg ttgtatccat atcataatat
2121  gtacatttat attggctcat gtccaacatt accgccatgt
2161  tgacattgat tattgactag ttattaatag taatcaatta
```

FIGURE 13B

```
2201  cggggtcatt  agttcatagc  ccatatatgg  agttccgcgt
2241  tacataactt  acggtaaatg  gcccgcctgg  ctgaccgccc
2281  aacgacccc   gcccattgac  gtcaataatg  acgtatgttc
2321  ccatagtaac  gccaataggg  actttccatt  gacgtcaatg
2361  ggtggagtat  ttacggtaaa  ctgcccactt  ggcagtacat
2401  caagtgtatc  atatgccaag  tacgccccct  attgacgtca
2441  atgacggtaa  atggcccgcc  tggcattatg  cccagtacat
2481  gaccttatgg  gactttccta  cttggcagta  catctacgta
2521  ttagtcatcg  ctattaccat  ggtgatgcgg  ttttggcagt
2561  acatcaatgg  gcgtggatag  cggtttgact  cacggggatt
2601  tccaagtctc  cacccattg   acgtcaatgg  gagtttgttt
2641  tggcaccaaa  atcaacggga  ctttccaaaa  tgtcgtaaca
2681  actccgcccc  attgacgcaa  atgggcggta  ggcatgtacg
2721  gtgggaggtc  tatataagca  gagctcgttt  agtgaaccgt
2761  cagatcgcct  ggagacgcca  tccacgctgt  tttgacctcc
2801  atagaagaca  ccgggaccga  tccagcctcc  gcggccccaa
2841  gcttgatatc gaattccacc  atggcttgca  attgtcagtt
2881  gatgcaggat  acaccactcc  tcaagtttcc  atgtccaagg
2921  ctcattcttc  tctttgtgct  gctgattcgt  ctttcacaag
2961  tgtcttcaga  tgttgatgaa  caactgtcca  agtcagtgaa
3001  agataaggta  ttgctgcctt  gccgttacaa  ctctccgcat
3041  gaagatgagt  ctgaagaccg  aatctactgg  caaaaacatg
3081  acaaagtggt  gctgtctgtc  attgctggga  aactaaaagt
3121  gtggcccgag  tataagaacc  ggactttata  tgacaacact
3161  acctactctc  ttatcatcct  gggcctggtc  ctttcagacc
3201  ggggcacata  cagctgtgtc  gttcaaaaga  aggaaagagg
3241  aacgtatgaa  gttaaacact  tggctttagt  aaagttgtcc
3281  atcaaagctg  acttctctac  ccccaacata  actgagtctg
3321  gaaacccatc  tgcagacact  aaaaggatta  cctgctttgc
3361  ttccgggggt  ttcccaaagc  ctcgcttctc  ttggttggaa
3401  aatggaagag  aattacctgg  catcaatacg  acaatttccc
3441  aggatcctga  atctgaattg  tacaccatta  gtagccaact
3481  agatttcaat  acgactcgca  accacaccat  taagtgtctc
3521  attaaatatg  gagatgctca  cgtgtcagag  gacttcacct
3561  gggaaaaacc  cccagaagac  cctcctgata  gcaagcccgg
3601  gggtggtggg  agcggtggtg  gcggcagtgg  cggcggcgga
3641  actagtgagg  tccagcttca  gcagtctgga  cctgacctgg
3681  tgaagcctgg  ggcttcagtg  aagatatcct  gcaaggcttc
3721  tggttactca  ttcactggct  actacatgca  ctgggtgaag
3761  cagagccatg  gaaagagcct  tgagtggatt  ggacgtatta
3801  atcctaacaa  tggtgttact  ctctacaacc  agaaattcaa
3841  ggacaaggcc  atattaactg  tagacaagtc  atccaccaca
3881  gcctacatgg  agctccgcag  cctgacatct  gaggactctg
3921  cggtctatta  ctgtgcaaga  tctactatga  ttacgaacta
3961  tgttatggac  tactggggtc  aagtaacttc  agtcaccgtc
4001  tcttcaggtg  gtggtgggag  cggtggtggc  ggcactggcg
4041  gcggcggatc  tagtattgtg  atgacccaga  ctcccacatt
4081  cctgcttgtt  tcagcaggag  acagggttac  cataacctgc
4121  aaggccagtc  agagtgtgag  taatgatgta  gcttggtacc
4161  aacagaagcc  agggcagtct  cctacactgc  tcatatccta
4201  tacatccagt  cgctacgctg  gagtccctga  tcgcttcatt
4241  ggcagtggat  atgggacgga  tttcactttc  accatcagca
4281  ctttgcaggc  tgaagcctg   gcagtttatt  tctgtcagca
4321  agattataat  tctcctccga  cgttcggtgg  aggcaccaag
4361  ctggaaataa  aacggcggc   cgcagaacaa  aaactcatct
4401  cagaagagga  tctgaatagc  gccgtcgacc  atcatcacca
4441  tcaccattga  tctagtttcg  agggggggcc  cggacctact
4481  agggtgctgt  ggaagggtga  tggtgcagta  gtagttaatg
4521  atgaaggaaa  gggaataatt  gctgtaccat  taaccaggac
```

FIGURE 13C

```
4561  taagttacta ataaaaccaa attgagtatt gttgcaggaa
4601  gcaagaccca actaccattg tcagctgtgt ttcctgacct
4641  caatatttgt tataaggttt gatatgaatc caggggggaa
4681  tctcaacccc tattacccaa cagtcagaaa aatctaagtg
4721  tgaggagaac acaatgtttc aaccttattg ttataataat
4761  gacagtaaga acagcatggc agaatcgaag gaagcaagag
4801  accaagaatg aacctgaaag aagaatctaa agaagaaaaa
4841  agaagaaatg actggtggaa aataggtatg tttctgttat
4881  gcttagcagg aactactgga ggaatacttt ggtggtatga
4921  aggactccca cagcaacatt atatagggtt ggtggcgata
4961  gggggaagat taaacggatc tggccaatca aatgctatag
5001  aatgctgggg ttccttcccg gggtgtagac catttcaaaa
5041  ttacttcagt tatgagacca atagaaggtg accagtggtg
5081  cagggtcctc cggcagtcgt tacctgaaga aaaaattcca
5121  tcacaaacat gcatcgcgag aagacacctg ggaccaggcc
5161  caacacaaca tacacctagc aggcgtgacc ggtggatcag
5201  gggacaaata ctacaagcag aagtactcca ggaacgactg
5241  gaatggagaa tcagaggagt acaacaggcg gccaaagagc
5281  tgggtgaagt caatcgaggc atttggagag agctatattt
5321  ccgagaagac caaaggggag atttctcagc ctgggcggc
5361  tatcaacgag cacaagaacg gctctggggg gaacaatcct
5401  caccaagggt ccttagacct ggagattcga agcgaaggag
5441  gaaacattta tgactgttgc attaaagccc aagaaggaac
5481  tctcgctatc ccttgctgtg gatttccctt atggctattt
5521  tggggactag taattatagt aggacgcata gcaggctatg
5561  gattacgtgg actcgctgtt ataataagga tttgtattag
5601  aggcttaaat ttgatatttg aaataatcag aaaaatgctt
5641  gattatatta gcttcgatca ctagtgaatt cgcggccgct
5681  taatcaacct ctggattaca aaatttgtga aagattgact
5721  ggtattctta actatgttgc tccttttacg ctatgtggat
5761  acgctgcttt aatgcctttg tatcatgcta ttgcttcccg
5801  tatggctttc attttctcct ccttgtataa atcctggttg
5841  ctgtctcttt atgaggagtt gtggcccgtt gtcaggcaac
5881  gtggcgtggt gtgcactgtg tttgctgacg caaccccccac
5921  tggttggggc attgccacca cctgtcagct cctttccggg
5961  actttcgctt tcccccctccc tattgccacg gcggaactca
6001  tcgccgcctg ccttgcccgc tgctggacag gggctcggct
6041  gttgggcact gacaattccg tggtgttgtc ggggaagctg
6081  acgtcctttc catggctgct cgcctgtgtt gccacctgga
6121  ttctgcgcgg gacgtccttc tgctacgtcc cttcggccct
6161  caatccagcg gaccttcctt cccgcggcct gctgccggct
6201  ctgcggcctc ttccgcgtct tcgccttcgc cctcagacga
6241  gtcggatctc cctttgggcc gcctccccgc ctgatcgatc
6281  tcgacatcga attcccgcgg ccgctcgaca gcttatcgat
6321  accgtcgaat tggaagagct ttaaatcctg gcacatctca
6361  tgtatcaatg cctcagtatg tttagaaaaa caagggggga
6401  actgtggggt ttttatgagg ggttttatac aattgggcac
6441  tcagattctg cggtctgagt cccttctctg ctgggctgaa
6481  aaggcctttg taataaatat aattctctac tcagtccctg
6521  tctctagttt gtctgttcga gatcctacag agctcatgcc
6561  ttggcgtaat catggtcata gctgtttcct gtgtgaaatt
6601  gttatccgct cacaattcca cacaacatac gagccggaag
6641  cataaagtgt aaagcctggg gtgcctaatg agtgagctaa
6681  ctcacattaa ttgcgttgcg ctcactgccc gctttccagt
6721  cggaaacct gtcgtgccag ctgcattaat gaatcggcca
6761  acgcgcgggg agaggcggtt tgcgtattgg gcgctcttcc
6801  gcttcctcgc tcactgactc gctgcgctcg gtcgttcggc
6841  tgcggcgagc ggtatcagct cactcaaagg cggtaatacg
6881  gttatccaca gaatcagggg ataacgcagg aaagaacatg
```

FIGURE 13D

```
6921  tgagcaaaag gccagcaaaa ggccaggaac cgtaaaaagg
6961  ccgcgttgct ggcgtttttc cataggctcc gcccccctga
7001  cgagcatcac aaaaatcgac gctcaagtca gaggtggcga
7041  aacccgacag gactataaag ataccaggcg tttcccccctg
7081  gaagctccct cgtgcgctct cctgttccga ccctgccgct
7121  taccggatac ctgtccgcct ttctcccttc gggaagcgtg
7161  gcgctttctc atagctcacg ctgtaggtat ctcagttcgg
7201  tgtaggtcgt tcgctccaag ctgggctgtg tgcacgaacc
7241  ccccgttcag cccgaccgct gcgccttatc cggtaactat
7281  cgtcttgagt ccaacccggt aagacacgac ttatcgccac
7321  tggcagcagc cactggtaac aggattagca gagcgaggta
7361  tgtaggcggt gctacagagt tcttgaagtg gtggcctaac
7401  tacggctaca ctagaaggac agtatttggt atctgcgctc
7441  tgctgaagcc agttaccttc ggaaaaagag ttggtagctc
7481  ttgatccggc aaacaaacca ccgctggtag cggtggtttt
7521  tttgtttgca agcagcagat tacgcgcaga aaaaaggat
7561  ctcaagaaga tcctttgatc ttttctacgg ggtctgacgc
7601  tcagtggaac gaaaactcac gttaagggat tttggtcatg
7641  agattatcaa aaaggatctt cacctagatc cttttaaatt
7681  aaaaatgaag ttttaaatca atctaaagta tatatgagta
7721  aacttggtct gacagttacc aatgcttaat cagtgaggca
7761  cctatctcag cgatctgtct atttcgttca tccatagttg
7801  cctgactccc cgtcgtgtag ataactacga tacgggaggg
7841  cttaccatct ggccccagtg ctgcaatgat accgcgagac
7881  ccacgctcac cggctccaga tttatcagca ataaaccagc
7921  cagccggaag ggccgagcgc agaagtggtc ctgcaacttt
7961  atccgcctcc atccagtcta ttaattgttg ccgggaagct
8001  agagtaagta gttcgccagt taatagtttg cgcaacgttg
8041  ttgccattgc tacaggcatc gtggtgtcac gctcgtcgtt
8081  tggtatggct tcattcagct ccggttccca acgatcaagg
8121  cgagttacat gatcccccat gttgtgcaaa aaagcggtta
8161  gctccttcgg tcctccgatc gttgtcagaa gtaagttggc
8201  cgcagtgtta tcactcatgg ttatggcagc actgcataat
8241  tctcttactg tcatgccatc cgtaagatgc ttttctgtga
8281  ctggtgagta ctcaaccaag tcattctgag aatagtgtat
8321  gcggcgaccg agttgctctt gcccggcgtc aatacgggat
8361  aataccgcgc cacatagcag aactttaaaa gtgctcatca
8401  ttggaaaacg ttcttcgggg cgaaaactct caaggatctt
8441  accgctgttg agatccagtt cgatgtaacc cactcgtgca
8481  cccaactgat cttcagcatc ttttactttc accagcgttt
8521  ctgggtgagc aaaaacagga aggcaaaatg ccgcaaaaaa
8561  gggaataagg gcgacacgga aatgttgaat actcatactc
8601  ttccttttc aatattattg aagcatttat cagggttatt
8641  gtctcatgag cggatacata tttgaatgta tttagaaaaa
8681  taaacaaata ggggttccgc gcacatttcc ccgaaaagtg
8721  ccacctaaat tgtaagcgtt aatattttgt taaattcgc
8761  gttaattttt tgttaaatca gctcatttt taaccaatag
8801  gccgaaatcg gcaaaatccc ttataaatca aagaataga
8841  ccgagatagg gttgagtgtt gttccagttt ggaacaagag
8881  tccactatta aagaacgtgg actccaacgt caaagggcga
8921  aaaccgtct atcagggcga tgcccacta cgtgaaccat
8961  caccctaatc aagttttttg gggtcgaggt gccgtaaagc
9001  actaaatcgg aaccctaaag ggagcccccg atttagagct
9041  tgacggggaa agccaacctg gcttatcgaa attaatacga
9081  ctcactatag ggagaccggc  (SEQ ID NO:16)
```

Figure 14 A

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGCG
CTCAAGAAGTTAGAGAAGGTGACGGTACAAGGGTCTCAGAAATTAACTACTGGTAACTGT
AATTGGGCGCTAAGTCTAGTAGACTTATTTCATGATACCAACTTTGTAAAAGAAAAGGAC
TGGCAGCTGAGGGATGTCATTCCATTGCTGGAAGATGTAACTCAGACGCTGTCAGGACAA
GAAAGAGAGGCCTTTGAAAGAACATGGTGGGCAATTTCTGCTGTAAAGATGGGCCTCCAG
ATTAATAATGTAGTAGATGGAAAGGCATCATTCCAGCTCCTAAGAGCGAAATATGAAAAG
AAGACTGCTAATAAAAAGCAGTCTGAGCCCTCTGAAGAATATCTCTAGAGTCGACGCTCT
CATTACTTGTAACAAAGGGAGGGAAAGTATGGGAGGACAGACACCATGGGAAGTATTTAT
CACTAATCAAGCACAAGTAATACATGAGAAACTTTTACTACAGCAAGCACAATCCTCCAA
AAAATTTTGTTTTTACAAAATCCCTGGTGAACATGGTCGACTCTAGAACTAGTGGATCCC
CCGGGCTGCAGGAGTGGGGAGGCACGATGGCCGCTTGGTCGAGGCGGATCCGGCCATTA
GCCATATTATTCATTGGTTATATAGCATAAATCAATATTGGCTATTGGCCATTGCATACG
TTGTATCCATATCATAATATGTACATTTATATTGGCTCATGTCCAACATTACCGCCATGT
TGACATTGATTATTGACTAGTTATTAATAGTAATCAATTACGGGGTCATTAGTTCATAGC
CCATATATGGAGTTCCGCGTTACATAACTTACGGTAAATGGCCCGCCTGGCTGACCGCCC
AACGACCCCGCCCATTGACGTCAATAATGACGTATGTTCCCATAGTAACGCCAATAGGG
ACTTTCCATTGACGTCAATGGGTGGAGTATTTACGGTAAACTGCCCACTTGGCAGTACAT
CAAGTGTATCATATGCCAAGTACGCCCCCTATTGACGTCAATGACGGTAAATGGCCCGCC
TGGCATTATGCCCAGTACATGACCTTATGGGACTTTCCTACTTGGCAGTACATCTACGTA
TTAGTCATCGCTATTACCATGGTGATGCGGTTTTGGCAGTACATCAATGGGCGTGGATAG
CGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAA
ATGGGCGGTAGGCATGTACGGTGGGAGGTCTATATAAGCAGAGCTCGTTTAGTGAACCGT
CAGATCGCCTGGAGACGCCATCCACGCTGTTTTGACCTCCATAGAAGACACCGGGACCGA
TCCAGCCTCCGCGGCCCCAAGCTTGTTGGGATCCACCGGTCGCCACCATGGTGAGCAAGG
GCGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTCGTGACCACCC
TGACCTACGGCGTGCAGTGCTTCAGCCGCTACCCCGACCACATGAAGCAGCACGACTTCT
TCAAGTCCGCCATGCCCGAAGGCTACGTCCAGGAGCGCACCATCTTCTTCAAGGACGACG
GCAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTACA

FIGURE 14B

```
ACTACAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTACCAGC
AGAACACCCCCATCGGCGACGGCCCCGTGCTGCTGCCCGACAACCACTACCTGAGCACCC
AGTCCGCCCTGAGCAAAGACCCCAACGAGAAGCGCGATCACATGGTCCTGCTGGAGTTCG
TGACCGCCGCCGGGATCACTCTCGGCATGGACGAGCTGTACAAGTAAAGCGGCCGCGACT
CTAGAGTCGACCTCGAGGGGGGGCCCGGACCTACTAGGGTGCTGTGGAAGGGTGATGGTG
CAGTAGTAGTTAATGATGAAGGAAAGGGAATAATTGCTGTACCATTAACCAGGACTAAGT
TACTAATAAAACCAAATTGAGTATTGTTGCAGGAAGCAAGACCCAACTACCATTGTCAGC
TGTGTTTCCTGACCTCAATATTTGTTATAAGGTTTGATATGAATCCCAGGGGGAATCTCA
ACCCCTATTACCCAACAGTCAGAAAAATCTAAGTGTGAGGAGAACACAATGTTTCAACCT
TATTGTTATAATAATGACAGTAAGAACAGCATGGCAGAATCGAAGGAAGCAAGAGACCAA
GAATGAACCTGAAAGAAGAATCTAAAGAAGAAAAAGAAGAAATGACTGGTGGAAAATAG
GTATGTTTCTGTTATGCTTAGCAGGAACTACTGGAGGAATACTTTGGTGGTATGAAGGAC
TCCCACAGCAACATTATATAGGGTTGGTGGCGATAGGGGGAAGATTAAACGGATCTGGCC
AATCAAATGCTATAGAATGCTGGGGTTCCTTCCCGGGGTGTAGACCATTTCAAAATTACT
TCAGTTATGAGACCAATAGAAGGTGACCAGTGGTGCAGGGTCCTCCGGCAGTCGTTACCT
GAAGAAAAATTCCATCACAAACATGCATCGCGAGAAGACACCTGGGACCAGGCCCAACA
CAACATACACCTAGCAGGCGTGACCGGTGGATCAGGGGACAAATACTACAAGCAGAAGTA
CTCCAGGAACGACTGGAATGGAGAATCAGAGGAGTACAACAGGCGGCCAAAGAGCTGGGT
GAAGTCAATCGAGGCATTTGGAGAGAGCTATATTTCCGAGAAGACCAAAGGGGAGATTTC
TCAGCCTGGGGCGGCTATCAACGAGCACAAGAACGGCTCTGGGGGGAACAATCCTCACCA
AGGGTCCTTAGACCTGGAGATTCGAAGCGAAGGAGGAAACATTTATGACTGTTGCATTAA
AGCCCAAGAAGGAACTCTCGCTATCCCTTGCTGTGGATTTCCCTTATGGCTATTTTGGGG
ACTAGTAATTATAGTAGGAGGCATAGCAGGCTATGGATTACGTGGACTCGCTGTTATAAT
AAGGATTTGTATTAGAGGCTTAAATTTGATATTTGAAATAATCAGAAAAATGCTTGATTA
TATTAGCTTCGATCACTAGTGAATTCGCGGCCGCTTAATCAACCTCTGGATTACAAAATT
TGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTGGGCACTGACAATTCCGTGGTG
TTGTCGGGGAAGCTGACGTCCTTTCCATGGCTGCTCGCCTGTGTTGCCACCTGGATTCTG
CGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGG
ATCTCCCTTTGGGCCGCCTCCCCGCCTGATCGATCTCGACATCGAATTCCCGCGGCCGCT
CGACAGCTTATCGATACCGTCGAATTGGAAGAGCTTTAAATCCTGGCACATCTCATGTAT
CAATGCCTCAGTATGTTTAGAAAAACAAGGGGGGAACTGTGGGGTTTTATGAGGGGTTT
TATACAATTGGGCACTCAGATTCTGCGGTCTGAGTCCCTTCTCTGCTGGGCTGAAAAGGC
CTTTGTAATAAATATAATTCTCTACTCAGTCCCTGTCTCTAGTTTGTCTGTTCGAGATCC
TACAGAGCTCATGCCTTGGCGTAATCATGGTCATAGCTGTTTCCTGTGTGAAATTGTTAT
CCGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGGA
AACCTGTCGTGCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCA
GCAGCCACTGGTAACAGGATTAGCAGAGCGAGGTATGTAGGCGGTGCTACAGAGTTCTTG
AAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAA
GGGATTTTGGTCATGAGATTATCAAAAAGGATCTTCACCTAGATCCTTTTAAATTAAAAA
```

FIGURE 14C

TGAAGTTTTAAATCAATCTAAAGTATATATGAGTAAACTTGGTCTGACAGTTACCAATGC
TTAATCAGTGAGGCACCTATCTCAGCGATCTGTCTATTTCGTTCATCCATAGTTGCCTGA
CTCCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAGCC
GGAAGGGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTGTTGCC
ATTGCTACAGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGA
AAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGG
TGAGCAAAAACAGGAAGGCAAAATGCCGCAAAAAAGGGAATAAGGGCGACACGGAAATGT
TGAATACTCATACTCTTCCTTTTTCAATATTATTGAAGCATTTATCAGGGTTATTGTCTC
ATGAGCGGATACATATTTGAATGTATTTAGAAAAATAAACAAATAGGGGTTCCGCGCACA
TTTCCCCGAAAAGTGCCACCTAAATTGTAAGCGTTAATATTTTGTTAAAATTCGCGTTAA
ATTTTTGTTAAATCAGCTCATTTTTTAACCAATAGGCCGAAATCGGCAAAATCCCTTATA
AATCAAAAGAATAGACCGAGATAGGGTTGAGTGTTGTTCCAGTTTGGAACAAGAGTCCAC
TATTAAAGAACGTGGACTCCAACGTCAAAGGGCGAAAAACCGTCTATCAGGGCGATGGCC
CACTACGTGAACCATCACCCTAATCAAGTTTTTTGGGGTCGAGGTGCCGTAAAGCACTAA
ATCGGAACCCTAAAGGGAGCCCCCGATTTAGAGCTTGACGGGGAAAGCCAACCTGGCTTA
TCGAAATTAATACGACTCACTATAGGGAGACCGGC (SEQ ID NO:17)

SEQUENCE LISTING

<160> NUMBER OF SEQ ID NOS: 40

<210> SEQ ID NO 1
<211> LENGTH: 729
<212> TYPE: DNA
<213> ORGANISM: Artificial Sequence
<220> FEATURE:
<223> OTHER INFORMATION: DNA encoding a 5T4 scFv, designated 5T4scFv.1

<400> SEQUENCE: 1

```
gaggtccagc ttcagcagtc tggacctgac ctggtgaagc ctggggcttc agtgaagata      60
tcctgcaagg cttctggtta ctcattcact ggctactaca tgcactgggt gaagcagagc     120 catgaaaga  gccttgagtg gattggacgt attaatccta caatggtgt  tactctctac     180 aaccagaaat tcaaggacaa ggccatatta actgtagaca agtcatccac cacagcctac     240
atggagctcc gcagcctgac atctgaggac tctgcggtct attactgtgc aagatctact     300
atgattacga actatgttat ggactactgg ggtcaagtaa cctcagtcac cgtctcctca     360
ggtggtggtg ggagcggtgg tggcggcact ggcggcggcg atctagtat  tgtgatgacc     420 cagactccca cattcctgct tgtttcagca ggagacaggg ttaccataac ctgcaaggcc     480
agtcagagtg tgagtaatga tgtagdttgg taccaacaga agccagggca gtctcctaca     540
ctgctcatat cctatacatc cagtcgctac gctggagtcc ctgatcgctt cattggcagt     600
ggatatggga cggatttcac tttcaccatc agcactttgc aggctgaaga cctggcagtt     660
tatttctgtc agcaagatta taattctcct ccgacgttcg gtggaggcac caagctggaa     720
atcaaacgg                                                             729
```

<210> SEQ ID NO 2
<211> LENGTH: 1807
<212> TYPE: DNA
<213> ORGANISM: Artificial Sequence
<220> FEATURE:
<223> OTHER INFORMATION: cDNA sequence encoding 5T4Sab1

<400> SEQUENCE: 2

```
aagcttccac catgggatgg agctgtatca tcctcttctt ggtagcaaca gctacaggtg      60
tccactccga ggtccagctt cagcagtctg gacctgacct ggtgaagcct ggggcttcag     120
tgaagatatc ctgcaaggct tctggttact cattcactgg ctactacatg cactgggtga     180
agcagagcca tggaaagagc cttgagtgga ttggacgtat taatcctaac aatggtgtta     240
ctctctacaa ccagaaattc aaggacaagg ccatattaac tgtagacaag tcatccacca     300
cagcctacat ggagctccgc agcctgacat ctgaggactc tgcggtctat tactgtgcaa     360
gatctactat gattacgaac tatgttatgg actactgggg tcaagtaacc tcagtcaccg     420
tctcctcagg tggtggtggg agcggtggtg gcggcactgg cggcggcgga tctagtattg     480
tgatgaccca gactcccaca ttcctgcttg tttcagcagg agacagggtt accataacct     540
gcaaggccag tcagagtgtg agtaatgatg tagcttggta ccaacagaag ccagggcagt     600
ctcctacact gctcatatcc tatacatcca gtcgctacgc tggagtccct gatcgcttca     660
ttggcagtgg atatgggacg gatttcactt tcaccatcag cactttgcag gctgaagacc     720
tggcagttta tttctgtcag caagattata attcctccga cgttcggtgg aggcaccaag     780 ctggaaat   caaacgggcc tccaccaagg gcccatcggt cttccccctg gcaccctcct     840
ccaagagcac ctctgggggc acagcggccc tgggctgcct ggtcaaggac tacttccccg     900
```

-continued

```
aaccggtgac ggtgtcgtgg aactcaggcg ccctgaccag cggcgtgcac accttcccgg    960
ctgtcctaca gtcctcagga ctctactccc tcagcagcgt ggtgaccgtg ccctccagca   1020
gcttgggcac ccagacctac atctgcaacg tgaatcacaa gcccagcaac accaaggtgg   1080
acaagaaagt tgagcccaaa tcttgtgaca aaactcacac atgcccaccg tgcccagcac   1140
ctgaactcct ggggggaccg tcagtcttcc tcttccccc aaaacccaag gacaccctca   1200
tgatctcccg gacccctgag gtcacatgcg tggtggtgga cgtgagccac gaagaccctg   1260
aggtcaagtt caactggtac gtggacggcg tggaggtgca taatgccaag acaaagccgc   1320
gggaggagca gtacaacagc acgtaccgtg tggtcagcgt cctcaccgtc ctgcaccagg   1380
actggctgaa tggcaaggag tacaagtgca aggtctccaa caaagccctc ccagccccca   1440
tcgagaaaac catctccaaa gccaaggggc agccccgaga accacaggtg tacaccctgc   1500
ccccatcccg ggatgagctg accaagaacc aggtcagcct gacctgcctg gtcaaaggct   1560
tctatcccag cgacatcgcc gtggagtggg agagcaatgg gcagccggag aacaactaca   1620
agaccacgcc tcccgtgctg gactccgacg gctccttctt cctctacagc aagctcaccg   1680
tggacaagag caggtggcag caggggaacg tcttctcatg ctccgtgatg catgaggctc   1740
tgcacaacca ctacacgcag aagagcctct ccctgtctcc gggtaaatga gtgcgacggc   1800
caagctt                                                            1807

<210> SEQ ID NO 3
<211> LENGTH: 1467
<212> TYPE: DNA
<213> ORGANISM: Artificial Sequence
<220> FEATURE:
<223> OTHER INFORMATION: Sequence of B7-1.5T4.1

<400> SEQUENCE: 3
atgggccaca cacggaggca gggaacatca ccatccaagt gtccatacct caatttcttt     60
cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagtttcc caagatcctg aaactgagct ctatgctgtt    600
agcagcaaac tggatttcaa tatgacaacc aaccacagct tcatgtgtct catcaagtat    660
ggacatttaa gagtgaatca gaccttcaac tggaatacaa ccaagcaaga gcattttcct    720
gatggaggcg ggggatccga ggtccagctt cagcagtctg gacctgacct ggtgaagcct    780
ggggcttcag tgaagatatc ctgcaaggct tctggttact cattcactgg ctactacatg    840
cactgggtga agcagagcca tggaaagagc cttgagtgga ttggacgtat taatcctaac    900
aatggtgtta ctctctacaa ccagaaattc aaggacaagg ccatattaac tgtagacaag    960
tcatccacca gcctacat ggagctccgc agcctgacat ctgaggactc tgcggtctat    1020
tactgtgcaa gatctactat gattacgaac tatgttatgg actactgggg tcaagtaacc   1080
tcagtcaccg tctcctcagg tggtggtggg agcggtggtg gcggcactgg cggcggcgga   1140
```

| | |
|---|---:|
| tctagtattg tgatgaccca gactcccaca ttcctgcttg tttcagcagg agacagggtt | 1200 |
| accataacct gcaaggccag tcagagtgtg agtaatgatg tagcttggta ccaacagaag | 1260 |
| ccagggcagt ctcctacact gctcatatcc tatacatcca gtcgctacgc tggagtccct | 1320 |
| gatcgcttca ttggcagtgg atatgggacg gatttcactt tcaccatcag cactttgcag | 1380 |
| gctgaagacc tggcagttta tttctgtcag caagattata attctcctcc gacgttcggt | 1440 |
| ggaggcacca agctggaaat caaataa | 1467 |

<210> SEQ ID NO 4
<211> LENGTH: 738
<212> TYPE: DNA
<213> ORGANISM: Homo sapiens

<400> SEQUENCE: 4

| | |
|---|---:|
| atgggactga gtaacattct ctttgtgatg gccttcctgc tctctggtgc tgctcctctg | 60 |
| aagattcaag cttatttcaa tgagactgca gacctgccat gccaatttgc aaactctcaa | 120 |
| aaccaaagcc tgagtgagct agtagtattt tggcaggacc aggaaaactt ggttctgaat | 180 |
| gaggtatact taggcaaaga gaaatttgac agtgttcatt ccaagtatat gggccgcaca | 240 |
| agttttgatt cggacagttg gaccctgaga cttcacaatc ttcagatcaa ggacaagggc | 300 |
| ttgtatcaat gtatcatcca tcacaaaaag cccacaggaa tgattcgcat ccaccagatg | 360 |
| aattctgaac tgtcagtgct tgctaacttc agtcaacctg aaatagtacc aatttctaat | 420 |
| ataacagaaa atgtgtacat aaatttgacc tgctcatcta tacacggtta cccagaacct | 480 |
| aagaagatga gtgttttgct aagaaccaag aattcaacta tcgagtatga tggtattatg | 540 |
| cagaaatctc aagataatgt cacagaactg tacgacgttt ccatcagctt gtctgtttca | 600 |
| ttccctgatg ttacgagcaa tatgaccatc ttctgtattc tggaaactga caagacgcgg | 660 |
| cttttatctt cacctttctc tatagagctt gaggaccctc agcctccccc agaccacatt | 720 |
| cctggaggcg ggggatcc | 738 |

<210> SEQ ID NO 5
<211> LENGTH: 1518
<212> TYPE: DNA
<213> ORGANISM: Artificial Sequence
<220> FEATURE:
<223> OTHER INFORMATION: B7 Link scFv sequence

<400> SEQUENCE: 5

| | |
|---|---:|
| atggcttgca attgtcagtt gatgcaggat acaccactcc tcaagtttcc atgtccaagg | 60 |
| ctcattcttc tctttgtgct gctgattcgt ctttcacaag tgtcttcaga tgttgatgaa | 120 |
| caactgtcca agtcagtgaa agataaggta ttgctgcctt gccgttacaa ctctccgcat | 180 |
| gaagatgagt ctgaagaccg aatctactgg caaaaacatg acaaagtggt gctgtctgtc | 240 |
| attgctggga aactaaaagt gtggcccgag tataagaacc ggactttata tgacaacact | 300 |
| acctactctc ttatcatcct gggcctggtc ctttcagacc ggggcacata cagctgtgtc | 360 |
| gttcaaaaga aggaaagagg aacgtatgaa gttaaacact ggcttttagt aaagttgtcc | 420 |
| atcaaagctg acttctctac ccccaacata actgagtctg aaaccccatc tgcagacact | 480 |
| aaaaggatta cctgctttgc ttccgggggt ttcccaaagc ctcgcttctc ttggttggaa | 540 |
| aatggaagag aattacctgg catcaatacg acaatttccc aggatcctga atctgaattg | 600 |
| tacaccatta gtagccaact agatttcaat acgactcgca accacaccat taagtgtctc | 660 |
| attaaatatg gagatgctca cgtgtcagag gacttcacct gggaaaaacc cccagaagac | 720 |

-continued

| | |
|---|---|
| cctcctgata gcaagcccgg gggtggtggg agcggtggtg gcggcagtgg cggcggcgga | 780 |
| actagtgagg tccagcttca gcagtctgga cctgacctgg tgaagcctgg gcttcagtg | 840 |
| aagatatcct gcaaggcttc tggttactca ttcactggct actacatgca ctgggtgaag | 900 |
| cagagccatg gaaagagcct tgagtggatt ggacgtatta atcctaacaa tggtgttact | 960 |
| ctctacaacc agaaattcaa ggacaaggcc atattaactg tagacaagtc atccaccaca | 1020 |
| gcctacatgg agctccgcag cctgacatct gaggactctg cggtctatta ctgtgcaaga | 1080 |
| tctactatga ttacgaacta tgttatggac tactggggtc aagtaacttc agtcaccgtc | 1140 |
| tcttcaggtg gtggtgggag cggtggtggc ggcactggcg gcggcggatc tagtattgtg | 1200 |
| atgacccaga ctcccacatt cctgcttgtt tcagcaggag acagggttac cataacctgc | 1260 |
| aaggccagtc agagtgtgag taatgatgta gcttggtacc aacagaagcc agggcagtct | 1320 |
| cctacactgc tcatatccta tacatccagt cgctacgctg gagtccctga tcgcttcatt | 1380 |
| ggcagtggat atgggacgga tttcactttc accatcagca ctttgcaggc tgaagacctg | 1440 |
| gcagtttatt tctgtcagca agattataat tctcctccga cgttcggtgg aggcaccaag | 1500 |
| ctggaaatca aacggtaa | 1518 |

<210> SEQ ID NO 6
<211> LENGTH: 2090
<212> TYPE: DNA
<213> ORGANISM: Artificial Sequence
<220> FEATURE:
<223> OTHER INFORMATION: Similar fusion construct of 5T4scFv

<400> SEQUENCE: 6

| | |
|---|---|
| ctcgagccac catgggatgg agctgtatca tcctcttctt ggtagcaaca gctacaggtg | 60 |
| tccactccga ggtccagctg cagcagtctg gacctgacct ggtgaagcct ggggcttcag | 120 |
| tgaagatatc ctgcaaggct tctggttact cattcactgg ctactacatg cactgggtga | 180 |
| agcagagcca tggaaagagc cttgagtgga ttggacgtat taatcctaac aatggtgtta | 240 |
| ctctctacaa ccagaaattc aaggacaagg ccatattaac tgtagacaag tcatccacca | 300 |
| cagcctacat ggagctccgc agcctgacat ctgaggactc tgcggtctat tactgtgcaa | 360 |
| gatctactat gattacgaac tatgttatgg actactgggg tcaagtaact tcagtcaccg | 420 |
| tctcttcagg tggtggtggg agcggtggtg gcggcactgg cggcggcgga tctagtattg | 480 |
| tgatgaccca gactcccaca ttcctgcttg tttcagcagg agacagggtt accataacct | 540 |
| gcaaggccag tcagagtgtg agtaatgatg tagcttggta ccaacagaag ccagggcagt | 600 |
| ctcctacact gctcatatcc tatacatcca gtcgctacgc tggagtccct gatcgcttca | 660 |
| ttggcagtgg atatgggacg gatttcactt tcaccatcag cactttgcag gctgaagacc | 720 |
| tggcagttta tttctgtcag caagattata attctcctcc gacgttcggt ggaggcacca | 780 |
| agcttgaaat caaacgggcc tccacacaga gcccatccgt cttcccttg acccgctgct | 840 |
| gcaaaaacat tccctccaat gccacctccg tgactctggg ctgcctggcc acgggctact | 900 |
| tcccggagcc ggtgatggtg acctgggaca caggctccct caacgggaca actatgacct | 960 |
| taccagccac caccctcacg ctctctggtc actatgccac catcagcttg ctgaccgtct | 1020 |
| cgggtgcgtg ggccaagcag atgttcacct gccgtgtggc acacactcca tcgtccacag | 1080 |
| actgggtcga acaaaaaacc ttcagcgtct gctccaggga cttcacccg cccaccgtga | 1140 |
| agatcttaca gtcgtcctgc gacgcggcg ggcacttccc ccgaccatc cagctcctgt | 1200 |
| gcctcgtctc tgggtacacc ccagggacta tcaacatcac ctggctggag gacgggcagg | 1260 |

```
tcatggacgt ggacttgtcc accgcctcta ccacgcagga gggtgagctg gcctccacac    1320
aaagcgagct caccctcagc cagaagcact ggctgtcaga ccgcacctac acctgccagg    1380
tcacctatca aggtcacacc tttgaggaca gcaccaagaa gtgtgcagat tccaacccga    1440 gagggggtgag cgcctaccta agccggccca gcccgttcga cctgttcatc cgcaagtcgc    1500
ccacgatcac ctgtctggtg gtggacctgg cacccagcaa ggggaccgtg aacctgacct    1560
ggtcccgggc cagtgggaag cctgtgaacc actccaccag aaaggaggag aagcagcgca    1620
atggcacgtt aaccgtcacg tccaccctgc cggtgggcac ccgagactgg atcgaggggg    1680
agacctacca gtgcagggtg acccacccccc acctgcccag ggccctcatg cggtccacga    1740
ccaagaccag cggcccgcgt gctgccccgg aagtctatgc gtttgcgacg ccggagtggc    1800
cggggagccg ggacaagcgc accctcgcct gctgatccaa gaacttcatg cctgaggaca    1860
tctcggtgca gtggctgcac aacgaggtgc agctcccgga cgcccggcac agcacgacgc    1920
agccccgcaa gaccaaggc tccggcttct cgtcttcag ccgcctggag gtgaccaggg    1980
ccgaatggga gcagaaagat gagttcatct gccgtgcagt ccatgaggca gcgagcccct    2040
cacagaccgt ccagcgagcg gtgtctgtaa atcccggtaa atgagagctc                2090
```

<210> SEQ ID NO 7
<211> LENGTH: 945
<212> TYPE: DNA
<213> ORGANISM: Artificial Sequence
<220> FEATURE:
<223> OTHER INFORMATION: region of the gene encoding the mature EGF
      peptide

<400> SEQUENCE: 7

```
atggcttgca attgtcagtt gatgcaggat acaccactcc tcaagtttcc atgtccaagg     60
ctcattcttc tctttgtgct gctgattcgt ctttcacaag tgtcttcaga tgttgatgaa    120
caactgtcca agtcagtgaa agataaggta ttgctgcctt gccgttacaa ctctccgcat    180
gaagatgagt ctgaagaccg aatctactgg caaaaacatg acaaagtggt gctgtctgtc    240
attgctggga aactaaaagt gtggcccgag tataagaacc ggactttata tgacaacact    300
acctactctc ttatcatcct gggcctggtc ctttcagacc ggggcacata cagctgtgtc    360
gttcaaaaga aggaaagagg aacgtatgaa gttaaacact ggctttagt aaagttgtcc    420 atcaaagctg acttctctac ccccaacata actgagtctg aaacccatc tgcagacact    480 aaaaggatta cctgctttgc ttccgggggt ttcccaaagc ctcgcttctc ttggttggaa    540
aatggaagag aattacctgg catcaatacg acaatttccc aggatcctga atctgaattg    600
tacaccatta gtagccaact agatttcaat acgactcgca accacaccat taagtgtctc    660
attaaatatg gagatgctca cgtgtcagag gactccacct gggaaaaacc cccagaagac    720
cctcctgata gcaagcccgg gggtggtggg agcggtggtg gcggcagtgg cggcggcgga    780
actagtaata gtgactctga atgtccctg tcccacgatg ggtactgcct ccatgatggt    840
gtgtgcatgt atattgaagc attggacaag tatgcatgca actgtgttgt tggctacatc    900
ggggagcgat gtcagtaccg agacctgaag tggtgggaac tgcgc                     945
```

<210> SEQ ID NO 8
<211> LENGTH: 363
<212> TYPE: DNA
<213> ORGANISM: Artificial Sequence
<220> FEATURE:
<223> OTHER INFORMATION: Anti-TNF alpha VH

```
<400> SEQUENCE: 8
gaggtgcagc tggtggagtc tgggggaggc ttggtacagc ccggcaggtc cctgagactc        60
tcctgtgcgg cctctggatt cacctttgat gattatgcca tgcactgggt ccggcaagct       120
ccagggaagg gcctggaatg ggtctcagct atcacttgga atagtggtca catagactat       180
gcggactctg tggagggccg attcaccatc tccagagaca acgccaagaa ctccctgtat       240
ctgcaaatga acagtctgag agctgaggat acggccgtat attactgtgc gaaagtctcg       300
taccttagca ccgcgtcctc ccttgactat tggggccaag gtaccctggt caccgtctcg       360
agt                                                                    363

<210> SEQ ID NO 9
<211> LENGTH: 321
<212> TYPE: DNA
<213> ORGANISM: Artificial Sequence
<220> FEATURE:
<223> OTHER INFORMATION: Anti-TNF alpha VL

<400> SEQUENCE: 9
gacatcgtga tgacccagtc tccatcctcc ctgtctgcat ctataggga cagagtcacc         60 atcacttgtc gggaaagtca gggcatcaga aatgatttag ctggtatca gcagaaacca       120 gggaaagccc ctaagctcct gatctatgct gcatccagtt tgcaaagtgg ggtcccatca       180
aggttcagcg gcagtggatc tgggacagat ttcactctca ccatcagcag cctgcagcct       240
gaagattttg caacttactt ttgtcaacag gctaacagtc ccctcccac tttcggcgga       300 gggaccaagg tggaaatcaa a                                                321

<210> SEQ ID NO 10
<211> LENGTH: 789
<212> TYPE: DNA
<213> ORGANISM: Artificial Sequence
<220> FEATURE:
<223> OTHER INFORMATION: Anti-VEGF scFv

<400> SEQUENCE: 10
atggcccagg tgcagctggt gcagtctggg gctgaggtga agaagcctgg ggcctcagtg        60
aaggtttcct gcaaggcttc tggatacacc ttcactagct atgctatgca ttgggtgcgc       120
caggcccccg gacaaaggct tgagtggatg ggatggatca cgctggcaa tggtaacaca       180 aaatattcac agaagttcca gggcagagtc accattacca gggacacatc cgcgagcaca       240
gcctacatgg agctgagcag cctgagatct gaagacacgg ccgtgtatta ctgtgcaagg       300
ttgacgcgta ataagtttaa gtcgcgtggt cattggggcc aaggtaccct ggtcaccgtg       360
tcgagaggtg gcggtggctc gggcggtggt ggtcgggtg gcggcggatc ttctgagctg       420
actcaggacc ctgctgtgtc tgtggccttg ggacagacag tcaggatcac atgccaagga       480
gacagcctca gaagctatta tgcaagctgg taccagcaga gccaggacag gcccctgta      540 cttgtcatct atggtaaaaa caaccggccc tcaggatcc cagaccgatt ctctggctcc      600
agctcaggaa acacagcttc cttgaccatc actggggctc aggcggaaga tgaggctgac      660
tattactgta actcccggga cagcagtggt aaccatgtgg tattcggcgg agggaccaag      720
ctgaccgtcc taggtgcggc cgcagaacaa aaactcatct cagaagagga tctgaatggg      780
gccgcatag                                                             789
```

```
<210> SEQ ID NO 11
<211> LENGTH: 49
<212> TYPE: DNA
<213> ORGANISM: Artificial Sequence
<220> FEATURE:
<223> OTHER INFORMATION: oligonucleotide

<400> SEQUENCE: 11
ctagtaccgg tggtggtggg agcggtggtg gcggcagtgg cgggcggcg              49

<210> SEQ ID NO 12
<211> LENGTH: 48
<212> TYPE: DNA
<213> ORGANISM: Artificial Sequence
<220> FEATURE:
<223> OTHER INFORMATION: oligonucleotide

<400> SEQUENCE: 12
atggccacca ccaccctcgc caccaccgcc gtcaccgccg ccgcctag               48

<210> SEQ ID NO 13
<211> LENGTH: 15
<212> TYPE: PRT
<213> ORGANISM: Artificial Sequence
<220> FEATURE:
<223> OTHER INFORMATION: linker

<400> SEQUENCE: 13

Gly Gly Gly Gly Ser Gly Gly Gly Gly Ser Gly Gly Gly Gly Ser
 1               5                  10                  15

<210> SEQ ID NO 14
<211> LENGTH: 76
<212> TYPE: DNA
<213> ORGANISM: Artificial Sequence
<220> FEATURE:
<223> OTHER INFORMATION: anti-TNF alpha scFv

<400> SEQUENCE: 14
ctagacctgc aggccaccat gggatggagc tgtatcatcc tcttcttggt agcaacagct       60
acaggtgtac actccc                                                      76

<210> SEQ ID NO 15
<211> LENGTH: 76
<212> TYPE: DNA
<213> ORGANISM: Artificial Sequence
<220> FEATURE:
<223> OTHER INFORMATION: anti-TNF alpha scFv

<400> SEQUENCE: 15
tggacgtccg gtggtaccct acctcgacat agtaggagaa gaaccatcgt tgtcgatgtc       60
cacatgtgag ggttaa                                                      76

<210> SEQ ID NO 16
<211> LENGTH: 9100
<212> TYPE: DNA
<213> ORGANISM: Artificial Sequence
<220> FEATURE:
<223> OTHER INFORMATION: nuc sequence of the SMART2 LscFvB7.1 5' cPPT
      plasmid

<400> SEQUENCE: 16
agatcttgaa taataaaatg tgtgtttgtc cgaaatacgc gttttgagat ttctgtcgcc       60
gactaaattc atgtcgcgcg atagtggtgt ttatcgccga tagagatggc gatattggaa     120
```

```
aaattgatat tgaaaatat ggcatattga aaatgtcgcc gatgtgagtt tctgtgtaac      180
tgatatcgcc attttccaa aagtgatttt tgggcatacg cgatatctgg cgatagcgct      240
tatatcgttt acgggggatg gcgatagacg actttggtga cttgggcgat tctgtgtgtc      300
gcaaatatcg cagtttcgat ataggtgaca gacgatatga ggctatatcg ccgatagagg      360
cgacatcaag ctggcacatg gccaatgcat atcgatctat acattgaatc aatattggcc      420
attagccata ttattcattg gttatatagc ataaatcaat attggctatt ggccattgca      480
tacgttgtat ccatatcgta atatgtacat ttatattggc tcatgtccaa cattaccgcc      540
atgttgacat tgattattga ctagttatta atagtaatca attacggggt cattagttca      600
tagcccatat atggagttcc gcgttacata acttacggta aatggcccgc ctggctgacc      660
gcccaacgac ccccgcccat tgacgtcaat aatgacgtat gttcccatag taacgccaat      720
agggactttc cattgacgtc aatgggtgga gtatttacgg taaactgccc acttggcagt      780
acatcaagtg tatcatatgc caagtccgcc ccctattgac gtcaatgacg gtaaatggcc      840
cgcctggcat tatgcccagt acatgacctt acgggacttt cctacttggc agtacatcta      900
cgtattagtc atcgctatta ccatggtgat gcggttttgg cagtacacca atgggcgtgg      960
atagcggttt gactcacggg gatttccaag tctccacccc attgacgtca atgggagttt     1020
gttttggcac caaaatcaac gggactttcc aaaatgtcgt aacaactgcg atcgcccgcc     1080
ccgttgacgc aaatgggcgg taggcgtgta cggtgggagg tctatataag cagagctcgt     1140
ttagtgaacc gggcactcag attctgcggt ctgagtccct tctctgctgg gctgaaaagg     1200
cctttgtaat aaatataatt ctctactcag tccctgtctc tagtttgtct gttcgagatc     1260
ctacagttgg cgcccgaaca gggacctgag aggggcgcag accctacctg ttgaacctgg     1320
ctgatcgtag gatccccggg acagcagagg agaacttaca gaagtcttct ggaggtgttc     1380
ctggccagaa cacaggagga caggtaagat tgggagaccc tttgacattg gagcaaggcg     1440
ctcaagaagt tagagaaggt gacggtacaa gggtctcaga aattaactac tggtaactgt     1500
aattgggcgc taagtctagt agacttattt catgatacca actttgtaaa agaaaaggac     1560
tggcagctga gggatgtcat tccattgctg gaagatgtaa ctcagacgct gtcaggacaa     1620
gaaagagagg cctttgaaag aacatggtgg gcaatttctg ctgtaaagat gggcctccag     1680
attaataatg tagtagatgg aaaggcatca ttccagctcc taagagcgaa atatgaaaag     1740
aagactgcta ataaaaagca gtctgagccc tctgaagaat atctctagag tcgacgctct     1800
cattacttgt aacaaaggga gggaaagtat gggaggacag acaccatggg aagtatttat     1860
cactaatcaa gcacaagtaa tacatgagaa acttttacta cagcaagcac aatcctccaa     1920
aaaattttgt ttttacaaaa tccctggtga acatggtcga ctctagaact agtggatccc     1980
ccgggctgca ggagtgggga ggcacgatgg ccgctttggt cgaggcggat ccggccatta     2040
gccatattat tcattggtta tatagcataa atcaatattg ctattggcc attgcatacg     2100
ttgtatccat atcataatat gtacatttat attggctcat gtccaacatt accgccatgt     2160
tgacattgat tattgactag ttattaatag taatcaatta cggggtcatt agttcatagc     2220
ccatatatgg agttccgcgt tacataactt acggtaaatg gcccgcctgg ctgaccgccc     2280
aacgacccc gcccattgac gtcaataatg acgtatgttc ccatagtaac gccaataggg     2340
actttccatt gacgtcaatg ggtggagtat ttacggtaaa ctgcccactt ggcagtacat     2400
caagtgtatc atatgccaag tacgcccct attgacgtca atgacggtaa atggcccgcc     2460
tggcattatg cccagtacat gaccttatgg gactttccta cttggcagta catctacgta     2520
```

-continued

```
ttagtcatcg ctattaccat ggtgatgcgg ttttggcagt acatcaatgg gcgtggatag      2580
cggtttgact cacggggatt tccaagtctc caccccattg acgtcaatgg gagtttgttt      2640
tggcaccaaa atcaacggga ctttccaaaa tgtcgtaaca actccgcccc attgacgcaa      2700
atgggcggta ggcatgtacg gtgggaggtc tatataagca gagctcgttt agtgaaccgt      2760
cagatcgcct ggagacgcca tccacgctgt tttgacctcc atagaagaca ccgggaccga      2820
tccagcctcc gcggccccaa gcttgatatc gaattccacc atggcttgca attgtcagtt      2880
gatgcaggat acaccactcc tcaagttttcc atgtccaagg ctcattcttc tctttgtgct      2940
gctgattcgt ctttcacaag tgtcttcaga tgttgatgaa caactgtcca agtcagtgaa      3000
agataaggta ttgctgcctt gccgttacaa ctctccgcat gaagatgagt ctgaagaccg      3060
aatctactgg caaaaacatg acaaagtggt gctgtctgtc attgctggga aactaaaagt      3120
gtggcccgag tataagaacc ggactttata tgacaacact acctactctc ttatcatcct      3180
gggcctggtc ctttcagacc ggggcacata cagctgtgtc gttcaaaaga aggaaagagg      3240
aacgtatgaa gttaaacact tggctttagt aaagttgtcc atcaaagctg acttctctac      3300 cccaacata actgagtctg gaaacccatc tgcagacact aaaaggatta cctgctttgc       3360 ttccggggt tcccaaagc ctcgcttctc ttggttggaa aatggaagag aattacctgg        3420
catcaatacg acaatttccc aggatcctga atctgaattg tacaccatta gtagccaact      3480
agatttcaat acgactcgca accacaccat taagtgtctc attaaatatg gagatgctca      3540
cgtgtcagag gacttcacct gggaaaaacc cccagaagac cctcctgata gcaagcccgg      3600
gggtggtggg agcggtggtg gcggcagtgg cggcggcgga actagtgagg tccagcttca      3660
gcagtctgga cctgacctgg tgaagcctgg ggcttcagtg aagatatcct gcaaggcttc      3720
tggttactca ttcactggct actacatgca ctgggtgaag cagagccatg gaaagagcct      3780
tgagtggatt ggacgtatta atcctaacaa tggtgttact ctctacaacc agaaattcaa      3840
ggacaaggcc atattaactg tagacaagtc atccaccaca gcctacatgg agctccgcag      3900
cctgacatct gaggactctg cggtctatta ctgtgcaaga tctactatga ttacgaacta      3960
tgttatggac tactggggtc aagtaacttc agtcaccgtc tcttcaggtg gtggtgggag      4020
cggtggtggc ggcactggcg gcggcggatc tagtattgtg atgacccaga ctcccacatt      4080
cctgcttgtt tcagcaggag acagggttac cataacctgc aaggccagtc agagtgtgag      4140
taatgatgta gcttggtacc aacagaagcc agggcagtct cctacactgc tcatatccta      4200
tacatccagt cgctacgctg gagtccctga tcgcttcatt ggcagtggat atgggacgga      4260
tttcactttc accatcagca ctttgcaggc tgaagacctg gcagtttatt tctgtcagca      4320
agattataat tctcctccga cgttcggtgg aggcaccaag ctggaaataa aacgggcggc      4380
cgcagaacaa aaactcatct cagaagagga tctgaatagc gccgtcgacc atcatcacca      4440
tcaccattga tctagtttcg aggggggggcc cggacctact agggtgctgt ggaagggtga      4500
tggtgcagta gtagttaatg atgaaggaaa gggaataatt gctgtaccat taaccaggac      4560
taagttacta ataaaaccaa attgagtatt gttgcaggaa gcaagaccca actaccattg      4620
tcagctgtgt ttcctgacct caatatttgt tataaggttt gatatgaatc cagggggaa      4680 tctcaaccc tattacccaa cagtcagaaa atctaagtg tgaggagaac acaatgtttc       4740
aaccttattg ttataataat gacagtaaga acagcatggc agaatcgaag gaagcaagag      4800
accaagaatg aacctgaaag aagaatctaa agaagaaaaa agaagaaatg actggtggaa      4860
aataggtatg tttctgttat gcttagcagg aactactgga ggaatacttt ggtggtatga      4920
```

```
aggactccca cagcaacatt atatagggtt ggtggcgata gggggaagat taaacgatc    4980 tggccaatca aatgctatag aatgctgggg ttccttcccg gggtgtagac catttcaaaa   5040
ttacttcagt tatgagacca atagaaggta accagtggtg cagggtcctc cggcagtcgt   5100
tacctgaaga aaaaattcca tcacaaacat gcatcgcgag aagacacctg ggaccaggcc   5160
caacacaaca tacacctagc aggcgtgacc ggtggatcag gggacaaata ctacaagcag   5220
aagtactcca ggaacgactg gaatggagaa tcagaggagt acaacaggcg ccaaagagc    5280 tgggtgaagt caatcgaggc atttggagag agctatattt ccgagaagac caaaggggag   5340
atttctcagc ctggggcggc tatcaacgag cacaagaacg gctctggggg gaacaatcct   5400
caccaagggt ccttagacct ggagattcga agcgaaggag gaaacattta tgactgttgc   5460
attaaagccc aagaaggaac tctcgctatc ccttgctgtg gatttccctt atggctattt   5520
tggggactag taattatagt aggacgcata gcaggctatg gattacgtgg actcgctgtt   5580
ataataagga tttgtattag aggcttaaat ttgatatttg aaataatcag aaaaatgctt   5640
gattatatta gcttcgatca ctagtgaatt cgcggccgct taatcaacct ctggattaca   5700
aaatttgtga agattgact ggtattctta actatgttgc tccttttacg ctatgtggat    5760
acgctgcttt aatgcctttg tatcatgcta ttgcttcccg tatggctttc attttctcct   5820
ccttgtataa atcctggttg ctgtctcttt atgaggagtt gtgggcccgtt gtcaggcaac   5880 gtggcgtggt gtgcactgtg tttgctgacg caacccccac tggttggggc attgccacca   5940
cctgtcagct ccttttccggg actttcgctt tcccccctcc tattgccacg gcggaactca   6000
tcgccgcctg ccttgcccgc tgctggacag gggctcggct gttgggcact gacaattccg   6060
tggtgttgtc ggggaagctg acgtcctttc catggctgct cgcctgtgtt gccacctgga   6120
ttctgcgcgg gacgtccttc tgctacgtcc cttcggccct caatccagcg gaccttcctt   6180
cccgcggcct gctgccggct ctgcggcctc ttccgcgtct tcgccttcgc cctcagacga   6240
gtcggatctc cctttgggcc gcctccccgc ctgatcgatc tcgacatcga attcccgcgg   6300
ccgctcgaca gcttatcgat accgtcgaat tggaagagct ttaaatcctg gcacatctca   6360
tgtatcaatg cctcagtatg tttagaaaaa caaggggggga actgtggggt ttttatgagg   6420
ggttttatac aattgggcac tcagattctg cggtctgagt cccttctctg ctgggctgaa   6480
aaggcctttg taataaatat aattctctac tcagtccctg tctctagttt gtctgttcga   6540
gatcctacag agctcatgcc ttggcgtaat catggtcata gctgtttcct gtgtgaaatt   6600
gttatccgct cacaattcca cacaacatac gagccggaag cataaagtgt aaagcctggg   6660
gtgcctaatg agtgagctaa ctcacattaa ttgcgttgcg ctcactgccc gctttccagt   6720
cgggaaacct gtcgtgccag ctgcattaat gaatcggcca acgcgcgggg agaggcggtt   6780
tgcgtattgg gcgctcttcc gcttcctcgc tcactgactc gctgcgctcg tcgttcggc    6840 tgcggcgagc ggtatcagct cactcaaagg cggtaatacg ttatccaca gaatcagggg    6900 ataacgcagg aaagaacatg tgagcaaaag gccagcaaaa ggccaggaac cgtaaaaagg   6960
ccgcgttgct ggcgtttttc cataggctcc gcccccctga cgagcatcac aaaaatcgac   7020
gctcaagtca gaggtggcga aacccgacag gactataaag ataccaggcg tttccccctg   7080
gaagctccct cgtgcgctct cctgttccga cctgccgct taccggatac ctgtccgcct    7140
ttctcccttc gggaagcgtg gcgctttctc atagctcacg ctgtaggtat ctcagttcgg   7200
tgtaggtcgt tcgctccaag ctgggctgtg tgcacgaacc ccccgttcag cccgaccgct   7260
gcgccttatc cggtaactat cgtcttgagt ccaacccggt aagacacgac ttatcgccac   7320
```

```
tggcagcagc cactggtaac aggattagca gagcgaggta tgtaggcggt gctacagagt    7380
tcttgaagtg gtggcctaac tacggctaca ctagaaggac agtatttggt atctgcgctc    7440
tgctgaagcc agttaccttc ggaaaaagag ttggtagctc ttgatccggc aaacaaacca    7500
ccgctggtag cggtggtttt tttgtttgca agcagcagat tacgcgcaga aaaaaggat    7560 ctcaagaaga tcctttgatc ttttctacgg ggtctgacgc tcagtggaac gaaaactcac    7620
gttaagggat tttggtcatg agattatcaa aaaggatctt cacctagatc cttttaaatt    7680
aaaaatgaag ttttaaatca atctaaagta tatatgagta aacttggtct gacagttacc    7740
aatgcttaat cagtgaggca cctatctcag cgatctgtct atttcgttca tccatagttg    7800
cctgactccc cgtcgtgtag ataactacga tacgggaggg cttaccatct ggccccagtg    7860
ctgcaatgat accgcgagac ccacgctcac cggctccaga tttatcagca ataaaccagc    7920
cagccggaag ggccgagcgc agaagtggtc ctgcaacttt atccgcctcc atccagtcta    7980
ttaattgttg ccgggaagct agagtaagta gttcgccagt taatagtttg cgcaacgttg    8040
ttgccattgc tacaggcatc gtggtgtcac gctcgtcgtt tggtatggct tcattcagct    8100
ccggttccca acgatcaagg cgagttacat gatcccccat gttgtgcaaa aaagcggtta    8160
gctccttcgg tcctccgatc gttgtcagaa gtaagttggc cgcagtgtta tcactcatgg    8220
ttatggcagc actgcataat tctcttactg tcatgccatc cgtaagatgc ttttctgtga    8280
ctggtgagta ctcaaccaag tcattctgag aatagtgtat gcggcgaccg agttgctctt    8340
gcccggcgtc aatacgggat aataccgcgc cacatagcag aactttaaaa gtgctcatca    8400
ttggaaaacg ttcttcgggg cgaaaactct caaggatctt accgctgttg agatccagtt    8460
cgatgtaacc cactcgtgca cccaactgat cttcagcatc ttttactttc accagcgttt    8520
ctgggtgagc aaaaacagga aggcaaaatg ccgcaaaaaa gggaataagg gcgacacgga    8580
aatgttgaat actcatactc ttcctttttc aatattattg aagcatttat cagggttatt    8640
gtctcatgag cggatacata tttgaatgta tttagaaaaa taaacaaata ggggttccgc    8700
gcacatttcc ccgaaaagtg ccacctaaat tgtaagcgtt aatattttgt taaaattcgc    8760
gttaattttt tgttaaatca gctcattttt taaccaatag gccgaaatcg gcaaaatccc    8820
ttataaatca aaagaataga ccgagatagg gttgagtgtt gttccagttt ggaacaagag    8880
tccactatta agaacgtgg actccaacgt caaagggcga aaaccgtct atcagggcga    8940 tggcccacta cgtgaaccat caccctaatc aagttttttg gggtcgaggt gccgtaaagc    9000
actaaatcgg aaccctaaag ggagccccg atttagagct tgacgggaa agccaacctg    9060 gcttatcgaa attaatacga ctcactatag ggagaccggc                         9100
```

<210> SEQ ID NO 17
<211> LENGTH: 8255
<212> TYPE: DNA
<213> ORGANISM: Artificial Sequence
<220> FEATURE:
<223> OTHER INFORMATION: nuc sequence of the SMART2G5' cPPT plasmid

<400> SEQUENCE: 17

```
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaattgatat ttgaaaatat ggcatattga aaatgtcgcc gatgtgagtt tctgtgtaac     180
tgatatcgcc attttccaa aagtgatttt tgggcatacg cgatatctgg cgatagcgct     240
tatatcgttt acggggatg gcgatagacg actttggtga cttgggcgat tctgtgtgtc     300
```

-continued

```
gcaaatatcg cagtttcgat ataggtgaca gacgatatga ggctatatcg ccgatagagg      360
cgacatcaag ctggcacatg gccaatgcat atcgatctat acattgaatc aatattggcc      420
attagccata ttattcattg gttatatagc ataaatcaat attggctatt ggccattgca      480
tacgttgtat ccatatcgta atatgtacat ttatattggc tcatgtccaa cattaccgcc      540
atgttgacat tgattattga ctagttatta atagtaatca attacggggt cattagttca      600
tagcccatat atggagttcc gcgttacata acttacggta aatggcccgc ctggctgacc      660
gcccaacgac ccccgcccat tgacgtcaat aatgacgtat gttcccatag taacgccaat      720
agggactttc cattgacgtc aatgggtgga gtatttacgg taaactgccc acttggcagt      780
acatcaagtg tatcatatgc caagtccgcc ccctattgac gtcaatgacg gtaaatggcc      840
cgcctggcat tatgcccagt acatgacctt acgggacttt cctacttggc agtacatcta      900
cgtattagtc atcgctatta ccatggtgat gcggttttgg cagtacacca atgggcgtgg      960
atagcggttt gactcacggg gatttccaag tctccacccc attgacgtca atgggagttt     1020
gttttggcac caaaatcaac gggactttcc aaaatgtcgt aacaactgcg atcgcccgcc     1080
ccgttgacgc aaatgggcgg taggcgtgta cggtgggagg tctatataag cagagctcgt     1140
ttagtgaacc gggcactcag attctgcggt ctgagtccct tctctgctgg gctgaaaagg     1200
cctttgtaat aaatataatt ctctactcag tccctgtctc tagtttgtct gttcgagatc     1260
ctacagttgg cgcccgaaca gggacctgag aggggcgcag accctacctg ttgaacctgg     1320
ctgatcgtag gatccccggg acagcagagg agaacttaca gaagtcttct ggaggtgttc     1380
ctggccagaa cacaggagga caggtaagat tgggagaccc tttgacattg gagcaaggcg     1440
ctcaagaagt tagagaaggt gacggtacaa gggtctcaga aattaactac tggtaactgt     1500
aattgggcgc taagtctagt agacttattt catgatacca actttgtaaa agaaaaggac     1560
tggcagctga gggatgtcat tccattgctg gaagatgtaa ctcagacgct gtcaggacaa     1620
gaaagagagg cctttgaaag aacatggtgg gcaatttctg ctgtaaagat gggcctccag     1680
attaataatg tagtagatgg aaaggcatca ttccagctcc taagagcgaa atatgaaaag     1740
aagactgcta ataaaaagca gtctgagccc tctgaagaat atctctagag tcgacgctct     1800
cattacttgt aacaagggag gggaaagtat gggaggacag acaccatggg aagtatttat     1860
cactaatcaa gcacaagtaa tacatgagaa acttttacta cagcaagcac aatcctccaa     1920 aaaatttgt ttttacaaaa tccctggtga acatggtcga ctctagaact agtggatccc     1980
ccgggctgca ggagtgggga ggcacgatgg ccgctttggt cgaggcggat ccggccatta     2040
gccatattat tcattggtta tatagcataa atcaatattg ctattggcc attgcatacg      2100 ttgtatccat atcataatat gtacatttat attggctcat gtccaacatt accgccatgt      2160
tgacattgat tattgactag ttattaatag taatcaatta cggggtcatt agttcatagc      2220
ccatatatgg agttccgcgt tacataactt acggtaaatg gcccgcctgg ctgaccgccc      2280
aacgaccccc gcccattgac gtcaataatg acgtatgttc ccatagtaac gccataggg      2340 actttccatt gacgtcaatg gtggagtat ttacggtaaa ctgcccactt ggcagtacat      2400
caagtgtatc atatgccaag tacgccccct attgacgtca atgacggtaa atggcccgcc      2460
tggcattatg cccagtacat gaccttatgg gactttccta cttggcagta catctacgta      2520
ttagtcatcg ctattaccat ggtgatgcgg ttttggcagt acatcaatgg gcgtggatag      2580
cggtttgact cacggggatt tccaagtctc caccccattg acgtcaatgg gagtttgttt      2640
tggcaccaaa atcaacggga ctttccaaaa tgtcgtaaca actccgcccc attgacgcaa      2700
```

```
atgggcggta ggcatgtacg gtgggaggtc tatataagca gagctcgttt agtgaaccgt   2760
cagatcgcct ggagacgcca tccacgctgt tttgacctcc atagaagaca ccgggaccga   2820
tccagcctcc gcggcccaa  gcttgttggg atccaccggt cgccaccatg gtgagcaagg   2880
gcgaggagct gttcaccggg gtggtgccca tcctggtcga gctggacggc gacgtaaacg   2940
gccacaagtt cagcgtgtcc ggcgagggcg agggcgatgc cacctacggc aagctgaccc   3000
tgaagttcat ctgcaccacc ggcaagctgc ccgtgccctg gcccaccctc gtgaccaccc   3060
tgacctacgg cgtgcagtgc ttcagccgct accccgacca catgaagcag cacgacttct   3120
tcaagtccgc catgcccgaa ggctacgtcc aggagcgcac catcttcttc aaggacgacg   3180
gcaactacaa gacccgcgcc gaggtgaagt tcgagggcga caccctggtg aaccgcatcg   3240
agctgaaggg catcgacttc aaggaggacg gcaacatcct ggggcacaag ctggagtaca   3300
actacaacag ccacaacgtc tatatcatgg ccgacaagca gaagaacggc atcaaggtga   3360
acttcaagat ccgccacaac atcgaggacg gcagcgtgca gctcgccgac cactaccagc   3420
agaacacccc catcggcgac ggccccgtgc tgctgcccga caaccactac ctgagcaccc   3480
agtccgccct gagcaaagac cccaacgaga gcgcgatca  catggtcctg ctggagttcg   3540
tgaccgccgc cgggatcact ctcggcatgg acgagctgta caagtaaagc ggccgcgact   3600
ctagagtcga cctcgagggg gggcccggac tactagggt  gctgtggaag ggtgatggtg   3660
cagtagtagt taatgatgaa ggaaagggaa taattgctgt accattaacc aggactaagt   3720
tactaataaa accaaattga gtattgttgc aggaagcaag acccaactac cattgtcagc   3780
tgtgtttcct gacctcaata tttgttataa ggtttgatat gaatcccagg gggaatctca   3840 accccctatta cccaacagtc agaaaaatct aagtgtgagg agaacacaat gtttcaacct   3900
tattgttata ataatgacag taagaacagc atggcagaat cgaaggaagc aagagaccaa   3960
gaatgaacct gaaagaagaa tctaaagaag aaaaaagaag aaatgactgg tggaaaatag   4020
gtatgtttct gttatgctta gcaggaacta ctggaggaat actttggtgg tatgaaggac   4080
tcccacagca acattatata gggttggtgg cgataggggg aagattaaac ggatctggcc   4140
aatcaaatgc tatagaatgc tggggttcct tcccgggggtg tagaccattt caaaattact   4200
tcagttatga gaccaataga aggtgaccag tggtgcaggg tcctccggca gtcgttacct   4260
gaagaaaaaa ttccatcaca aacatgcatc gcgagaagac acctgggacc aggcccaaca   4320
caacatacac ctagcaggcg tgaccggtgg atcaggggac aaatactaca agcagaagta   4380
ctccaggaac gactggaatg gagaatcaga ggagtacaac aggcggccaa agagctgggt   4440
gaagtcaatc gaggcatttg gagagagcta tatttccgag aagaccaaag gggagatttc   4500
tcagcctggg gcggctatca acgagcacaa gaacggctct gggggaaca  atcctcacca   4560 agggtcctta gacctggaga ttcgaagcga aggaggaaac atttatgact gttgcattaa   4620
agcccaagaa ggaactctcg ctatcccttg ctgtggattt cccttatggc tattttgggg   4680
actagtaatt atagtaggac gcatagcagg ctatggatta cgtggactcg ctgttataat   4740
aaggatttgt attagaggct taaatttgat atttgaaata atcagaaaaa tgcttgatta   4800
tattagcttc gatcactagt gaattcgcgg ccgcttaatc aacctctgga ttacaaaatt   4860
tgtgaaagat tgactggtat tcttaactat gttgctcctt ttacgctatg tggatacgct   4920
gctttaatgc ctttgtatca tgctattgct tcccgtatgg ctttcatttt ctcctccttg   4980
tataaatcct ggttgctgtc tctttatgag gagttgtggc ccgttgtcag caacgtggc    5040 gtggtgtgca ctgtgtttgc tgacgcaacc cccactggtt ggggcattgc caccacctgt   5100
```

```
cagctccttt ccgggacttt cgctttcccc ctccctattg ccacggcgga actcatcgcc    5160
gcctgccttg cccgctgctg gacaggggct cggctgttgg gcactgacaa ttccgtggtg    5220
ttgtcgggga agctgacgtc ctttccatgg ctgctcgcct gtgttgccac ctggattctg    5280
cgcgggacgt ccttctgcta cgtcccttcg gccctcaatc cagcggacct tccttcccgc    5340
ggcctgctgc cggctctgcg gcctcttccg cgtcttcgcc ttcgccctca gacgagtcgg    5400
atctcccttt gggccgcctc cccgcctgat cgatctcgac atcgaattcc cgcggccgct    5460
cgacagctta tcgataccgt cgaattggaa gagctttaaa tcctggcaca tctcatgtat    5520
caatgcctca gtatgtttag aaaaacaagg ggggaactgt ggggttttta tgaggggttt    5580
tatacaattg ggcactcaga ttctgcggtc tgagtccctt ctctgctggg ctgaaaaggc    5640
ctttgtaata aatataattc tctactcagt ccctgtctct agtttgtctg ttcgagatcc    5700
tacagagctc atgccttggc gtaatcatgg tcatagctgt ttcctgtgtg aaattgttat    5760
ccgctcacaa ttccacacaa catacgagcc ggaagcataa agtgtaaagc ctggggtgcc    5820
taatgagtga gctaactcac attaattgcg ttgcgctcac tgcccgcttt ccagtcggga    5880
aacctgtcgt gccagctgca ttaatgaatc ggccaacgcg cggggagagg cggtttgcgt    5940
attgggcgct cttccgcttc ctcgctcact gactcgctgc gctcggtcgt tcggctgcgg    6000
cgagcggtat cagctcactc aaaggcggta atacggttat ccacagaatc aggggataac    6060
gcaggaaaga acatgtgagc aaaaggccag caaaaggcca ggaaccgtaa aaaggccgcg    6120
ttgctggcgt ttttccatag gctccgcccc cctgacgagc atcacaaaaa tcgacgctca    6180
agtcagaggt ggcgaaaccc gacaggacta taaagatacc aggcgtttcc ccctggaagc    6240
tccctcgtgc gctctcctgt tccgaccctg ccgcttaccg gatacctgtc cgcctttctc    6300
ccttcgggaa gcgtggcgct ttctcatagc tcacgctgta ggtatctcag ttcggtgtag    6360
gtcgttcgct ccaagctggg ctgtgtgcac gaaccccccg ttcagcccga ccgctgcgcc    6420
ttatccggta actatcgtct tgagtccaac ccggtaagac acgacttatc gccactggca    6480
gcagccactg gtaacaggat tagcagagcg aggtatgtag gcggtgctac agagttcttg    6540
aagtggtggc ctaactacgg ctacactaga aggacagtat ttggtatctg cgctctgctg    6600
aagccagtta ccttcggaaa aagagttggt agctcttgat ccggcaaaca aaccaccgct    6660
ggtagcggtg gtttttttgt ttgcaagcag cagattacgc gcagaaaaaa aggatctcaa    6720
gaagatcctt tgatcttttc tacggggtct gacgctcagt ggaacgaaaa ctcacgttaa    6780
gggattttgg tcatgagatt atcaaaaagg atcttcacct agatcctttt aaattaaaaa    6840
tgaagtttta aatcaatcta agtatatat gagtaaactt ggtctgacag ttaccaatgc    6900
ttaatcagtg aggcacctat ctcagcgatc tgtctatttc gttcatccat agttgcctga    6960
ctccccgtcg tgtagataac tacgatacgg gagggcttac catctggccc cagtgctgca    7020
atgataccgc gagacccacg ctcaccggct ccagatttat cagcaataaa ccagccagcc    7080
ggaagggccg agcgcagaag tggtcctgca actttatccg cctccatcca gtctattaat    7140
tgttgccggg aagctagagt aagtagttcg ccagttaata gtttgcgcaa cgttgttgcc    7200
attgctacag gcatcgtggt gtcacgctcg tcgtttggta tggcttcatt cagctccggt    7260
tcccaacgat caaggcgagt tacatgatcc cccatgttgt gcaaaaaagc ggttagctcc    7320
ttcggtcctc cgatcgttgt cagaagtaag ttggccgcag tgttatcact catggttatg    7380
gcagcactgc ataattctct tactgtcatg ccatccgtaa gatgcttttc tgtgactggt    7440
gagtactcaa ccaagtcatt ctgagaatag tgtatgcggc gaccgagttg ctcttgcccg    7500
```

-continued

```
gcgtcaatac gggataatac cgcgccacat agcagaactt taaaagtgct catcattgga    7560
aaacgttctt cggggcgaaa actctcaagg atcttaccgc tgttgagatc cagttcgatg    7620
taacccactc gtgcacccaa ctgatcttca gcatctttta ctttcaccag cgtttctggg    7680
tgagcaaaaa caggaaggca aaatgccgca aaaaagggaa taagggcgac acggaaatgt    7740
tgaatactca tactcttcct ttttcaatat tattgaagca tttatcaggg ttattgtctc    7800
atgagcggat acatatttga atgtatttag aaaaataaac aatagggggt tccgcgcaca    7860
tttccccgaa aagtgccacc taaattgtaa gcgttaatat tttgttaaaa ttcgcgttaa    7920 attttttgtta aatcagctca ttttttaacc aataggccga atcggcaaa atcccttata    7980 aatcaaaaga atagaccgag atagggttga gtgttgttcc agtttggaac aagagtccac    8040
tattaaagaa cgtggactcc aacgtcaaag ggcgaaaaac cgtctatcag ggcgatggcc    8100
cactacgtga accatcaccc taatcaagtt ttttggggtc gaggtgccgt aaagcactaa    8160
atcggaaccc taaggggagc ccccgattta gagcttgacg gggaaagcca acctggctta    8220
tcgaaattaa tacgactcac tatagggaga ccggc                               8255
```

<210> SEQ ID NO 18
<211> LENGTH: 68
<212> TYPE: DNA
<213> ORGANISM: Artificial Sequence
<220> FEATURE:
<223> OTHER INFORMATION: translation initiation signal

<400> SEQUENCE: 18

```
aagcttccac catgggatgg agctgtatca tcctcttctt ggtagcaaca gctacaggtg    60
tccactcc                                                             68
```

<210> SEQ ID NO 19
<211> LENGTH: 7
<212> TYPE: PRT
<213> ORGANISM: Artificial Sequence
<220> FEATURE:
<223> OTHER INFORMATION: signal peptide

<400> SEQUENCE: 19

Ala Asn Asn Ala Thr Gly Pro
 1               5

<210> SEQ ID NO 20
<211> LENGTH: 20
<212> TYPE: PRT
<213> ORGANISM: Artificial Sequence
<220> FEATURE:
<223> OTHER INFORMATION: Linker

<400> SEQUENCE: 20

Gly Gly Gly Gly Ser Gly Gly Gly Gly Ser Gly Gly Gly Gly Ser Gly
 1               5                  10                  15

Gly Gly Gly Ser
            20

<210> SEQ ID NO 21
<211> LENGTH: 43
<212> TYPE: DNA
<213> ORGANISM: Artificial Sequence
<220> FEATURE:
<223> OTHER INFORMATION: oligonucleotide

```
<400> SEQUENCE: 21
gggggtggtg ggagcggtgg tggcggcagt ggcggcggcg gaa                    43

<210> SEQ ID NO 22
<211> LENGTH: 47
<212> TYPE: DNA
<213> ORGANISM: Artificial Sequence
<220> FEATURE:
<223> OTHER INFORMATION: oligonucleotide

<400> SEQUENCE: 22
ctagttccgc cgccgccact gccgccacca ccgctcccac cacccccc               47

<210> SEQ ID NO 23
<211> LENGTH: 38
<212> TYPE: DNA
<213> ORGANISM: Artificial Sequence
<220> FEATURE:
<223> OTHER INFORMATION: forward primer

<400> SEQUENCE: 23
ctcgaattcc accatggctt gcaattgtca gttgatgc                          38

<210> SEQ ID NO 24
<211> LENGTH: 30
<212> TYPE: DNA
<213> ORGANISM: Artificial Sequence
<220> FEATURE:
<223> OTHER INFORMATION: reverse primer

<400> SEQUENCE: 24
ctccccgggc ttgctatcag gagggtcttc                                   30

<210> SEQ ID NO 25
<211> LENGTH: 29
<212> TYPE: DNA
<213> ORGANISM: Artificial Sequence
<220> FEATURE:
<223> OTHER INFORMATION: forward primer

<400> SEQUENCE: 25
ctcactagtg aggtccagct tcagcagtc                                    29

<210> SEQ ID NO 26
<211> LENGTH: 44
<212> TYPE: DNA
<213> ORGANISM: Artificial Sequence
<220> FEATURE:
<223> OTHER INFORMATION: reverse primer

<400> SEQUENCE: 26
ctcgcggccg cttaccgttt gatttccagc ttggtgcctc cacc                   44

<210> SEQ ID NO 27
<211> LENGTH: 87
<212> TYPE: DNA
<213> ORGANISM: Artificial Sequence
<220> FEATURE:
<223> OTHER INFORMATION: oligonucleotide

<400> SEQUENCE: 27
ctagactcga gccaccatgg gatggagctg tatcatcctc ttcttggtag caacagctac  60
aggtgtccac tccgaggtcc agctgca                                      87
```

<210> SEQ ID NO 28
<211> LENGTH: 79
<212> TYPE: DNA
<213> ORGANISM: Artificial Sequence
<220> FEATURE:
<223> OTHER INFORMATION: oligonucleotide

<400> SEQUENCE: 28
gctggacctc ggagtggaca cctgtagctg ttgctaccaa gaagaggatg atacagctcc    60
atcccatggt ggctcgagt                                                 79

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
gtccagctgc agcagtctgg                                                20

<210> SEQ ID NO 30
<211> LENGTH: 22
<212> TYPE: DNA
<213> ORGANISM: Artificial Sequence
<220> FEATURE:
<223> OTHER INFORMATION: oligonucleotide

<400> SEQUENCE: 30
cgtttgattt caagcttggt gc                                             22

<210> SEQ ID NO 31
<211> LENGTH: 40
<212> TYPE: DNA
<213> ORGANISM: Artificial Sequence
<220> FEATURE:
<223> OTHER INFORMATION: oligonucleotide

<400> SEQUENCE: 31
gcgcaagctt gaaatcaaac gggcctccac caagggccca                          40

<210> SEQ ID NO 32
<211> LENGTH: 30
<212> TYPE: DNA
<213> ORGANISM: Artificial Sequence
<220> FEATURE:
<223> OTHER INFORMATION: oligonucleotide

<400> SEQUENCE: 32
gcgcctcgag tcatttaccc ggagacaggg                                     30

<210> SEQ ID NO 33
<211> LENGTH: 40
<212> TYPE: DNA
<213> ORGANISM: Artificial Sequence
<220> FEATURE:
<223> OTHER INFORMATION: oligonucleotide

<400> SEQUENCE: 33
gcgcaagctt gaaatcaaac gggcctccac acagagccca                          40

<210> SEQ ID NO 34
<211> LENGTH: 31
<212> TYPE: DNA
<213> ORGANISM: Artificial Sequence
<220> FEATURE:
<223> OTHER INFORMATION: oligonucleotide

<400> SEQUENCE: 34
gcgcctcgag tcatttaccg ggatttacag a                                    31

<210> SEQ ID NO 35
<211> LENGTH: 29
<212> TYPE: DNA
<213> ORGANISM: Artificial Sequence
<220> FEATURE:
<223> OTHER INFORMATION: oligonucleotide

<400> SEQUENCE: 35
ggactagtaa tagtgactct gaatgtccc                                        29

<210> SEQ ID NO 36
<211> LENGTH: 34
<212> TYPE: DNA
<213> ORGANISM: Artificial Sequence
<220> FEATURE:
<223> OTHER INFORMATION: oligonucleotide

<400> SEQUENCE: 36
attagcggcc gcttagcgca gttcccacca cttc                                  34

<210> SEQ ID NO 37
<211> LENGTH: 243
<212> TYPE: PRT
<213> ORGANISM: Artificial Sequence
<220> FEATURE:
<223> OTHER INFORMATION: mature secreted protein of 5T4 scFv,
      designated 5T4scFv.1

<400> SEQUENCE: 37

Glu Val Gln Leu Gln Gln Ser Gly Pro Asp Leu Val Lys Pro Gly Ala
 1               5                  10                  15

Ser Val Lys Ile Ser Cys Lys Ala Ser Gly Tyr Ser Phe Thr Gly Tyr
             20                  25                  30

Tyr Met His Trp Val Lys Gln Ser His Gly Lys Ser Leu Glu Trp Ile
         35                  40                  45

Gly Arg Ile Asn Pro Asn Asn Gly Val Thr Leu Tyr Asn Gln Lys Phe
     50                  55                  60

Lys Asp Lys Ala Ile Leu Thr Val Asp Lys Ser Thr Thr Ala Tyr
 65                  70                  75                  80

Met Glu Leu Arg Ser Leu Thr Ser Glu Asp Ser Ala Val Tyr Tyr Cys
                 85                  90                  95

Ala Arg Ser Thr Met Ile Thr Asn Tyr Val Met Asp Tyr Trp Gly Gln
            100                 105                 110

Val Thr Ser Val Thr Val Ser Ser Gly Gly Gly Gly Ser Gly Gly Gly
        115                 120                 125

Gly Thr Gly Gly Gly Gly Ser Ser Ile Val Met Thr Gln Thr Pro Thr
    130                 135                 140

Phe Leu Leu Val Ser Ala Gly Asp Arg Val Thr Ile Thr Cys Lys Ala
145                 150                 155                 160

Ser Gln Ser Val Ser Asn Asp Val Ala Trp Tyr Gln Gln Lys Pro Gly
                165                 170                 175

Gln Ser Pro Thr Leu Leu Ile Ser Tyr Thr Ser Ser Arg Tyr Ala Gly
            180                 185                 190

```
Val Pro Asp Arg Phe Ile Gly Ser Gly Tyr Gly Thr Asp Phe Thr Phe
        195                 200                 205

Thr Ile Ser Thr Leu Gln Ala Glu Asp Leu Ala Val Tyr Phe Cys Gln
        210                 215                 220

Gln Asp Tyr Asn Ser Pro Pro Thr Phe Gly Gly Gly Thr Lys Leu Glu
225                 230                 235                 240

Ile Lys Arg

<210> SEQ ID NO 38
<211> LENGTH: 600
<212> TYPE: PRT
<213> ORGANISM: Artificial Sequence
<220> FEATURE:
<223> OTHER INFORMATION: peptide of 5T4Sab1

<400> SEQUENCE: 38

Ala Ser Thr Met Gly Trp Ser Cys Ile Ile Leu Phe Leu Val Ala Thr
1               5                   10                  15

Ala Thr Gly Val His Ser Glu Val Gln Leu Gln Gln Ser Gly Pro Asp
            20                  25                  30

Leu Val Lys Pro Gly Ala Ser Val Lys Ile Ser Cys Lys Ala Ser Gly
        35                  40                  45

Tyr Ser Phe Thr Gly Tyr Tyr Met His Trp Val Lys Gln Ser His Gly
    50                  55                  60

Lys Ser Leu Glu Trp Ile Gly Arg Ile Asn Pro Asn Asn Gly Val Thr
65                  70                  75                  80

Leu Tyr Asn Gln Lys Phe Lys Asp Lys Ala Ile Leu Thr Val Asp Lys
                85                  90                  95

Ser Ser Thr Thr Ala Tyr Met Glu Leu Arg Ser Leu Thr Ser Glu Asp
            100                 105                 110

Ser Ala Val Tyr Tyr Cys Ala Arg Ser Thr Met Ile Thr Asn Tyr Val
        115                 120                 125

Met Asp Tyr Trp Gly Gln Val Thr Ser Val Thr Val Ser Ser Gly Gly
    130                 135                 140

Gly Gly Ser Gly Gly Gly Gly Thr Gly Gly Gly Gly Ser Ser Ile Val
145                 150                 155                 160

Met Thr Gln Thr Pro Thr Phe Leu Leu Val Ser Ala Gly Asp Arg Val
                165                 170                 175

Thr Ile Thr Cys Lys Ala Ser Gln Ser Val Ser Asn Asp Val Ala Trp
            180                 185                 190

Tyr Gln Gln Lys Pro Gly Gln Ser Pro Thr Leu Leu Ile Ser Tyr Thr
        195                 200                 205

Ser Ser Arg Tyr Ala Gly Val Pro Asp Arg Phe Ile Gly Ser Gly Tyr
    210                 215                 220

Gly Thr Asp Phe Thr Phe Thr Ile Ser Thr Leu Gln Ala Glu Asp Leu
225                 230                 235                 240

Ala Val Tyr Phe Cys Gln Gln Asp Tyr Asn Ser Pro Pro Thr Phe Gly
                245                 250                 255

Gly Gly Thr Lys Leu Glu Ile Lys Arg Ala Ser Thr Lys Gly Pro Ser
            260                 265                 270

Val Phe Pro Leu Ala Pro Ser Ser Lys Ser Thr Ser Gly Gly Thr Ala
        275                 280                 285

Ala Leu Gly Cys Leu Val Lys Asp Tyr Phe Pro Glu Pro Val Thr Val
    290                 295                 300
```

```
Ser Trp Asn Ser Gly Ala Leu Thr Ser Gly Val His Thr Phe Pro Ala
305                 310                 315                 320

Val Leu Gln Ser Ser Gly Leu Tyr Ser Leu Ser Ser Val Val Thr Val
                325                 330                 335

Pro Ser Ser Ser Leu Gly Thr Gln Thr Tyr Ile Cys Asn Val Asn His
            340                 345                 350

Lys Pro Ser Asn Thr Lys Val Asp Lys Lys Val Glu Pro Lys Ser Cys
        355                 360                 365

Asp Lys Thr His Thr Cys Pro Pro Cys Pro Ala Pro Glu Leu Leu Gly
    370                 375                 380

Gly Pro Ser Val Phe Leu Phe Pro Pro Lys Pro Lys Asp Thr Leu Met
385                 390                 395                 400

Ile Ser Arg Thr Pro Glu Val Thr Cys Val Val Val Asp Val Ser His
                405                 410                 415

Glu Asp Pro Glu Val Lys Phe Asn Trp Tyr Val Asp Gly Val Glu Val
            420                 425                 430

His Asn Ala Lys Thr Lys Pro Arg Glu Glu Gln Tyr Asn Ser Thr Tyr
        435                 440                 445

Arg Val Val Ser Val Leu Thr Val Leu His Gln Asp Trp Leu Asn Gly
    450                 455                 460

Lys Glu Tyr Lys Cys Lys Val Ser Asn Lys Ala Leu Pro Ala Pro Ile
465                 470                 475                 480

Glu Lys Thr Ile Ser Lys Ala Lys Gly Gln Pro Arg Glu Pro Gln Val
                485                 490                 495

Tyr Thr Leu Pro Pro Ser Arg Asp Glu Leu Thr Lys Asn Gln Val Ser
            500                 505                 510

Leu Thr Cys Leu Val Lys Gly Phe Tyr Pro Ser Asp Ile Ala Val Glu
        515                 520                 525

Trp Glu Ser Asn Gly Gln Pro Glu Asn Asn Tyr Lys Thr Thr Pro Pro
    530                 535                 540

Val Leu Asp Ser Asp Gly Ser Phe Phe Leu Tyr Ser Lys Leu Thr Val
545                 550                 555                 560

Asp Lys Ser Arg Trp Gln Gln Gly Asn Val Phe Ser Cys Ser Val Met
                565                 570                 575

His Glu Ala Leu His Asn His Tyr Thr Gln Lys Ser Leu Ser Leu Ser
            580                 585                 590

Pro Gly Lys Val Arg Arg Pro Ser
        595                 600

<210> SEQ ID NO 39
<211> LENGTH: 488
<212> TYPE: PRT
<213> ORGANISM: Artificial Sequence
<220> FEATURE:
<223> OTHER INFORMATION: peptide of B7-1.5T4.1

<400> SEQUENCE: 39

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60
```

```
Tyr Trp Gln Lys Glu Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Gly Gly Gly Gly Ser Glu Val Gln Leu Gln Gln Ser Gly Pro Asp
                245                 250                 255

Leu Val Lys Pro Gly Ala Ser Val Lys Ile Ser Cys Lys Ala Ser Gly
                260                 265                 270

Tyr Ser Phe Thr Gly Tyr Tyr Met His Trp Val Lys Gln Ser His Gly
            275                 280                 285

Lys Ser Leu Glu Trp Ile Gly Arg Ile Asn Pro Asn Asn Gly Val Thr
        290                 295                 300

Leu Tyr Asn Gln Lys Phe Lys Asp Lys Ala Ile Leu Thr Val Asp Lys
305                 310                 315                 320

Ser Ser Thr Thr Ala Tyr Met Glu Leu Arg Ser Leu Thr Ser Glu Asp
                325                 330                 335

Ser Ala Val Tyr Tyr Cys Ala Arg Ser Thr Met Ile Thr Asn Tyr Val
                340                 345                 350

Met Asp Tyr Trp Gly Gln Val Thr Ser Val Thr Val Ser Ser Gly Gly
            355                 360                 365

Gly Gly Ser Gly Gly Gly Gly Thr Gly Gly Gly Ser Ser Ile Val
        370                 375                 380

Met Thr Gln Thr Pro Thr Phe Leu Leu Val Ser Ala Gly Asp Arg Val
385                 390                 395                 400

Thr Ile Thr Cys Lys Ala Ser Gln Ser Val Ser Asn Asp Val Ala Trp
                405                 410                 415

Tyr Gln Gln Lys Pro Gly Gln Ser Pro Thr Leu Leu Ile Ser Tyr Thr
            420                 425                 430

Ser Ser Arg Tyr Ala Gly Val Pro Asp Arg Phe Ile Gly Ser Gly Tyr
        435                 440                 445

Gly Thr Asp Phe Thr Phe Thr Ile Ser Thr Leu Gln Ala Glu Asp Leu
450                 455                 460
```

-continued

```
Ala Val Tyr Phe Cys Gln Gln Asp Tyr Asn Ser Pro Pro Thr Phe Gly
465                 470                 475                 480

Gly Gly Thr Lys Leu Glu Ile Lys
                485

<210> SEQ ID NO 40
<211> LENGTH: 246
<212> TYPE: PRT
<213> ORGANISM: Homo sapiens

<400> SEQUENCE: 40

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
                20                  25                  30

Pro Cys Gln Phe Ala Asn Ser Gln Asn Gln Ser Leu Ser Glu Leu Val
            35                  40                  45

Val Phe Trp Gln Asp Gln Glu Asn Leu Val Leu Asn Glu Val Tyr Leu
        50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
210                 215                 220

Pro Phe Ser Ile Glu Leu Glu Asp Pro Gln Pro Pro Pro Asp His Ile
225                 230                 235                 240

Pro Gly Gly Gly Gly Ser
                245
```

VECTOR SYSTEM

CROSS-REFERENCE TO RELATED APPLICATIONS

This application is a continuation-in-part of U.S. patent application Ser. No. 10/060,585 filed 29 Jan. 2002, which is a continuation-in-part of U.S. patent application Ser. No. 09/445,375 filed Dec. 06 1999, which claims priority under 35 U.S.C. § 119 to Great Britain patent application number 9711579.4 filed 4 Jun. 1997, Great Britain patent application number 9713150.2 filed 20 Jun. 1997 and Great Britain patent application number 9714230.1 filed 4 Jul. 1997, and is a continuation-in-part of PCT No PCT/GB00/04317 filed 13 Nov. 2000 claiming priority from PCT/GB99/03859 and GB 0003527.9 and GB 0005071.65 designating inter alia the U.S. Each of these documents is incorporated herein by reference in its entirety.

FIELD OF THE INVENTION

The present invention is directed to a vector system. The vector system comprises a nucleotide sequence capable of encoding an antibody in vivo.

SUMMARY

According to a first aspect of the present invention there is provided a vector system comprising a nucleotide sequence ("NS") coding for an antibody. The vector system may be a non-viral system or a viral vector system. The vector system may also comprise a nucleotide sequence of interest ("NOI") which optionally encodes a protein of interest ("POI").

According to a second aspect of the present invention there is provided a method of treating and/or preventing a disease in a subject in need of same, the method comprising the step of administering a vector system according to the first aspect of the invention to the subject, such that the NS is expressed in vivo to produce said antibody.

According to a third aspect, the present invention also provides the use of a vector system according to the first aspect of the invention in the manufacture of a medicament to treat and/or prevent a disease in a subject in need of same, wherein the NS is expressed in vivo to produce said antibody. The disease may be a cancerous or non-cancerous disease. For cancerous diseases, the present invention also provides a method of delivering a nucleotide sequence of interest ("NOI") and/or a product of interest ("POI") to a tumor, which comprises the step of using a vector system according to the first aspect of the invention wherein the antibody is a tumor-interacting protein ("TIP").

According to a fourth aspect of the present invention there is provided a method of delivering to a target cell a retroviral vector, such as a lentiviral vector, comprising a nucleotide sequence of interest (NOI) encoding an antibody, where expression of the antibody is sustained at a level sufficient to elicit an immune response to the target cell. In a specific embodiment, the NOI encodes an antibody-polypeptide conjugate, where the polypeptide conjugated to the antibody elicits an immune response against the target cell or otherwise exerts a therapeutic effect upon the target cell. In this latter embodiment, the antibody may or may not elicit an antibody response.

BRIEF DESCRIPTION OF THE DRAWINGS

FIGS. 1A-1 to 1A-2 (SEQ ID NOS: 1 and 37)show a DNA sequence encoding a 5T4 scFv, designated 5T4scFv.1. The sequence of the mature secreted protein is given. FIGS. 1B-1-1B-4 (SEQ ID NOS: 2 and 38)show the cDNA sequence encoding 5T4Sab1. The sequence begins with a HindIII restriction site followed by a translation initiation signal and a signal peptide.

FIGS. 2A to 2C (SEQ ID NOS: 3 and 39)show the sequence of B7-1.5T4.1.

FIG. 3a shows the SCM B7-1.5T4.1 and FIG. 3b shows B7-1.5T4.2 in which the order of the co-stimulatory and tumor-binding domains are reversed. Sp=signal peptide; B7 ec=extracellular domain of B7-1; Vl=light chain variable domain of 5T4; Vh=heavy chain variable domain of 5T4.

FIGS. 4A to 4B (SEQ ID NOS: 4 and 40)show the sequence of the extracellular domain of human B7-2, including the signal peptide sequence. The mature protein begins at amino acid 17. The B7-2 derived sequence is followed by a flexible linker gly-gly-gly-gly-ser (Gly$_4$Ser) (Portion of SEQ ID NO: 40.)

FIG. 5 shows pKLink—the (Gly$_4$Ser)$_3$ (SEQ ID NO: 13) linker in pBluescript II SK (pBS II). The flexible linker is synthesized as two complementary oligonucleotides (SEQ ID NOS: 11 and 12) that are annealed to give restriction enzyme overhangs and then cloned as a double stranded oligonucleotide into pBSII. The amino acid translation of (Gly$_4$Ser)$_3$ (SEQ ID NO: 13) is shown in single letter code below the DNA sequence.

FIG. 6 shows anti-TNF alpha scFv in pBSII and subsequent addition of the leader sequence (SEQ ID NOS: 14 and 15).

FIG. 11 shows an immunostain of CT26-h5T4 tumors injected with Adlac z.

FIG. 12 illustrates an immunostain of CT26-h5T4 tumors injected with AdB7-scFv.

FIG. 13 (SEQ ID NO: 16) shows the nucleotide sequence of the SMART2 LscFvB7.1 5'cPPT plasmid. The nucleotide sequence of the scFvB7.1 insert subcloned from the bluescript plasmid is depicted as underlined text.

FIG. 14 (SEQ ID NO: 17) depicts the nucleotide sequence of the SMART2G5'cPPT plasmid, which was modified as described in Example 21 and resulted in the SMTscFvB7.1 plasmid.

DETAILED DESCRIPTION OF THE INVENTION

Vector Systems

Figure 3A:
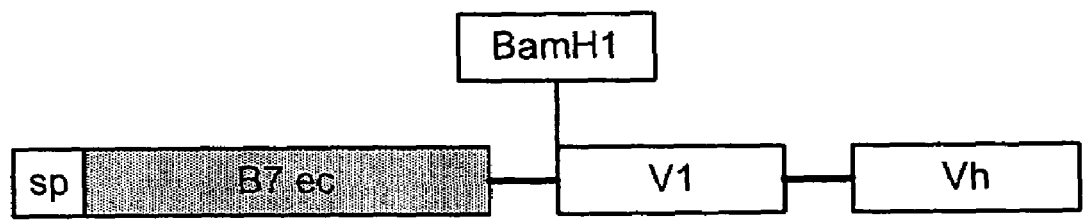
FIGS. 3a and 3b show a diagrammatic representation of two SCMs based on the B7-1 co-stimulatory domain.

The present invention relates to a vector system, in particular a vector system comprising a nucleotide sequence coding for an antibody.

As it is well known in the art, a vector is a tool that allows or facilitates the transfer of an entity from one environment to another. By way of example, some vectors used in recombinant DNA techniques allow entities—such as a segment of DNA (such as a such as a heterologous cDNA segment)—to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Gene therapy includes any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology (Ed Robert Meyers, Pub VCH, such as pages 556-558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favorable phenotype; cells can be manipulated at the molecular level to treat cancer (Schmidt-Wolf and Schmidt-Wolf, 1994, Annals of Hematology 69;273-279) or other conditions—such as immune, cardiovascular, neurological, inflammatory or infectious disorders; antigens can be manipulated and/or introduced to elicit an immune response—such as genetic vaccination.

The vector of the present invention may be a viral vector or a non-viral vector. In a first preferred embodiment, the vector is a non-viral vector. Non-viral delivery systems include but are not limited to DNA transfection methods. Here transfection includes a process using a non-viral vector to deliver a gene to a target mammalian cell. Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof. Viral delivery systems include but are not limited to adenovirus vector, an adeno-associated viral (AAV) vector, and a herpes viral vector, retroviral vector, lentiviral vector, baculoviral vector. Other examples of vectors include ex vivo delivery systems—which include but are not limited to DNA transfection methods such as electroporation, DNA biolistics, lipid-mediated transfection, and compacted DNA-mediated transfection).

In a second preferred embodiment the vector is a viral vector. Preferably the vector is a retroviral vector. In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In slightly more detail, a retrovirus is a virus which contains genomic RNA which on entry into a host cell is converted to a DNA molecule by a reverse transcriptase enzyme. The DNA copy serves as a template for the production of new RNA genomes and virally encoded proteins necessary for the assembly of infectious viral particles. Thus, a retrovirus is an infectious entity that replicates through a DNA intermediate.

There are many retroviruses and examples include: murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

For some applications, such as the delivery of antibodies for therapy, for example, cancer therapy, a preferred retroviral vector is a retroviral vector that integrates into the genome, for example, EIAV. Generally, these vectors are more stable than vectors that are episomal—such as Adenovirus. Although, the peak of expression may be higher with vectors that are episomal, advantageously, retroviral vectors that integrate may result in sustained expression over a period of time.

The phrase "sustained expression over a period of time" refers to the measurement of expression levels which are maintained at approximately the same meaningful level over a duration of time, the "duration of time" referring to at least up to 20 days, 30 days, 1 month, 40 days, 50 days, 60 days, or 2 months, for example. Meaningful levels of expression may be levels of expression that result in a quantitative diagnostic or therapeutic effect. For instance, a therapeutic effect may be the elicitation of an immune response to a target cell or may be the amelioration of one or more symptoms of a particular disease or disorder.

A detailed list of retroviruses may be found in Coffin et al ("Retroviruses" 1997 Cold Spring Harbor Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

All retroviruses contain three major coding domains, gag, pol, env, which code for essential virion proteins. Nevertheless, retroviruses may be broadly divided into two categories: namely, "simple" and "complex". These categories are distinguishable by the organization of their genomes. Simple retroviruses usually carry only this elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbor Laboratory Press Eds: J M Coffin, S M Hughes, H E Varmus pp 1-25).

All oncogenic members except the human T-cell leukemia virus-bovine leukemia virus group (HTLV-BLV) are simple retroviruses. HTLV, BLV and the lentiviruses and spumaviruses are complex. Some of the best studied oncogenic retroviruses are Rous sarcoma virus (RSV), mouse mammary tumor virus (MMTV) and murine leukemia virus (MLV) and the human T-cell leukemia virus (HTLV).

The vector system of the present invention may be a lentiviral vector system. The lentivirus group of retroviruses can be split into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992

EMBO.J 11; 3053-3058, Lewis and Emerman 1994 J. Virol. 68: 510-516). In contrast, other retroviruses—such as MLV—are unable to infect non-dividing cells such as those that make up, for example, muscle, brain, lung and liver tissue.

In one embodiment of the present invention, the features of adenoviruses may be combined with the genetic stability of retroviruses/lentiviruses which can be used to transduce target cells to become transient retroviral producer cells capable of stably infecting neighboring cells. Such retroviral producer cells which are engineered to express an antibody can be implanted in organisms such as animals or humans.

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems, such as those described for example in WO 95/30018.

The present invention also provides a hybrid viral vector system for in vivo delivery of a nucleotide sequence encoding an antibody, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on an adenoviral vector and/or the secondary viral vector is obtainable from or is based on a retroviral vector preferably a lentiviral vector.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called "budding".

As already indicated, each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For ease of understanding, a simple, generic diagram (not to scale) of a retroviral genome showing the elementary features of the LTRs, gag, pol and env is presented below.

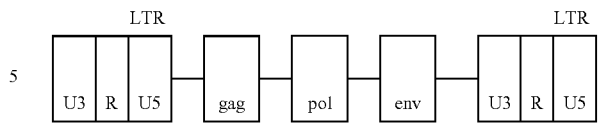

For the viral genome, the site of transcription initiation is at the boundary between U3 and R in the left hand side LTR (as shown above) and the site of poly (A) addition (termination) is at the boundary between R and U5 in the right hand side LTR (as shown above). U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

As shown in the diagram above, the basic molecular organization of a retroviral RNA genome is (5') R-U5-gag, pol, env- U3-R (3'). In a retroviral vector genome gag, pol and env are absent or not functional. The R regions at both ends of the RNA are repeated sequences. U5 and U3 represent sequences unique, respectively, to the 5' and 3' ends of the RNA genome. These three sets of end sequences go to form the long terminal repeats (LTRs) in the proviral DNA, which is the form of the genome which integrates into the genome of the infected cell. The LTRs in a wild type retrovirus consist of (5')U3-R-U5 (3'), and thus U3 and U5 both contain sequences which are important for proviral integration. Other essential sequences required in the genome for proper functioning include a primer binding site for first strand reverse transcription, a primer binding site for second strand reverse transcription and a packaging signal.

With regard to the structural genes gag, pol and env themselves and in slightly more detail, gag encodes the internal structural protein of the virus. Gag is proteolytically processed into the mature proteins MA (matrix), CA (capsid), NC (nucleocapsid). The gene pol encodes the reverse transcriptase (RT), which contains both DNA polymerase, and associated RNase H activities and integrase (IN), which mediates replication of the genome. The gene env encodes the surface (SU) glycoprotein and the transmembrane (TM) protein of the virion, which form a complex that interacts specifically with cellular receptor proteins. This interaction leads ultimately to fusion of the viral membrane with the cell membrane.

The envelope protein is a viral protein which coats the viral particle and plays an essential role in permitting viral entry into a target cell. The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesized in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they do play an essential role in the entry process. In this regard, the SU domain binds to a receptor molecule—often a specific receptor molecule—on the target cell. It is believed that this binding event activates the membrane fusion-inducing potential of the TM protein after which the viral and cell membranes fuse. In some viruses, notably MLV, a cleavage event—resulting in the removal of a short portion of the cytoplasmic tail of TM—is thought to play a key role in uncovering the full fusion activity of the protein (Brody et al 1994 J. Virol. 68: 4620-4627, Rein et al 1994 J. Virol. 68: 1773-1781). This cytoplasmic "tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. Here, transduction includes a process of using a viral vector to deliver a non-viral gene to a target cell. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an envelope protein with an erythropoietin segment produced a recombinant retrovirus which then bound specifically to human cells that expressed the erythropoietin receptor on their surface, such as red blood cell precursors (Maulik and Patel 1997 "Molecular Biotechnology: Therapeutic Applications and Strategies" 1997. Wiley-Liss Inc. pp 45.).

In addition to gag, pol and env, the complex retroviruses also contain "accessory" genes which code for accessory or auxiliary proteins. Accessory or auxiliary proteins are defined as those proteins encoded by the accessory genes in addition to those encoded by the usual replicative or structural genes, gag, pol and env. These accessory proteins are distinct from those involved in the regulation of gene expression, like those encoded by tat, rev, tax and rex. Examples of accessory genes include one or more of vif vpr, vpx, vpu and nef These accessory genes can be found in, for example, HIV (see, for example pages 802 and 803 of "Retroviruses" Ed. Coffin et al Pub. CSHL 1997). Non-essential accessory proteins may function in specialized cell types, providing functions that are at least in part duplicative of a function provided by a cellular protein. Typically, the accessory genes are located between pol and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral tat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (other wise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158:1-24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targeted cell or a targeted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to infect cells to introduce the NOI into the genome of the cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbor Laboratory Press Eds: J M Coffin, S M Hughes, H E Varmus pp 449). However, this technique can be problematic in the sense that the titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

More recently, packaging cells have been developed in which the gag, pol and env viral coding regions are carried on separate expression plasmids that are independently transfected into a packaging cell line so that three recombinant events are required for wild type viral production. This strategy is sometimes referred to as the three plasmid transfection method (Soneoka et al 1995 Nucl. Acids Res. 23: 628-633).

Transient transfection can also be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI. Vector production involves transient transfection of one or more of these components into cells containing the other required components. If the vector encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatitis virus (VSV). Insertion of the Env protein of VSV facilitates vector concentration as HIV/VSV-G vectors with titres of $5 \times 10^5$ ($10^8$ after concentration) were generated by transient transfection (Naldini et al 1996 Science 272: 263-267). Thus, transient transfection of HIV vectors may provide a useful strategy for the generation of high titre vectors (Yee et al 1994 PNAS. 91: 9564-9568).

If the retroviral component includes an env nucleotide sequence, then all or part of that sequence can be optionally replaced with all or part of another env nucleotide sequence. Replacement of the env gene with a heterologous env gene is an example of a technique or strategy called pseudotyping. Pseudotyping is not a new phenomenon and examples may be found in WO-A-98/05759, WO-A-98/05754, WO-A-97/17457, WO-A-96/09400, WO-A-91/00047 and Mebatsion et al 1997 Cell 90, 841-847.

Pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389:239-242). By way of example—workers have pseudotyped an HIV based vector with the glycoprotein from VSV (Verma and Somia 1997 ibid). Alternatively, env can be modified so as to affect (such as to alter) its specificity.

Thus, the term "recombinant retroviral vector" describes an entity (such as a DNA molecule) which contains sufficient retroviral sequences to allow an RNA transcript of the vector to be packaged in the presence of essential retroviral proteins into a retroviral particle capable of infecting a target cell. Infection of the target cell includes reverse transcription and integration into the target cell genome.

The term "recombinant retroviral vector" also covers a retroviral particle containing an RNA genome encoded by the DNA molecule. The retroviral vector will also contain non-viral genes which are to be delivered by the vector to the target cell. A recombinant retroviral vector is incapable of independent replication to produce infectious retroviral particles. Usually, a recombinant retroviral vector lacks functional gag-pol and/or env genes, or other genes encoding proteins essential for replication.

The term "targeted retroviral vector" means a recombinant retroviral vector whose ability to infect a cell or to be expressed in the target cell is restricted to certain cell types within the host organism. An example of targeted retroviral vectors is one with a genetically modified envelope protein which binds to cell surface molecules found only on a limited number of cell types in the host organism. Another example of a targeted retroviral vector is one which contains promoter and/or enhancer elements which permit-expression of one or more retroviral transcripts in only a proportion of the cell types of the host organism.

NS/NOI

The vector system of the present invention comprises a nucleotide sequence ("NS") coding for an antibody. The system may also comprise a nucleotide of Interest ("NOI") which may optionally encode a protein of interest ("POI")

On occasions in the following text, the NS and NOI may be individually or collectively referred to as being a gene.

The NS and NOI can be any suitable nucleotide sequence. For example, the NOI can be, for example, a synthetic DNA or RNA sequence, a natural DNA or RNA sequence, a recombinant DNA or RNA sequence (i.e. prepared by use of recombinant DNA techniques), a cDNA sequence or a partial genomic DNA sequence, including combinations thereof. The NOI may be a sense sequence or an antisense sequence.

There may be a plurality of NSs or NOIs, which may be directly or indirectly joined to each other, or combinations thereof. Thus, the expressed product may have two or more effector domains (which may be the same or different) and/or two or more "antibody" domains (which may be the same or different).

The NS encodes an antibody (see below).

The NOI may encode a protein of interest ("POI"). In this way, the vector system could be used to examine the effect of expression of a foreign gene on the target cells (such as a tumor cell). By way of example, the vector system could be used to screen a cDNA library for a particular effect on specific tumor cells. Alternatively the POI may have therapeutic, diagnostic, selection, and/or marker properties (see below).

The POIs may be proteins which are secreted from the cell. Alternatively the NOI expression products may not be secreted and may be active within the cell. For some applications, it is preferred for the NOI expression product to demonstrate a bystander effect or a distant bystander effect; that is the production of the expression product in one cell leading to the modulation of additional, related cells, either neighboring or distant (e.g. metastatic), which possess a common phenotype.

The NOI or a sequence derived from the NOI may be capable of blocking or inhibiting the expression of a gene in the target cell. For example, the NOI may be an antisense sequence or an siRNA. The inhibition of gene expression using antisense technology is well known in the art.

Post-transcriptional gene silencing (PTGS) mediated by double-stranded RNA (dsRNA) is a conserved cellular defense mechanism for controlling the expression of foreign genes. It is thought that the random integration of elements such as transposons or viruses causes the expression of dsRNA, which activates sequence-specific degradation of homologous single-stranded mRNA or viral genomic RNA. The silencing effect is known as RNA interference (RNAi). The mechanism of RNAi involves the processing of long dsRNAs into duplexes of 21-25 nucleotide (nt) RNAs. These products are called small interfering or silencing RNAs (siRNAs) which are the sequence-specific mediators of mRNA degradation. In differentiated mammalian cells dsRNA>30 bp has been found to activate the interferon response leading to shut-down of protein synthesis and non-specific mRNA degradation. However this response can be bypassed by using 21 nt siRNA duplexes allowing gene function to be analysed in cultured mammalian cells.

The NOI or a sequence derived from the NOI may encode one or more suicide genes. A number of suicide gene systems have been identified, including, but not limited to, the herpes simplex virus thymidine kinase gene, the cytosine deaminase gene, the varicella-zoster virus thymidine kinase gene, the nitroreductase gene, the *Escherichia coli* gpt gene, and the *E. coli* Deo gene. Suicide genes in cancer therapy have been reviewed in, for example, *World J Surg* 2002 July;26(7):783-9, Adv Exp Med Biol 2000;465:411-22 and Semin Oncol. 1996 February;23(1):31-45.

The NOI or a sequence derived from the NOIs may be capable of "knocking out" the expression of a particular gene in the target cell (for example, a tumor cell). There are several "knock out" strategies known in the art. For example, the NOI may be capable of integrating in the genome of the target cell so as to disrupt expression of the particular gene. The NOI may disrupt expression by, for example, introducing a premature stop codon, by rendering the downstream coding sequence out of frame, or by affecting the capacity of the encoded protein to fold (thereby affecting its function).

Included in the scope of the invention are oligonucleotide sequences, anti-sense RNA and DNA molecules and ribozymes, which function to destabilise the mRNA or inhibit translation of gene of interest. Such nucleotide sequences may be used in conditions where it would be preferable to decrease gene of interest's nucleotide and protein levels, such as in breast cancer (BRACA genes), Burkitt's Lymphoma (c-myc), colon cancer (tumor suppressor deleted in colon cancer (DCC)) (Huerta et al., 2001, Dig Dis Sci, 46, 1884-91) and others.

The vector system of the present invention could be used to flood target cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication or integration elements are integrated into the NOI (such as lentivirus derived LTR sequences and Adeno Associated Virus IR sequences.

Modifications of gene expression can be obtained by designing anti-sense sequences to the control regions of, for example, tumor specific target genes, such as the promoters, enhancers, and introns.

Oligonucleotides derived from the transcription initiation site, e.g., between −10 and +10 regions of the leader sequence, are preferred. Anti-sense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Alternatively, the NOI may be capable of enhancing or inducing ectopic expression of a gene in a target cell. The NOI or a sequence derived therefrom may be capable of "knocking in" the expression of a particular gene.

Transfected target cells which express a particular gene, or which lack the expression of a particular gene have applications in drug discovery and target validation. The expression system could be used to determine which genes have a desirable effect on target tumor cells, such as those genes or proteins which are able to trigger apoptosis in the cells. Equally, if the inhibition or blocking of expression of a particular gene is found to have a cytotoxic effect on the target tumor cell, this may open up possible therapeutic strategies which ensure that expression of the gene is not lost.

An NOI delivered by the vector system may be used for selection or marker purposes. For example, the NOI may encode for a selection gene, or a marker gene. Many different selectable markers are known in the art and include, but are not limited to, the bacterial neomycin and hygromycin phosphotransferase genes which confer resistance to G418 and hygromycin respectively; a mutant mouse dihydrofolate reductase gene which confers resistance to methotrexate; the bacterial gpt gene which allows cells to grow in medium containing mycophenolic acid, xanthine and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow chemical selection of most cells expressing these genes.

The NOI delivered by the vector system may be a therapeutic gene—in the sense that the gene itself may be capable of eliciting a therapeutic effect or it may code for a product that is capable of eliciting a therapeutic effect. In a highly preferred aspect of the present invention, the NOI encodes for an anti-tumor agent. The vector system may be administered systemically and result in sustained expression of the NOI.

The NOI may be or encode a palliative agent, i.e. a compound which may provides relief, but not a cure.

In one preferred embodiment, the NOI is capable of encoding a cytotoxic molecule. In particular, the NOI(s) may encode molecules which enhance target cells to perish or which stimulate re-generation and functional recovery in the damaged tissue. In another preferred embodiment, the NOI is capable of encoding an enzyme or enzymes responsible for converting a pro-drug into its active metabolite.

In accordance with the present invention, suitable NOIs include those that are (or can produce entities) of therapeutic and/or diagnostic application such as, but not limited to: cytokines, chemokines, hormones, antibodies, engineered immunoglobulin-like molecules, a single chain antibody, fusion proteins, enzymes, immune co-stimulatory molecules, immunomodulatory molecules, anti-sense RNA, a trans-dominant negative mutant of a target protein, a toxin, a conditional toxin, an antigen, a tumor suppresser protein and growth factors, membrane proteins, vasoactive proteins and peptides, anti-viral proteins and ribozymes, and derivatives thereof (such as with an associated reporter group).

The term "enzyme" as used herein means a reaction catalyzing substance modulating but not limited to protein or polypeptide or a fragment of such protein or polypeptide.

The NOI may also be or encode an anti-apoptotic factor or a neuroprotective molecule. The survival of cells during programmed cell death depends critically on their ability to access "trophic" molecular signals derived primarily from interactions with other cells. For example, the NOI may encode a pro-apoptotic gene such as p53 or it may be a gene involved in control of the cell death cascade (such as Bcl-2).

The NOI may be a ribozyme. Ribozymes are enzymatic RNA molecules capable of catalyzing the specific cleavage of RNA.

Suitable NOIs for use in the treatment or prevention of ischemic heart disease include NOIs encoding plasminogen activators. Suitable NOIs for the treatment or prevention of rheumatoid arthritis or cerebral malaria include genes encoding anti-inflammatory proteins, antibodies directed against tumor necrosis factor (TNF) alpha, and anti-adhesion molecules (such as antibody molecules or receptors specific for adhesion molecules). Examples of hypoxia regulatable therapeutic NOIs can be found in PCT/GB95/00322 (WO-A-9521927).

In addition to the therapeutic gene or genes and the expression regulatory elements described, the delivery system may contain additional genetic elements for the efficient or regulated expression of the gene or genes, including promoters/enhancers, translation initiation signals, internal ribosome entry sites (IRES), splicing and polyadenylation signals.

The NOI or NOIs may be under the expression control of an expression regulatory element, usually a promoter or a promoter and enhancer. The enhancer and/or promoter may be preferentially active in a hypoxic or ischemic or low glucose environment, such that the NOI is preferentially expressed in the particular tissues of interest, such as in the environment of a tumor, arthritic joint or other sites of ischemia. Thus any significant biological effect or deleterious effect of the NOI on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof. Further examples include respiratory airway epithelial cells, hepatocytes, muscle cells, cardiac myocytes, synoviocytes, primary mammary epithelial cells and post-mitotically terminally differentiated non-replicating cells such as macrophages and neurons.

The term "promoter" is used in the normal sense of the art, e.g an RNA polymerase binding site in the Jacob-Monod theory of gene expression. The term "enhancer" includes a DNA sequence which binds to other protein components of the transcription initiation complex and thus facilitates the initiation of transcription directed by its associated promoter. The promoter and enhancer of the transcription units encoding the secondary delivery system are preferably strongly active, or capable of being strongly induced, in the primary target cells under conditions for production of the secondary delivery system. The promoter and/or enhancer may be constitutively efficient, or may be tissue or temporally restricted in their activity. Examples of temporally restricted promoters/enhancers are those which are responsive to ischemia and/or hypoxia, such as hypoxia response elements or the promoter/enhancer of a grp78 or a grp94 gene. One preferred promoter-enhancer combination is a human cytomegalovirus (hCMV) major immediate early (MIE) promoter/enhancer combination.

Preferably the promoters of the present invention are tissue specific. That is, they are capable of driving transcription of a NOI or NOI(s) in one tissue while remaining largely "silent" in other tissue types. The term "tissue specific" means a promoter which is not restricted in activity to a single tissue type but which nevertheless shows selectivity in that they may be active in one group of tissues and less active or silent in another group. The level of expression of an NOI or NOIs under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity.

A number of tissue specific promoters, described above, may be particularly advantageous in practicing the present invention. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Promoters suitable for cardiac-specific expression include the promoter from the murine cardiac α-myosin heavy chain (MHC) gene. Suitable vascular endothelium-specific promoters include the Et-1 promoter and von Willebrand factor promoter. Prostate specific promoters include the 5' flanking region of the human glandular kallikrein-1 (hKLK2) gene and the prostate specific antigen (hKLK3). Examples of promoters/enhancers which are cell specific include a macrophage-specific promoter or enhancer, such as CSF-1 promoter-enhancer, or elements from a mannose receptor gene promoter-enhancer (Rouleux et al 1994 Exp Cell Res 214: 113-119). Alternatively, promoter or enhancer elements which are preferentially active in neutrophils, or a lymphocyte-specific enhancer such as an IL-2 gene enhancer, may be used.

The vector system of the present invention may deliver the NS and/or NOI to a target cell. The target cell may be any host cell capable of expressing the antibody in vivo (or ex vivo). The target cell may also be capable of expressing the POI, or the NOI may be delivered to another cell for POI expression.

Where the antibody and/or NOI and/or POI exerts an effect (such as a therapeutic effect) this may be on the target cell. Alternatively the antibody and/or NOI and/or POI may exert an effect on a different cell. The target cell may act as an in situ factory for production of the antibody and/or NOI and/or POI. The target cell may be a tumor cell. The target cell may be a precursor cell such as a hematopoietic (preferably myeloid hematopoietic) cell of the monocyte-macrophage lineage or a precursor of such cells such as a CD34-positive stem cell.

Antibodies

The vector system of the present invention comprises a nucleotide sequence that encodes an antibody. The nucleotide sequence may be incorporated into a retroviral plasmid or lentiviral plasmid and may be delivered in vitro or in vivo by a viral vector for sustained expression of the antibody encoded by the nucleotide sequence. In certain embodiments, the antibody is conjugated to another polypeptide, such as a co-stimulatory molecule or an effector domain, and the conjugate is expressed over a period of time. In these latter described embodiments, the antibody of the conjugate may direct the conjugate to a target cell and the polypeptide in the conjugate may induce an immune response or any other type of therapeutic response against the target cell, as described hereafter.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies. In specific embodiments, nucleic acid sequences encoding any of the antibodies disclosed in U.S. application Ser. No. 09/341,894 (Piechaczyk et al.) and WO 94/29446 may be expressed.

The term "mimetic" relates to any chemical which may be a peptide, polypeptide, antibody or other organic chemical which has the same binding specificity as the antibody. The term "derivative" as used herein includes chemical modification of an antibody. Illustrative of such modifications would be replacement of hydrogen by an alkyl, acyl, or amino group.

A whole immunoglobulin molecule is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favorable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portion of the heavy and light chains. Each antibody domain consists of seven anti-parallel β-sheets forming a β-barrel with loops connecting the β-strands. Among the loops are the CDR regions. It is feasible to more the CDRs and their associated specificity from one scaffolding β-barrel to another. This is called CDR-grafting. CDR-grafted antibodies appear in early clinical studies not to be as strongly immunogenic as either mouse or chimeric antibodies. Moreover, mutations may be made outside the CDR in order to increase the binding activity thereof, as in so-called humanized antibodies.

Fab, Fv, and single chain Fv (ScFv) fragments with VH and VL joined by a polypeptide linker exhibit specificities and affinities for antigen similar to the original monoclonal antibodies. The ScFv fusion proteins can be produced with a non-antibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanized domains.

A large number of monoclonal antibodies and immunoglobulin-like molecules are known which bind specifically to antigens present on the surfaces of particular cell types. Procedures for identifying, characterizing, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The antibody used in the present invention may be derived from a human antibody or an engineered, humanized rodent antibody such as a CDR-grafted antibody or may be derived from a phage-display library. The antigen-binding domain may be comprised of the heavy and light chains of an immunoglobulin, expressed from separate genes, or may use the light chain of an immunoglobulin and a truncated heavy chain to form a Fab or a F(ab)'2 fragment. Alternatively, truncated forms of both heavy and light chains may be used which assemble to form a Fv fragment. An engineered scFv fragment may also be used, in which case, only a single gene is required to encode the antigen-binding domain. In one preferred aspect, the antigen-binding domain is formed from a Fv or a scFv.

As is well known, antibodies play a key role in the immune system. In brief, the immune system works in three fundamentally different ways: by humoral immunity, by cellular immunity and by secretion of stimulatory proteins, called lymphokines. Humoral immunity relies on proteins collectively called immunoglobulin which constitute about 20% of the proteins in the blood. A single immunoglobulin molecule is called an antibody but "antibody" is also used to mean many different molecules all directed against the same target molecule. Humoral immunity also involves complement, a set of proteins that are activated to kill bacteria both non-specifically and in conjunction with antibody.

In cellular immunity, intact cells are responsible for recognition and elimination reactions. The body's first line of defense is the recognition and killing of microorganisms by phagocytes, cells specialized for the ingestion and digestion of unwanted material. These cells include neutrophils and macrophages. A key role of antibodies is to help phagocytes recognize and destroy foreign materials.

In order to perform these functions, the antibody is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H (VH) and L (VL) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favorable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Monoclonal antibodies are homogenous antibodies of the same antigenic specificity representing the product of a single clone of antibody-producing cells. It was recognized that monoclonal antibodies offered the basis for human therapeutic products. However, although mouse antibodies are similar to human antibodies, they are sufficiently different that they are recognized by the immune system as foreign bodies, thereby giving rise to an immunological response. This human-anti-mouse-antibody (HAMA) response limits the usefulness of mouse antibodies as human therapeutic products.

In virally directed enzyme therapy (VDEPT), a foreign gene is delivered to normal and cancerous cells by a viral vector—such as a retroviral vector. The foreign gene codes for an enzyme that can convert a non-toxic prodrug (e.g. 5-fluorocytosine) to a toxic metabolite (5-fluorouracil) that will kill those cells making it (Sikora et al 1994 Ann New York Acad Sci 71b: 115-124). If the promoter utilized is tumor specific, then the toxic product will only be synthesized in the tumor cells. Studies in animal models have demonstrated that this type of treatment can deliver up to 50-fold more drug than by conventional means (Connors and Knox 1995 1995 Stem Cells 13: 501-511). A variation of this technique uses tumor associated antibodies conjugated to prodrug converting enzymes to provide specific delivery to tumors. This method is referred to as antibody-directed enzyme prodrug therapy (ADEPT) (Maulik S and Patel S D "Molecular Biotechnology" 1997 Wiley-Liss Inc pp 45).

A large number of monoclonal antibodies and immunoglobulin-like molecules are known which bind specifically to antigens present on the surfaces of particular cell types such as tumor cells. Procedures for identifying, characterizing, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells. The immunoglobulin or immunoglobulin-like molecule may be derived from a human antibody or an engineered, humanized rodent antibody such as a CDR-grafted antibody or may be derived from a phage-display library or may be a synthetic immunoglobulin-like molecule.

When a pathogen invades the body, lymphocytes respond with three types of reaction. The lymphocytes of the humoral system (B cells) secrete antibodies that can bind to the pathogen, signaling its degradation by macrophages and other cells. The lymphocytes of the cellular system (T cells) carry out two major types of functions. Cytotoxic T lymphocytes (CTLs) develop the ability to directly recognize and kill the cells infected by the pathogen. Helper T cells (TH cells) independently recognize the pathogen and secrete protein factors (lymphokines) that stimulate growth and responsiveness of B cells, T cells, and macrophages, thus greatly strengthening the power of the immune response.

In a preferred embodiment, the antibody comprises IgG and/or IgE, or a part thereof, or a bioisostere thereof. In a more preferred embodiment, the antibody comprises IgG, or a part thereof, or a bioisostere thereof.

Preferably the antibody recognizes a trophoblast cell surface antigen. Preferably the antibody recognizes the 5T4 antigen. The trophoblast cell surface antigen, originally defined by monoclonal antibody 5T4 (Hole & Stern 1988 Br. J Cancer 57; 239-246), is expressed at high levels on the cells of a wide variety of human carcinomas (Myers et al. 1994 J. Biol. Chem. 269; 9319-9324) but, in normal tissues of non-pregnant individuals, is essentially restricted to low level expression on a few specialized epithelia (Myers et al. ibid. and references therein). Antibody fragments that bind to the antigen are further described in Myers et al., Cancer Gene Therapy 9: 884-896 (2002) and in WO 98/55607. The 5T4 antigen has been implicated in contributing to the development of metastatic potential and therefore antibodies specifically recognizing this molecule may have clinical relevance in the treatment of tumors expressing the antigen. For example, following systemic administration of vectors encoding scFV specific to 5T4, scFV protein is present in 5T4 positive tumors indicating that 5T4 is a suitable target for antibody-mediated therapy. In particular, a relatively high and sustained level of secreted scFV protein is observed following lentiviral vector delivery of 5T4 scFV in vivo. See Example 22. This observation is surprising given the little information reported on gene expression following systemic administration of lentiviral vectors, such as EIAV, in vivo.

The variable region of the 5T4 monoclonal antibody can also be humanized by a number of techniques, which are known in the art, including grafting of the CDR region sequences on to a human backbone. These can then be used to construct an intact humanized antibody or a humanized single chain antibody (Sab), such as an ScFv coupled to an Fc region (see Antibody Engineering: a practical approach, Ed McCafferty et al. 1996 OUP).

Here the term Sab is not limited to just a human or a humanized single chain antibody. Preferably, however the Sab is a human single chain antibody or a humanized single chain antibody, or part thereof—such as ScFv coupled to an Fc region.

In accordance with the invention, standard molecular biology techniques may be used which are within the level of skill in the art. Such techniques are fully described in the literature. See for example; Sambrook et al. (1989) Molecular Cloning; a laboratory manual; Hames and Glover (1985-1997) DNA Cloning: a practical approach, Volumes I-IV (second edition). Methods for the engineering of immunoglobulin genes in particular are given in McCafferty et al (1996) Antibody engineering: a practical approach. The antibody or antibody conjugate may be expressed for any duration of time. In specific embodiments, the anitbody or antibody conjugate is expressed for about 10 days or more, 15 days or more, 20 days or more, 25 days or more, 30 days or more, 35 days or more, 40 days or more, 45 days or more, 50 days or more, 55 days or more, or 60 days or more, or for 1 month or more or 2 months or more.

Diseases

The delivery of one or more one or more therapeutic genes by a delivery system according to the present invention may be used alone or in combination with other treatments or components of the treatment. For example, the delivery system of the present invention may be used to deliver one or more NOI(s) useful in the treatment of the disorders listed in WO-A-98/05635. For ease of reference, part of that list is now provided: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumor growth, invasion and spread, angiogenesis, metastases, malignant, ascites and malignant pleural effusion; cerebral ischemia, ischemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the delivery system of the present invention may be used to deliver one or more NOI(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumor immunity); regulation of hematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilizing specific cell types to sites of injury or infection); homeostatic and thrombolytic activity (e.g for treating hemophilia and stroke); anti-inflammatory activity (for treating e.g. septic shock or Crohn's disease); as anti-microbials; modulators of e.g. metabolism or behavior; as analgesics; treating specific deficiency disorders; in treatment of e.g. psoriasis, in human or veterinary medicine.

In addition, or in the alternative, the delivery system of the present invention may be used to deliver one or more NOI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosis, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chorea, myasthenia gravis, pseudo-tumor cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The subject treated by the method of the present invention may be a human or animal subject. Preferably the subject is a mammalian subject, more preferably a human subject. In one embodiment of the present invention, the disease to be treated is not cancer. In another embodiment of the present invention, the disease to be treated is not a virally caused disease.

Tumours

In another embodiment, the disease is a cancer. The vector system may also comprise an NOI, optionally encoding a POI. In use the vector system may be capable of delivering the NOI and/or the POI to the interior of a tumor mass. Preferably in use the vector system is capable of delivering an NOI and/or POI to a selective tumor site. In addition to cancerous cells, the cell types present within a tumor mass include but are not limited to macrophages, lymphocytes, tumor infiltrating lymphocytes, endothelial cells, and others.

The NOI often encodes an antibody, and preferably, the antibody recognizes a tumor. The antibody may be a tumor interacting protein, i.e. specific for a tumor. The antibody may be able to bind specifically to a tumor, and be a tumor binding protein. Preferably the antibody is capable of interacting specifically with at least one tumor associated cell surface molecule.

The POI may also comprise at least one tumor-binding domain capable of interacting with at least one tumor associated cell surface molecule ("TACSM"). In accordance with the present invention the TACSM can include but is not limited to a cell surface molecule which plays a role in tumor cell growth, migration or metastasis, a receptor for adhesive proteins such as the integrin vitronectin receptor, a growth factor receptor (such as epidermal growth factor (EGF) receptor, platelet-derived growth factor (PDGF) receptor, fibroblast-derived growth factor (FDGF) receptor, nerve growth factor receptor, insulin-like growth factor (IGF-1) receptor; a plasminogen activator; a metalloproteinase (such as collagenase) 5T4 antigen; a tumor specific carbohydrate moiety; an oncofetal antigen; a mucin; a growth factor receptor; a glycoprotein; and an antigen restricted in its tissue distribution. Preferably the TACSM is selectively expressed on one cell type or on a restrictive number of cell types.

Examples of a tumor binding protein (TBP) include: an adhesion molecule such as Intercellular adhesion molecule, ICAM-1, ICAM-2, LFA-1, LFA-2, LFA-3, LECAM-1, VLA-4, ELAM, N-CAM, N-cadherin, P-Selectin, CD44 and its variant isoforms (in particular CD44v6, CD44v7-8), CD56; a growth factor receptor ligand such epidermal growth factor (EGF), Platelet-derived growth factor (PDGF), Fibroblast-derived growth factor (FDGF), Nerve growth factor, vasopressin, insulin, insulin-like growth factor (IGF-1), hepatocyte growth factor, nerve growth factor, human growth factor, brain derived growth factor, ciliary neurotrophic factor, glial cell line-derived growth factor; heavy and light chain sequences from an immunoglobulin (Ig) variable region (from human and animal sources), engineered antibody or one from a phage display library. A phage display library is a technique of expressing immunoglobulin genes in bacteriophage has been developed as a means for obtaining antibodies with the desired binding specificities. Expression systems, based on bacteriophage lambda, and more recently filamentous phage have been developed. The bacteriophage expression systems can be designed to allow heavy and light chains to form random combinations which are tested for their ability to bind the desired antigen.

The TBP may contain an effector domain which is activated on binding of the TPB to the TASCM. The effector domain or domains may be activated on binding of the TBP to a TASCM leading to inhibition of tumor cell proliferation, survival or dissemination. The effector domain may possess enzymatic activity (such as a pro-drug activating enzyme) or the effector domain may include a toxin, or an immune enhancer, such as a cytokine/lymphokine such as those listed above.

Preferably the TBP comprises one or more binding domains capable of interacting with one or more TACSMs which are present on the cancerous cells—which TACSMs may be the same or different.

The term "interacting" includes direct binding, leading to a biological effect as a result of such binding.

Preferably the vector system is used to deliver the antibody and/or an NOI and/or POI ex vivo and/or in vivo to a tumor. The vector system of the present invention is useful in gene therapy for delivering the antibody and/or an NOI and/or POI to a selective site.

In a preferred aspect, the present invention relates to the delivery of TBP—encoding genes to the site of a tumor. This has considerable advantages for medical applications (such as therapeutic applications) in which TBPs are indicated since it circumvents a number of problems associated with delivery of proteins systemically in humans.

In contrast to the problems associated with production and delivery of proteins, the methods of the invention allow the delivery of genes to the site of the tumor, thus circumventing a number of production problems. The TBPs are thereby produced in situ in the autologous human cells, which serve as a local factory for the production of the gene-based medicament (such as a therapeutic). This has significant advantages in minimizing systemic toxicity. The activity of the protein is maximal since the glycosylation of the protein shows a human pattern appropriate to the individual being treated.

The methods of the invention can be used in conjunction with direct injection into the site of the tumor or systemic delivery of, for example targeted vectors or engineered hematopoietic (preferably myeloid hematopoietic) cells or their progenitors. Systemic delivery may be particularly advantageous in a number of indications, particularly in the treatment of disseminated disease. In these cases the gene delivery system or engineered cells can be administered intravenously by bolus injection or by infusion in a suitable formulation. A pharmaceutically acceptable formulation may include an isotonic saline solution, a buffered saline solution or a tissue-culture medium. Additional formulatory agents may be included such as preservative or stabilizing agents.

Costimulatory Molecules

Lymphocytes require at least two distinct signals in order to respond to antigens by activation of effector functions (Bretscher and Cohn 1970 Science 169: 1042-1049; Crabtree 1989 Science 243: 355-361). The primary signal is specific for antigen. For B-lymphocytes, the B-cell antigen receptor (surface immunoglobulin) recognizes three-dimensional epitopes on a variety of macromolecules. For T-lymphocytes, the T-cell receptor (TCR) recognizes peptide antigens displayed on the surface of antigen-presenting cells by proteins of the major histocompatibility (MHC) family (Weiss et al. 1986 Ann. Rev. Immunol. 4: 593-619).

Stimulation of the primary signal in isolation normally leads to apoptosis (programmed cell death) of the lymphocyte or leads to the establishment of a state of sustained unresponsiveness or anergy (Weiss et al. supra). In order to achieve activation of the lymphocyte, accessory signals are required which may be delivered by cytokines or by cell-surface co-stimulatory ligands present on antigen-presenting cells (APC).

There are a number of such co-stimulatory molecules now identified including adhesion molecules, LFA-3, ICAM-1, ICAM-2. Major co-stimulatory molecules present on APC are the members of the B7 family including B7-1 (CD80), B7-2 (CD86) and B7-3. These molecules are ligands of co-stimulatory receptors on lymphocytes including CD28 (WO92/00092), probably the most significant co-stimulatory receptor for resting T-cells. Different members of the B7 family of glycoproteins may deliver subtly different signals to T-cells(Nunesetal. 1996J. Biol. Chem. 271: 1591-1598).

Established tumors, despite the fact that they commonly express unusual antigens on their surfaces, are poorly immunogenic. It has been postulated previously that one method for stimulating immune recognition of tumor cells would be to enhance antigen presentation and co-stimulation of lymphocytes in the context of tumor antigens. Transfection of the genes encoding B7-1 and B7-2, alone or in combination with cytokines, have been shown to enhance the development of immunity to experimental tumors in animal models (e.g. Leong et al. 1997 Int. J. Cancer 71: 476-482; Zitvogel et al. 1996 Eur. J. Immunol. 26:1335-1341; Cayeux et al. 1997 J. Immunol 158:2834-2841). However, in translating these results into a practical treatment for human cancer, there are a number of significant problems to be overcome. A major problem in such studies is the need to deliver B7 genes in vivo to a large number of cells of the tumor to achieve efficacy. A second problem is that it is important to target expression of B7 to the tumor cells to avoid inappropriate immune cell activation directed against other cell types.

This aspect of the present invention solves these specific problems by delivering a gene encoding a secreted co-stimulatory molecule ("SCM") with binding affinity for a tumor antigen. In this way, a relatively small number of transfected cells within the tumor act as a local factory to produce the co-stimulatory molecule which is shed from the producer cell and binds to other cells in the tumor. The aspect of the present invention has the additional advantage that tumor cells need not be the target for transfection.

The SCM of the invention is a novel engineered fusion protein comprising a signal peptide for secretion from mammalian cells, at least one antigen-binding domain from an immunoglobulin or an immunoglobulin-like molecule and at least one further domain which acts as a co-stimulatory signal to a cell of the immune system. The use of combinations of SCMs containing different co-stimulatory domains is also envisaged. The SCMs are produced by expression of SCM-encoding genes in the autologous cells of the individual to be treated and hence any post-translational modifications added to the protein by the host cell are authentic and provide fully functional protein and appropriate pharmacokinetics.

WO-A-92/00092 describes truncated forms of B7-1, derived by placing a translation stop codon before the transmembrane domain, secreted from mammalian cells. In that particular case, a heterologous signal peptide from the Oncostatin M gene was used. WO-A92/00092 also describes fusion proteins which contain the extracellular domain of B7-1 fused to the Fc region of an immunoglobulin. Such molecules can bind to CD28 on T-cells and serve to stimulate T-cell proliferation. However such stimulation occurs only to a moderate extent unless the B7 or B7-derivative is immobilized on a solid surface.

Gerstmayer et al. (1997 J. Immunol. 158: 4584-4590) describes a fusion of B7-2 to an scFv specific for ErbB2 followed by a myc epitope tag and polyhistidine tag which is secreted when expressed in the yeast *Pichia pastoris*. This molecule retained binding for antigen and co-stimulated proliferation of T-cells pre-stimulated with PMA and IL-2. However, glycosylation of such a molecule is of the yeast type, which is likely to lead to inappropriate pharmacokinetics in humans.

Thus in a preferred embodiment, the NOI encodes a co-stimulatory molecule or domain thereof. The co-stimulatory molecule or domain thereof may have binding affinity for a tumor antigen. The NS and the NOI may be linked and/or the antibody and POI (which, in this embodiment, comprises a co-stimulatory molecule or domain thereof) may be linked.

In accordance with the present invention, any suitable co-stimulatory domain(s) may be used. By way of example, co-stimulatory domains can be chosen from extracellular portions of the B7 family of cell-surface glycoproteins, including B7-1, B7-2 and B7-3 or other co-stimulatory cell surface glycoproteins such as but not limited to co-stimulatory receptor-ligand molecules including CD2/LFA-3, LFA-1/ICAM-1 and ICAM-3. Studies have demonstrated that T cell co-stimulation by monocytes is dependent on each of two receptor ligand pathways CD2/LFA-3 and LFA-1/ICAM-1 (Van Seventer et al 1991 Eur J Immunol 21: 1711-1718). In addition, it has been shown that ICAM-3, the third LFA-1 co-receptor, is a co-stimulatory molecule for resting and activated T lymphocytes (Hernandez-Caselles et al 1993 Eur J Immunol 23: 2799-2806).

Other possible co-stimulatory molecules may include a novel glycoprotein receptor designated SLAM, has been identified which, when engaged, potentiates T-cell expansion in a CD28-independent manner and induces a Th0/Th1 cytokine production profile (Cocks et al 1995 Nature 376: 260-263).

CD6, a cell surface glycoprotein, has also been shown to function as a co-stimulatory and adhesion receptor on T cells. Four CD6 isoforms (CD6a, b, c, d) have been described (Kobarg et al 1997 Eur J Immunol 27: 2971-2980). A role for the very late antigen (VLA-4) integrin in the activation of human memory B cells has also been suggested (Silvy et al 1997 Eur J Immunol 27: 2757-2764). Endothelial cells also provide unique co-stimulatory signals that affect the phenotype of activated CD4+ T cells (Karmann et al 1996 Eur J Immunol 26: 610-617). A B3 protein, present on the surface of lipopolysaccharide-activated B cells, which can provide co-stimulation to resting T cells leading to a predominant release of interleukin (IL)-4 and IL-5 and negligible amounts of IL-2 and interferon gamma has been described (Vinay et al 1995 J Biol Chem 270: 23429-23436). The co-expression of a novel co-stimulatory T cell antigen (A6H) on T cells and tumor cells has suggested a possible function related to common properties of these cells (Labuda et al 1995 Int Immunol 7: 1425-1432).

In one preferred embodiment of the invention, the co-stimulatory domain is a portion of B7-1 or B7-2, more preferably the complete extracellular portion of B7-1 or B7-2.

The SCM is formed by expression of a novel gene encoding a fusion protein containing the antigen-binding domain or domains and the co-stimulatory domain or domains. If the antigen-binding domain is comprised of a heavy and a light chain, the co-stimulatory domain is fused to one or other of the immunoglobulin chains, preferably to the heavy chain. If the antigen-binding domain is a scFv, the co-stimulatory domain is fused to the scFv. The domains can be placed in the order (N-terminus to C-terminus): antigen-binding domain followed by co-stimulatory domain; or co-stimulatory domain followed by antigen-binding domain. Preferably, the co-stimulatory domain is placed at the N-terminus followed by the antigen-binding domain. A signal peptide is included at the N-terminus, and may be for example the natural signal peptide of the co-stimulatory extracellular domain. The different domains may be separated by additional sequences, which may result from the inclusion of convenient restriction-enzyme cleavage sites in the novel gene to facilitate its construction, or serve as a peptide spacer between the domains, or serve as a flexible peptide linker or provide another function. Preferably the domains are separated by a flexible linker.

Two or more different genes encoding different SCMs may be used to achieve improved co-stimulation, or both co-stimulation of naïve T-cells and induction of memory responses. For example a gene encoding an SCM containing the B7-1 extracellular domain may be administered with a gene encoding an SCM containing the B7-2 extracellular domain.

Thus in one aspect of the invention, there is provided one or more genetic vectors capable of expressing in mammalian cells one or more secreted co-stimulatory molecules, each secreted co-stimulatory molecule comprising at least one antigen-binding domain and at least one domain from the extracellular portion of a cell-surface co-stimulatory molecule. The co-stimulatory domain may be obtained from a molecule expressed on the surface of an antigen-presenting cell such as a B7 family member. Preferably the co-stimulatory domain is from B7-1, B7-2 or B7-3. Most preferably it is comprised of B7-1 amino acid residues 1 to approximately 215 of the mature B7-1 molecule (described in WO-A-96/00092) or amino acids 1 to approximately 225 of the mature cell-surface form of B7-2 (described in Gerstmeyer et al. 1997 J. Immunol. 158:4584-4590).

The genetic vector according to this aspect of the invention comprises at least a promoter and enhancer for expression in mammalian cells and a polyadenylation site. Suitable promoters and enhancers include the MIE promoter-enhancer from human cytomegalovirus or promoters which are expressed preferentially in cells present within the tumor. Such promoter-enhancers include those from the MUC1 gene, the CEA gene or the 5T4 antigen gene. If two or more SCMs are expressed, the coding regions for these may be inserted into two separate vectors or a single vector may be used to express the two or more genes. In the latter case each gene is provided with a separate copy of the promoter, or an internal ribosome entry site (IRES) is used to separate the two coding sequences.

Effector Domains

The antibody and/or the POI of the present invention may also contain one or more effector domains. The effector domain or domains may be activated on binding of the antibody to a cell surface molecule ("CSM") leading to inhibition of cell proliferation, survival or dissemination. The CSM in this aspect of the invention is a cell surface molecule for which a specific TBP is available such as a tumor specific carbohydrate moiety, an oncofoetal antigen, a mucin, a growth-factor receptor or another glycoprotein. The CSM is preferably an antigen restricted in its tissue distribution (for example, it may be restricted to tumor cells). In some instances, the CSM is not shed from the cell surface into the circulation to an appreciable extent. However, shedding may occur. By way of example, shedding of the 5T4 antigen into the stroma can serve to further localize the NOI and/or the POI to the tumor environment.

The effector domain of the present invention may possess enzymatic activity and may be for example a pro-drug activating enzyme, or it may be a non-enzyme domain. Examples of antibodies containing effector domains with enzyme activity include antibody-enzyme conjugates or fusions. Antibody-enzyme conjugates have been described including conjugates with alkaline phosphatase (Senter et al., 1988 Proc. Natl. Acad. Sci. 85: 48424846); carboxypeptidase G2 (Bagshawe et al. 1988 Br. J. Cancer 58: 700703); P-lactamase (Shepherd et al 1991 Bioorg. Med. Chem. Left. 1:21-26); and Penicillin-V-amidase (Kerr et al. 1990 Cancer Immunol. Immunother. 31: 202-206. Antibody-enzyme fusions have also been described (Goshorn et al 1993 Cancer Res 53: 2123-2127; Wels et al 1992 Bio/Technology 10: 1 1 28-1132). Each of these examples can be used in this aspect of the invention. Additional or alternative enzymes which may be included in antibody-enzyme fusions include human Carboxypeptidase A1 or a mutant thereof (Smith et al 1997 J. Biol. Chem. 272: 15804-15816); cytosine deaminase (Mullen et al. 1994 Cancer Res. 54: 1503-1506); HSV thymidine kinase (Borrelli et al. 1988 Proc. Natl. Acad. Sci. 85: 7572-7576.); nitroreductase; P450-Reductase and a P450.

Preferably the pro-drug activating enzyme domain or domains are genetically fused to the C-terminus of an immunoglobulin or immunoglobulin domain such as a scFv or a single-chain antibody or Fab-fragment. In a particularly preferred embodiment of this aspect of the invention, the immunoglobulin domain or domains are human or humanized and the enzyme is a human enzyme—such as a Carboxypeptidase a P450 or P450-Reductase. The enzyme may be a mutant enzyme which converts a pro-drug more efficiently than does the native human enzyme. In accordance with the present invention, any enzyme that has utility in an ADEPT strategy can be used.

In each case, a suitable pro-drug is used in the treatment of the patient in combination with the appropriate pro-drug activating enzyme. Examples of pro-drugs include etoposide phosphate (used with alkaline phosphatase Senter et al, 1988 Proc. Nat. Acad. Sci. 85: 4842-4846); 5-fluorocytosine (with Cytosine deaminase Mullen et al. 1994 Cancer Res. 54: 1503-1506); Doxorubicin-N-p-hydroxyphenoxyacetamide (with Penicillin-V-Amidase (Kerr et al. 1990 Cancer Immunol. Immunother. 31: 202-206); Para-N-bis(2chloroethyl) aminobenzoyl glutamate (with Carboxypeptidase G2); Cephalosporin nitrogen mustard carbamates (with P-lactamase); SR4233 (with P450 Reducase); Ganciclovir (with HSV thymidine kinase, Borrelli et al. 1988 Proc. Natl. Acad. Sci. 85: 7572-7576) mustard pro-drugs with nitroreductase (Friedlos et al. 1997 J Med Chem 40: 1270-1275) and Cyclophosphamide (with P450 Chen et al. 1996CancerRes56: 1331-1340).

Alternatively the effector domain may be a non-enzyme domain. Examples of non-enzyme effector domains include toxins such as an exotoxin from a pseudomonad bacterium, all or part of a cytokine such as IL-2 or IFN$_\gamma$, or effector domains from immunoglobulin heavy chains.

In a preferred embodiment of this aspect of the invention, the antibody or POI contains an effector domain capable of activating macrophage FcgR I, II or III receptors. On binding of the TBP to antigen on the tumor cells, macrophages present within the hypoxic regions of the tumor are activated to destroy the tumor cells directly by phagocytosis or ADCC or are activated to secrete pro-inflammatory cytokines which serve to enhance the natural immunological response to the tumor. The antibody or POI may contain an Fc region from an immunoglobulin, a mutant Fc region, a receptor-binding fragment of the Fc region or may contain another FcR—binding domain.

Preferably the antibody or POI contains an entity, preferably an effector domain entity, that confers protein stability ex vivo and/or in vivo.

In accordance with the present invention, the antibody or POI may be or include an intact Fc region from an IgG, (such as human IgG1 or IgG3, or a part thereof. In one preferred embodiment of this aspect of the invention, the antibody or POI is a Sab (single chain antibody) containing a human IgG1 constant region and a binding domain which recognizes the 5T4 antigen. In a particularly preferred embodiment of this aspect of the invention, the antibody or POI is a Sab (single chain antibody) containing a human IgG constant region and a binding domain which recognizes the 5T4 antigen.

The effector domain may be encoded by a portion of a cDNA fused in-frame to the DNA encoding the antibody or POI. Alternatively a genomic fragment containing introns may be used such as a human IgG1 heavy chain constant region genomic fragment. Here the term "intron" is used in its normal sense—e.g. an intervening sequence of DNA within a gene which is removed by RNA splicing and so is not present in the mature messenger RNA and does not code for protein. Introns can be conditional or alternatively spliced in different cell types.

Introduction of antibody and/or NOI genes into monocytes or macrophages may be combined with further treatments to elicit macrophage differentiation and activation. For example, cells maintained ex vivo may be treated with cytokines such as IFN$\gamma$, CSF-1 or GM-CSF prior to re-introduction into the patient. Alternatively, genes encoding these cytokines may be introduced into the monocytes/macrophages in the same or a different vector system in vivo or ex vivo. Consequently in a still further aspect of the invention there is provided a method of treating a disease in a mammal which comprises administering to an individual a combination of a cytokine or a cytokine—encoding gene and one or more antibody genes.

Additional Functional Component

The antibody and/or the NOI may further comprise at least one additional functional component. Preferably the additional functional component is selected from any one or more of a signaling entity (such as a signal peptide), an immune enhancer, a toxin, or a biologically active enzyme. In a preferred aspect the POI is a secretable POI. Thus, in this aspect of the present invention, preferably, the additional functional component is at least an entity capable of causing the POI to be secreted—such as a signaling entity.

The NS and/or NOI may also comprise an additional functional component, such as a promoter. The term "promoter" is used in the normal sense of the art, e.g an RNA polymerase binding site in the Jacob-Monod theory of gene expression. Preferably the vector system comprises a tumor specific promoter enhancer.

Other preferred additional components include entities enabling efficient expression of the antibody and/or POI. For example, the additional component may be an enhancer. Here, the term enhancer includes a DNA sequence which binds to other protein components of the transcription initiation complex and thus facilitates the initiation of transcription directed by its associated promoter.

As well as pomoter(s) and/or enhancer(s) the NS or NOI may comprise translation initiation signals, internal ribosome entry sites (IRES), splicing and polyadenylation signals.

The promoter and/or enhancer may be tissue-restricted in its activity. For example a tumor-specific promoter-enhancer, such as a 5T4 antigen gene promoter-enhancer or the CEA-gene promoter-enhancer may be used. Alternatively, or additionally, an element or elements for regulated expression may be present, such as a hypoxia regulated enhancer. An example of a hypoxia regulated expression element (HRE) is a binding element for the transcription factor HIF1. The enhancer elements or elements conferring regulated expression may be present in multiple copies. Preferably, expression of the gene (such as a therapeutic gene) is inducible by hypoxia (or low oxygen supply) such as may be found in a tumor mass. Most preferably, the promoter and/or enhancer directing expression of the gene (such as a therapeutic gene) contains both hypoxia-responsive elements and elements which give higher expression in tumor cells than in neighboring non-tumor cells.

Pharmaceutical Compositions

The present invention also encompasses a pharmaceutical composition for treating one or more individuals by gene therapy, wherein the composition comprises a therapeutically effective amount of the vector system according to the present invention. The pharmaceutical composition may be for human or animal usage. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilizing agent(s), and other carrier agents that may aid or increase the viral entry into the target site (such as for example a lipid delivery system).

Where appropriate, the pharmaceutical compositions can be administered by any one or more of: inhalation, in the form of a suppository or peccary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The invention will now be further described by way of examples, which are meant to serve to assist one of ordinary skill in the art in carrying out the invention and are not intended in any way to limit the scope of the invention.

EXAMPLES

The following examples are intended to illustrate but not limit the invention.

Example 1

Construction of 5T4 Sab and Retroviral—Vector Delivery to Tumor

The cDNA encoding the murine 5T4 monoclonal antibody is cloned and sequenced by standard techniques (Antibody engineering: a practical approach Ed McCafferty et al. 1996 OUP). The sequence of the variable region of the antibody can be used to construct a variety of immunoglobulin-like molecules including scFvs. The coding sequence of a 5T4 scFv, 5T4scFv.1, is shown in FIG. 1a. In this molecule, the DNA sequence encodes the Vh from the mouse 5T4 monoclonal antibody followed by a 15 amino acid flexible linker and the Vl region of the mouse 5T4 antibody. The flexible linker encodes 3 copies of the amino-acid sequence gly-gly-gly-gly-ser (Portion of SEQ ID NO:1) and the DNA sequence similarity between the repeats has been minimized to avoid the risk of recombination between the repeats when plasmids containing them are grown in *E. coli*.

The DNA sequence shown in FIG. 1a can also be used to construct a variety of single-chain antibodies (Sabs) by coupling scFv—encoding sequences to a sequence encoding a Fc region to form an in-frame fusion. A Sab is constructed using a series of DNA cassettes which can be independently varied to suit particular purposes.

Cassette 1—Translation initiation signal and signal peptide

In order to achieve correct translation initiation and secretion from mammalian cells, the following sequence is used:

aagcttCCACCATGGgatggagctgtat-catcctcttcttggtagcaacagctacaggtgtccactCc (SEQ ID NO:18)

This contains a convenient HindIII restriction site for cloning into expression vectors (lower case), the consensus translation initiation signal for mammalian cells (ANNATGPu) (SEQ ID NO: 19) and the coding sequence for a signal peptide sequence from an immunoglobulin gene.

The sequence of the secreted portion of the 5T4scFv.1 is shown in FIG. 1a. This molecule can be represented as Vh—(gly$_4$-ser)$_3$ linker—VI(Portion of SEQ ID NO:1).

5T4 scFv2 consists of the 5T4 variable region sequences connected in the order VI—flexible linker Vh. In this case the linker encodes the 20 amino-acid peptide (gly4-ser)4(SEQ ID NO:20). A longer linker improves assembly of the scFv when the V-region segments are in this order. (Pluckthun et al in Antibody Engineering: a practical approach, Ed McCafferty et. al. 1996 OUP).

Cassette 3—Heavy chain Constant region

The sequence of a human g1 constant region genomic clone is given in Ellison et al. 1982 Nucl. Acids res. 10: 4071-4079. This sequence contains constant—region introns in addition to the coding sequence. This is fused in-frame to the 3'-end of one of the scFv sequences from Cassette 2. Vectors for convenient assembly of such constructs are described (Walls et al. 1993 Nucl. Acids Res. 21:2921-2929.

A cDNA of a 5T4 Sab, designated 5T4Sab1 is shown in FIG. 1b, containing cassettes 1, 2 and 3.

For expression of a 5T4-specific scFv or Sab in human cells, the coding sequence is inserted into the vector pCIneo (Promega) under the control of a strong promoter and poly-adenylation signal. The translation initiation signal and immunoglobulin leader (signal peptide) sequence from Cassette 1 at the 5' end of the coding region ensure efficient secretion of the scFv or Sab from mammalian cells.

For expression of an intact Ig, two separate translation cassettes are constructed, one for the heavy chain and one for the light chain. These are separated by an internal ribosome-entry site (IRES) from the picornavirus FMDV (Ramesh et al. 1996 Nucl. Acids Res. 24: 2697-2700. Alternatively, each cDNA is expressed from a separate copy of the hCMV promoter (Ward and Bebbington 1995 In Monoclonal Antibodies ed Birch and Lennox.Wiley-Liss).

For production of retrovirus capable of expressing 5T4 antibody or immunoglobulin-like molecules with 5T4 specificity, the gene encoding a 5T4-based Sab, or a dicistronic message encoding heavy and light chains, is inserted into a retroviral vector in which retroviral genomic transcripts are produced from a strong promoter such as the hCMV-MIE promoter. A suitable plasmid is pHIT111 (Soneoka et al. 1995 Nucl. Acids Res.23; 628-633) and the required gene is inserted in place of the LacZ gene using standard techniques. The resulting plasmid, pHIT-5T4.1 is then transfected into the FLYRD18 or FLYA13 packaging cell lines (Cosset et al. 1995 J. Virol. 69; 7430-7436) and transfectants selected for resistance to G418 at 1 mg/ml. G418-resistant packaging cells produce high titres of recombinant retrovirus capable of infecting human cells. The virus preparation is then used to infect human cancer cells and can be injected into tumors in vivo. The 5T4 Sab is then expressed and secreted from the tumor cells.

In pHIT111, the MoMLV LTR promoter-enhancer is used for expression of the therapeutic gene in the target cell. The vector can also be modified so that the therapeutic gene is transcribed from an internal promoter-enhancer such as one which is active predominantly in the tumor cells or one which contains a hypoxia regulated element. A suitable promoter is a truncated HSV TK promoter with 3 copies of the mouse PGK HRE (Firth et al. 1994 Proc. Natl. Acad. Sci. 91: 6496-6500).

Example 2

Transfection of Macrophages/Monocytes with an Expression Vector Encoding TBP

Peripheral blood mononuclear cells are isolated from human peripheral blood at laboratory scale by standard technique procedures (Sandlie and Michaelsen 1996 In Antibody engineering: a practical approach. Ed McCafferty et al. Chapter 9) and at large scale by elutriation (e.g. Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing TBP in human cells. For constitutive high level expression, the TBP is expressed in a vector which utilizes the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (e.g. using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 3

Assay for ADCC Mediated by Macrophages

Cells from primary human tumors or tumor cell lines which have been transduced with retrovirus expressing TBP are mixed with autologous or heterologous human macrophages, prepared as described in Example 2, for analysis of ADCC activity mediated by the TBP. Alternatively, macrophages engineered to produce TBP as described in Example 2 can be used to direct ADCC on non-transduced tumor cells.

The assay is carried out according to standard procedures (Sandlie and Michaelsen 1996 In Antibody engineering: a practical approach. Ed McCafferty et al. Chapter 9) with appropriate modifications. Briefly, the effector cells (macrophages or freshly isolated monocytes) are suspended at $3 \times 10^6$ cells/ml in the appropriate tissue culture medium (DMEM/Hepes, obtained from Life Technologies, containing 1% Foetal Calf Serum). $3 \times 10^5$ tumor target cells, labeled with 51Cr are placed in each well of a round-bottomed microtitre plate in 0.1 ml culture medium. (Note the culture medium can include spent medium from the cells producing the TBP). 50 ml effector cells are added to the wells, the plate is centrifuged at 300 g for 2 min and incubated at 37° C. for varying periods (e.g. 4 h) in a tissue culture incubator. The supernatant is then harvested by centrifugation and counted in a gamma counter. Results are expressed as percent lysis relative to total chromium release from an equivalent sample of target cells lysed with 0.1% Tween-20. The effector: target cell ratio can be varied in the assay to produce a titration curve.

For the prior stimulation of macrophage differentiation or priming, cytokines are added to the cultures. IFNg (Sigma) is added at between 100 and 5000 U/ml. CSF-1 or GM-CSF (Santa Cruz Biotechnology) can also be added at appropriate concentrations.

Example 4

Analysis of Efficacy in Animal Models

Human tumor-derived cell lines and tissues are cultured in vivo in genetically immunodeficient, "nude" mice according to well established techniques (see for example Strobel et al. 1997 Cancer Res. 57: 1228-1232; McLeod et al. 1997 Pancreas 14: 237-248). Syngeneic mouse models, in which a syngeneic tumor line is introduced into an immunocompetent mouse strain may also be used. These serve as suitable animal models for evaluating gene delivery systems of the invention. Vectors or engineered cells are administered systemically or directly into the tumor and tumor growth is monitored in treated and untreated animals. This system is used to define the effective dose range of the treatments of the invention and the most appropriate route of administration.

Example 5

Construction of B7-scFv Fusion Proteins

The extracellular domain of B7-1 is defined by amino-acid residues 1-215 of the native human B7- 1 protein. This sequence, together with its signal peptide-encoding sequence, is used to construct secreted fusion proteins which also contain the scFv derived from the 5T4 monoclonal antibody. The sequence of the 5T4 scFv is given in FIG. 1a.

Figure 3B:
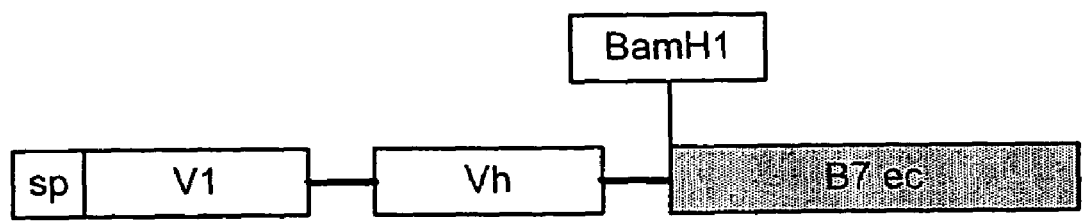

A DNA coding sequence is constructed using standard molecular biology techniques which encodes a fusion protein in which the N-terminus of the 5T4 scFv is fused after amino acid 215 of human B7-1. The sequence of this coding sequence, B7-1.5T4.1, is shown in FIG. 2. The fusion protein contains a flexible (gly-gly-gly-gly-ser)(Portion of SEQ ID NO:39) spacer between the B7-1 and 5T4 scFv sequences. The introduction of a convenient BamH1 restriction site at the end of the linker insertion (beginning at nucleotide 733) also allows for further linkers to be screened for optimal expression of bi-functional fusion protein. FIG. 3 indicates the fusion protein in diagrammatic form. It is similarly possible to construct B7-1.5T4.2 (FIG. 3b) in which the scFv is N-terminal and the B7 extracellular domain is C-terminal. In this case only the coding sequence of the mature B7-1 (without signal peptide) is required. A signal peptide such as an immunoglobulin leader sequence is added to the N-terminus of the scFv in this instance.

For fusion proteins which use the co-stimulatory extracellular domain of B7-2, the signal peptide and extracellular domain of B7-2 is used in place of B7-1 sequences. FIG. 4 shows the coding sequence of the SCM B7-2.5T4.1 co-stimulatory domain. It encodes the first 225 amino acids of human B7-2, preceded by its signal peptide, and a flexible linker (gly4-ser) (Portion of SEQ ID NO:40).The BamHI site at the end of this sequence can be used to insert the domain upstream of the 5T4scFv.1 (see FIG. 3). The sequence includes the B7-2 signal peptide which can serve to allow secretion of this fusion protein in which the B7-2 domain is at the N-terminus of the fusion protein.

Each engineered cDNA is inserted into the mammalian expression vector pCI to allow expression in mammalian tissue culture cells. For this purpose, a linker sequence is added to the 5'-end of the coding sequence which introduces a convenient restriction site for insertion into the polylinker of pCI and adds the translation initiation signal CCACC immediately adjacent to the first ATG codon. Constructs in pCI are transfected into a suitable mammalian host cell line such as COS-1 to confirm secretion of the SCM. The transcription cassette from pCI or an appropriate segment of the transcription cassette is subsequently sub-cloned into the expression vector to be used as the gene delivery system for therapeutic use.

Example 6

Transfection of Macrophages/Monocytes with an Expression Vector encoding an SCM

Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (e.g. Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing SCM in human cells. For constitutive high level expression, the SCM is expressed in a vector which utilizes the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (e.g. using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc or Quantum Biotechnologies Inc).

Example 7

Analysis of SCM Binding to CTLA-4 and 5T4-Antigen Expressing Cells

The B7-1 or B7-2 domains are expected to bind specifically to CD28 and CTLA-4 present on human T-cells. Binding to T-cells or Chinese hamster ovary cells transfected with human CTLA-4 or CD28 is determined using FACS analysis as follows. $5 \times 10^5$ CTLA-4 expressing target cells or equivalent cells lacking CTLA-4 (untransfected CHO cells) are incubated with 0.1 ml culture supernatant from COS-1 cells transiently transfected with SCM genes for 1 h at 4° C. The cells are washed and incubated with 1 µg monoclonal antibody specific for the B7 domain (e.g. Mab 9E10) followed by FITC-labeled goat anti-mouse IgG (Pharmingen) and analysis by FACS.

Binding of scFv to 5T4-antigen is similarly assessed using target cells expressing 5T4-antigen (5T4-transfected A9 cells) or control cells (A9).

Example 8

Analysis of Co-Stimulatory Activity

An established mouse cell line of Balb/c origin such as HC11 cells is transfected with the cDNA encoding human 5T4-antigen (Myers et al. 1994 J. Biol. Chem. 269; 9319-9324) inserted in the expression vector pCIneo.

Splenic T-cells from Balb/c mice are isolated by standard procedures (Johnstone and Thorpe 1996 In Immunochemistry in Practice. Blackwell. Chapter 4). T-cells are pre-stimulated by incubation for 1-2 days in medium containing 10ng/ml PMA (Sigma) and 100 U/ml human IL-2 (Boehringer Mannheim). HC11-5T4 cells are incubated at 104 cells /well of a 96-well tissue culture tray for 2 h with up to 0.1 ml supernatant from COS cells transfected with SCM gene. Up to $10^5$ pre-stimulated T-cells are added to each well, the cells are pulsed with 0.25 mCi/well $^3$H-thymidine and incorporation of $^3$H-thymidine is measured using a liquid scintillation counter after 24 h.

Incorporation of $^3$H-thymidine is anticipated to be enhanced by the presence of SCM.

Example 9

Analysis of Co-Stimulation in Animal-Models.

HC11 cells transfected with the human 5T4-antigen gene (Example 4) are grown as tumors in Balb/c mice. SCM genes B7-1.5T4.1 or B7-2.5T4.1 or a combination of both genes ced into the tumor cells prior to implantation and the growth of the tumors and the control tumors which do not express SCM genes in vivo are monitored.

It is believed that the expression of SCM genes lead to significant reduction in tumor growth.

Example 10

Construction of a B7-1/ScFv, Specific for Human 5T4, Fusion Protein

Standard molecular biology techniques are used to construct a fusion protein consisting of the leader sequence and extracellular domain of B7-1, fused via a flexible linker to the $V_H$ and $V_L$ of the murine Mab 5T4 specific to human 5T4.

The flexible linker, used to join the extracellular domain of B7.1 and the ScFv, was constructed by annealing two homologous oligonucleotides with engineered 5' Sma I and 3' Spe I sites—using oligonucleotides upper (SEQ ID NO:21)
5' GGG ggt ggt ggg agc ggt ggt ggc ggc agt ggc ggc ggc gga A 3' and lower (SEQ ID NO:22)
5' CTA GTT CCG CCG CCG CCA CTG CCG CCA CCA CCG CTC CCA CCA CCC CC 3'

The linker is cloned into pBluescript (Stratagene) via Sma I and Spe I to produce pLINK. The signal peptide (sp) and extracellular domain of murine B7.1 were amplified by PCR from pLK444-mB7.1 (supplied by R. Germain NIH, USA) via primers that introduce 5' EcoRI and 3' Sma I sites—primers forward (SEQ ID NO:23)
5' c tcg aat tcc acc ATG gct tgc aat tgt cag ttg atg c 3' reverse (SEQ ID NO:24)
5' CTC CCC GGG CTT GCT ATC AGG AGG GTC TTC 3'

The B7.1 PCR product was cloned into pLINK via Eco RI and Sma I to form pBS/B7Link.

The VH and VL of the 5T4 specific ScFv was amplified via primers— forward primer (SEQ ID NO:25)
5' ctc act agt gag gtc cag ctt cag cag tc 3' reverse primer (SEQ ID NO:26)
5' Ctc gcg gcc gct tac cgt tgg att tcc agc ttg gtg cct cca cc 3' that introduce 5' Spe I and 3' Not I sites from pHEN1-5T4 ScFv. PBS/B7Link was digested with Spe I and Not I and ligated with the ScFv to form OBM 233 consisting of the sequence shown as SEQ ID No. 5: B7 Link scFv sequence This fusion can be used to construct a recombinant vector e.g. retrovirus, Lentivirus, adenovirus, poxvirus, vaccinia virus, baculovirus. Such vectors can be used to inject patient tumors directly. To deliver the fusion protein to tumor cells the recombinant vector is used to transduce macrophages/monocytes/CD34+ cells ex vivo before injection back into patients. These cells will traffic to tumors. The ScFv will bind to a specific tumor antigen expressed on the surface of tumor cells e.g. 5T4 (Myers et al 1994 JBC). B7 is found on the surface of professional antigen presenting cells e.g. macrophages, dendritic cells and B cells. It interacts with its ligands CD28 and CTL-A4 located on CD4 and CD8 cells. The simultaneous interaction of B7-CD28/CTL-A4 and MHC-peptide/T cell receptor leads to a pronounced increase in IL-2 which promotes CD8 (cytotoxic T cell) expansion (Linsley P S, Brady W, Grosmaire L, Aruffo A, Damle N K, Ledbetter J A J Exp Med 1991 March 1;173(3):721-730 Binding of the B cell activation antigen B7 to CD28 co-stimulates T cell proliferation and Il-2 mRNA accumulation.) Tumor cells that have been transfected with B7 have shown retardation in animal models (Townsend S E, Allison J P Science 1993 15;259(5093):368-370).

Example 11

Transient Expression and Purification of B7-1/ScFv and LScFv

For transient expression of B7-1/ScFv the human CMV expression plasmid pCIneo (Promega) was used. B7/ScFv was excised from OBM 233 by digestion with EcoR I/Not I and cloned into pCIneo that was previously digested with EcoRI/Not I. Transient expression of recombinant protein is made by transfection of 293T cells with the relevant plasmid using calcium phosphate (Profectin, Promega). Conditions used were similar to those recommended by the manufacturer. To reduce bovine serum contamination serum-free Optimem Media (Gibco BRL) was used. After 36-48 hours transfection supernatants were harvested and spun through a Centriprep (Amicon, Glos. UK) 10 filter (all proteins larger than 10 kDa are purified/concentrated) and a Centricon (Amicon) 10 filter. Supernatants are concentrated approximately 30 fold.

For B7-1 to be biologically functional it must be able to display binding with one of it's natural ligands either CTLA-4 or CD28 found on the surface of specific populations of T cells (e.g. CD4+). The biological activity B7-1/ScFv fusion protein was analysed for simultaneous interaction with its natural ligand CTLA-4 (in the form of CTLA-Ig supplied by Ancell, M N, USA) and A9 cells expressing human 5T4. Briefly: approximately 5×105 A9-h5T4 cells were incubated with 100 µl of either B7.1/ScFv or LScFv supernatant in a U bottom 96 well plate at 4° C. for 1 hour. After washing cells were incubated with CTLA4-Ig (Ancell) for 1 hour. After washing, bound CTLA4-Ig was detected using an FITC conjugated anti-mouse Ig (Dako).

Results show obvious binding of CTLA4-Ig with the B7-1 extracellular domain, bound via the ScFv, to the surface of human 5T4 positive A9 cells. The lack of binding activity with 5T4 negative A9 cells further illustrates that the interaction of B7 with CTLA4-Ig and ScFv with 5T4 are specific.

Example 12

ScFv-IgG Fusion Example

Construction of ScFv-IgG

The sequence encoding a translation initiation sequence and the human immunoglobulin kappa light chain signal peptide is synthesized as two complementary single stranded oligonucleotides which when annealed also contain an internal Xho I site at the 5' end and in addition leave a Xba I compatible 5' overhang and a Pst I compatible 3' overhang

```
ctagactcgagCCACC ATG GGA TGG AGC TGT ATC ATC CTC
TTC TTG GTA GCA ACA GCT ACA GGT GTC CAC TCC GAG
GTC CAG ctgca
``` and

```
g CTG GAC CTC GGA GTG GAC ACC TGT AGC TGT TGC
TAC CAA GAA GAG GAT GAT AGA GCT CCA TCC CAT
GGTGGctcgagt
```

This is then cloned into pBluescript II (Stratagene) restricted with Xba I and Pst I to create pBSII/Leader.

The 5T4 scFv is amplified by PCR from pHEN1 using oligonucleotides which incorporate a Pst I site at the 5' end of the product and a Hind III at the 3' end (SEQ ID NO:29)
```
        GTC CAG CTG CAG CAG TCT GG
``` and (SEQ ID NO:30)
```
        CG TTT GAT TTC AAG CTT GGT GC
```

This is then restricted with those enzymes and inserted into pBSII/Leader restricted with the same enzymes, creating pBSII/Leader/scFv.

The HIgG 1 constant region is amplified by PCR from the cloned gene using oligonucleotides which incorporate a Hind III site at the 5' end and a Xho I site at the 3' end (SEQ ID NO:31)
```
gcgc AAG CTT gaa atc aaa cgg GCC TCC ACC AAG GGC
CCA
``` and (SEQ ID NO:32)
```
    gcgc ctcgag TCA TTT ACC CGG AGA CAG GG
```

This is then restricted with those enzymes and inserted into pBSII/Leader/scFv restricted with the same enzymes, creating pBSII/Leader/scFv/HG1. The sequence for this construct is shown in the Figures.

This fusion can be used to construct a recombinant vector e.g. retrovirus, Lentivirus, adenovirus, poxvirus, vaccinia virus, baculovirus. Such vectors can be used to inject patient tumors directly. To deliver the fusion protein to tumor cells the recombinant vector is used to transduce macrophages/monocytes/CD34+ cells ex vivo before injection back into patients. These cells will traffic to tumors. The ScFv will bind to a specific tumor antigen expressed on the surface of tumor cells e.g. 5T4 (Myers et al 1994 JBC). Bound IgG will promote specific tumor destruction via a collection of mechanisms collectively known as antibody dependent cellular cytotoxicity (Munn et al Can Res 1991 ibid, Primus et al 1993 Cancer Res ibid).

Example 13

Construction of ScFv-IgE1 (Human IgE1 Heavy Constant Region)

A similar fusion construct of 5T4 scFv-human IgE constant heavy chain is made consisting of the sequence shown as SEQ ID No. 6.

This fusion construct is made by amplifying the human IgE1 constant heavy region by PCR cDNA derived from human B-cells RNA by RT and subsequently using oligonucleotides which incorporate a Hind III site at the 5' end and a Xho I site at the 3' end (SEQ ID NO:33)
```
gcgc AAG CTT gaa atc aaa cgg GCC TCC ACA CAG AGC
CCA
``` and (SEQ ID NO:34)
```
    gcgc ctcgag TCA TTT ACC GGG ATT TAC AGA
```

This is then restricted with those enzymes and inserted into pBSII/Leader/scFv restricted with the same enzymes, creating pBSII/Leader/scFv/HE1.

As described above the ScFv-IgE construct can be incorporated into a recombinant viral vector for use in gene therapy of cancer e.g. inject patient tissue directly or to transduce patient derived macrophages/moncytes/CD34+ cells ex vivo. The fusion protein will be secreted and will bind to tumor cells bearing the antigen that the ScFv is specific for. Binding of IgE to tumor cells should promote a strong histamine response via activation of mast cells. This will lead to a strong inflammatory response and destruction tumor cells as is reported for IgE cytotoxic destruction of parasites e.g. helminth larvae (Capron M 1988 Eosinophils in diseases: receptors and mediators. In progress in allergy and clinical imrnunology (Proc. 13$^{th}$ Int. Congress of Allergy and Clinical Immunology) Hogrefe & Huber Toronto p6). Such inflammation and tumor destruction should initiate the recruitment of other immune effector cells. Past reports indicate that treatment with an MMTV antigen specific IgE Mab leads to protection from a tumor expressing MMTV antigen (Nagy E Istanvan B, Sehon A H 1991 Cancer Immunol. Immunotherapy Vol. 34:63-69).

Example 14

Construction of B7/EGF

B7-EGF Synthetic Gene.

A fusion construct of B7- EGF is made by inserting a PCR product amplified from the region of the gene encoding the mature EGF peptide (see accession number X04571) into pBS/B7 Link. This construct has the sequence shown as SEQ ID No. 7.

Using cDNA derived by RT of RNA isolated from a cell line such as the 293 human kidney line (ATCC: CRL1573), the DNA is amplified by PCR using oligonucleotides containing a Spe I restriction enzyme site at the N-terminus and a stop codon and a Not I site at the C-terminus: GG ACT AGT AAT AGT GAC TCT GAA TGT CCC (SEQ ID NO:35) and ATT AGC GGC CGC TTA GCG CAG TTC CCA CCA CTT C (SEQ ID NO:36).

The resulting product is digested with those enzymes and ligated to pBS/B7 Link which has been restricted with the same enzymes creating pBS/B7 Link EGF. The B7 Link EGF cassette is then excised with Eco RI and Not I and inserted into a derivative of pHIT111 (Soneoka et al.,1995, Nucl Acid Res 23; 628) which no longer carries the LacZ gene An alternative to using ScfV is to use growth factors that have a high affinity to their corresponding receptor e.g. epidermal growth factor which binds to several receptors including erb-B2 which is highly associated with tumourgenesis.

As described above the fusion construct can be incorporated into a recombinant viral vector for use in gene therapy e.g. inject patient tissue directly or to transduce patient derived macrophages/monocytes/CD34+ cells ex vivo. The fusion protein will be secreted and will bind to tumor cells bearing the erb-2 antigen.

Epidermal growth factor (EGF) will bind to Erb-B2, which is an EGF receptor thus obviating the requirement of a ScFv. Erb-B2 is highly associated with tumor cells (Hynes N E Semin Cancer Biol 1993 February;4(1):19-26, Amplification and over expression of the erb-B2 gene in human tumors: its involvement in tumor development, significance as a prognostic factor, and potential as a target for cancer therapy). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to massive increase in IL-2 which promotes CD8 (cytotoxic T cell) expansion (Linsley P S, Brady W, Grosmaire L, Aruffo A, Damle N K, Ledbetter J A J Exp Med 1991 March 1;173(3):721-730 Binding of the B cell activation antigen B7 to CD28 costimulates T cell proliferation and interleukin-2 mRNA accumulation.) Tumor cells that have been B7 transfected with B7 have shown retardation in animal models (Townsend S E, Allison J P Science 1993 15;259(5093):368-370 Tumor rejection after direct costimulation of CD8+ T cells by B7-transfected melanoma cells). It is has been reported that B7 will enhance the CTL response to tumor antigens specific to tumor cells thus leading to the destruction of all such cells.

Example 15

Production of Cell Lines Expressing Fusion Constructs

The ScFv-IgG gene was excised from pBSII/L/ScFv/hIgG1 by Xho I digestion, and cloned into pLXSN via the Xho I site, to make pLXSN/ScFv-IgG, such that after chromosomal integration it is under transcriptional control of the LTR. Virus was made in the human kidney cell line 293T by co-transfecting plasmids containing the MLV gap-pol genes (pCIEGPPD) and and the VSV G envelope (pRV67) using the triple plasmid HIT system (Landau & Littman 1992 J Virol 66 5110, Soneoka Y et al 1995 NAR 23:628-633). Virus is harvested after 48 hours and used to transduce BHK-21 cells (ATCC# CCL- 10). Approximately 24 hours post-transduction, transduced cells are selected by the addition of 1 mg/ml G418 (Gibco BRL) to culture medium. The supernatant from positive colonies was harvested and concentrated by centrifugation through a Centriprep (Amicon, Glos. UK) 10 filter (all proteins larger than 10 kDa are purified/concentrated) and a Centricon (Amicon) 10 filter. Supernatants were concentrated approximately 30 fold. Other fusion proteins are cloned into pLXSN via the Xho I site and expressed and concentrated using a similar protocol.

FACS analysis of fusion protein binding with cells expressing specific ligand

To determine if the ScFv-IgG fusion protein is specific for its antigen, human 5T4, FACS analysis of a human bladder carcinoma tumor line (EJ) or a stable murine cell line expressing h5T4, A9-h5T4 (Myers et al 1994 JBC) and a 5T4 negative line A9-neo was carried out. Approximately $5 \times 10^5$ A9 or EJ cells, in a round bottom 96 well plate (Falcon) were incubated with 100 µl of a 1:5 dilution of concentrated supernatant (as described above) for 1 hour at 4° C. After washing, bound protein is detected using an anti human IgG/FITC conjugated antibody (Dako). Cells were analysed on a Becton Dickinson FACS machine. FACS results show that there is at least a 1 log shift in fluorescence activity in those 5T4 positive cells treated with the ScFv-IgG construct compared to the negative control construct consisting of the ScFv protein alone. A9 neo FACS shows that there is no non-specific binding of the ScFv component of the fusion protein.

FACS analysis of ScFv-IgE is carried out similar to above except that anti-human IgE-FITC (Dako) is used to detect binding of the fusion protein. The B7/EGF fision protein is analysed for binding using FACS and HC11-erb-B2 positive cells (Hynes et al 1990). CTLA4-Ig (Ancell, USA) is used to analyze the bioactivity of the B7 component of the bound fusion protein. Anti-mouse IgG-FITC is used to show CTLA-4 binding.

Example 16

Assembly and Cloning of an ScFv Specific for IL-5

Figure 7:
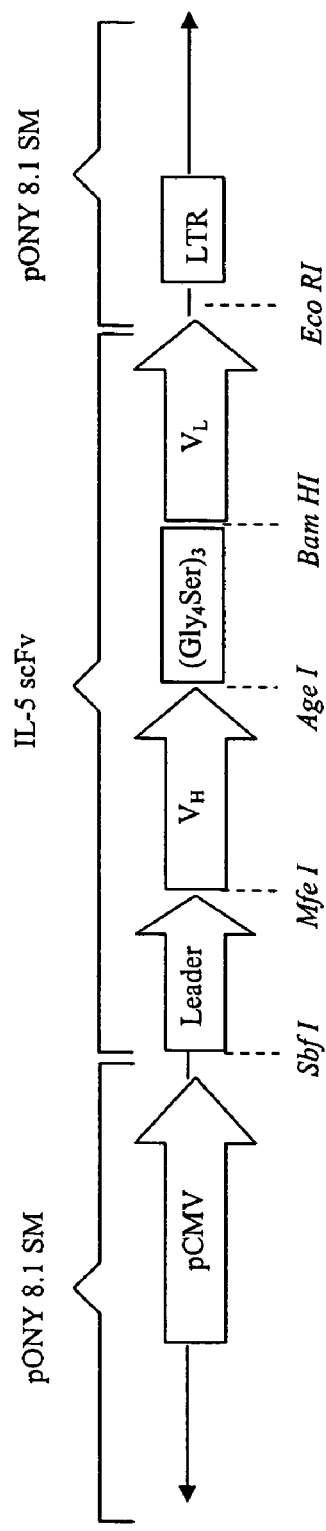
FIG. 7 shows Leader-IL-5 scFv in pONY 8.1SM.

The anti-IL-5 scFv is assembled by RT-PCR using material prepared from a hybridoma line such as the one expressing the humanized Mab to IL-5, SB 240563 (Leckie, M J, Am. J. Respir. Crit. Care Med. 159, A624 1999). Techniques are similar to those described by Clackson et al (Genetically engineered monoclonal antibodies. Br J Rheumatol. 1991;30 Suppl 2:36-9). Briefly, total RNA is prepared from SB 240563 cells. First strand synthesis is performed using MMLV reverse transcriptase using oligo dT primer. Template cDNAs are amplified by PCR with VH and VL gene specific primer pairs that include restriction enzyme sites to allow cloning into pKLink, a pBluescript II SK (pBSII) plasmid that contains a flexible linker sequence, $(Gly_4Ser)_3$ (FIG. 5) This forms the single chain antibody cDNA (FIG. 6). A double stranded oligonucleotide encoding a translation initiation, Kozak sequence and the human Ig kappa light chain signal peptide for secretion, is then cloned upstream of the scFv. The whole construct is then excised with Sbf I and Eco RI and cloned into pONY 8.1SM (see WO 01/36486) (FIG. 7).

Cloning of scFv specific for IL-5 into pAdApt

The L-scFv cloned into pBSII is digested with Xba I, filled in to give a blunt end and then digested with Eco RI. The pAdApt vector is digested with Hind III filled in to give a blunt end and then digested Eco RI. The two molecules are then ligated to give a recombinant transfer vector.

Production of recombinant adenovirus expressing the scFv fusion construct

To produce recombinant adenovirus expressing the scFv fusion construct, PerC6 cells are transfected with equimolar amounts of the recombinant transfer vector containing the fusion construct and an adenovirus Genome vector (AdEasy from Quantum Apligene, Harefield UK). Recombinant virus is then harvested as described in the Crucell protocol. The recombinant virus can be used as a pharmaceutical composition for the prevention and/or treatment of asthma.

Example 17

Assembly and Cloning of an ScFv Specific for the Envelope Protein gp120 of HIV

The anti-HIV scFv is assembled by RT-PCR using material prepared from a hybridoma line expressing a mAb to the envelope protein gp120 of HIV, such as mAb 110.3 (Conelly et al, Virology 295: 554-557, 1994.). Alternatively guided selection is used to make a humanized antibody (see Beiboer S H et al, *J Mol Biol*, 2000; 296:833-849) from which the scFv is then derived. Techniques are similar to that described by Clackson et al (Genetically engineered monoclonal antibodies. Br J Rheumatol. 1991; 30 Suppl 2:36-9). Briefly, Total RNA is prepared from the hybridoma cells. First strand synthesis is performed using MMLV reverse transcriptase using oligo dT primer. Template cDNAs are amplified by PCR with VH and VL gene specific primer pairs that include restriction enzyme sites, such as those shown below, to allow cloning into pKLink, a pBluescript II SK (PBSII) plasmid that contains a flexible linker sequence, $(Gly_4Ser)_3$ (SEQ ID NO:13) (FIG. 5) This forms the single chain antibody cDNA (FIG. 21). A double stranded oligonucleotide encoding a translation initiation, Kozak sequence and the human Ig kappa light chain signal peptide for secretion, is then cloned upstream of the scFv.

Figure 8:
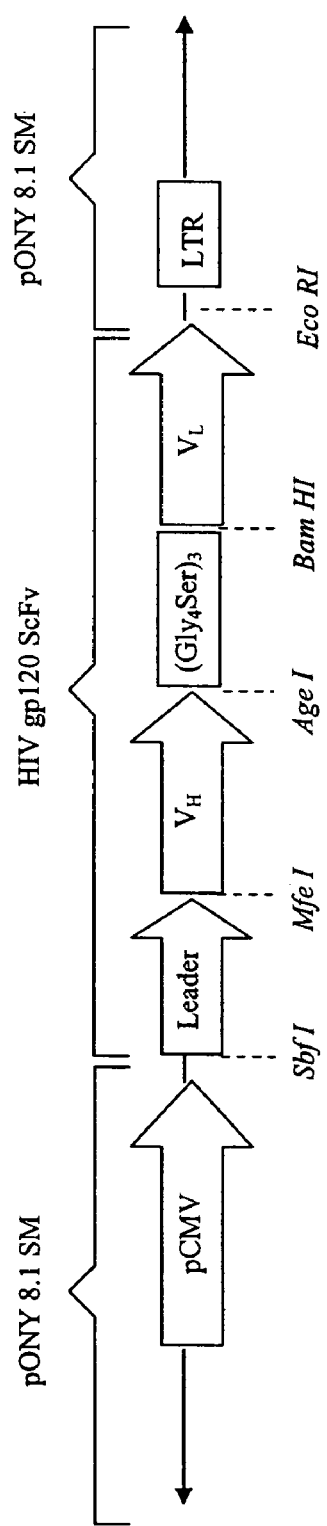
FIG. 8 shows Leader-HIV gp120 scFv in pONY 8.1SM.

The whole construct is then excised with Sbf I and Eco RI and cloned into pONY 8.1SM (FIG. 8).

Cloning of scFv specific for the envelope protein gp120 of HIV

The L-scFv cloned into pBSII is digested with Xba I, filled in to give a blunt end and then digested with Eco RI. The pAdApt vector is digested with Hind III filled in to give a blunt end and then digested Eco RI. The two molecules are then ligated to give a recombinant transfer vector.

To produce recombinant adenovirus expressing the scFv fusion constructs, PerC6 cells are transfected with equimolar amounts of the recombinant transfer vector containing the fusion construct and an adenovirus Genome vector (AdEasy from Quantum Apligene, Harefield UK). Recombinant virus is then harvested as described in the Crucell protocol.

The recombinant virus can be used to enhance a patient's anti-HIV response by providing an in vivo factory for a gp120-specific antibody.

Example 18

Anti-TNF Antibodies and Rheumatoid Arthritis

This example explains assembly and cloning of scFv specific for human TNF. The recombinant human anti-TNF antibodies are isolated as described in Hoogenboom et al. (Human antibodies that bind human TNF alpha. U.S. Pat. No. 6,090,382). Below is described an example based on the antibody D2E7. Template cDNAs are amplified by PCR with VH and VL gene specific primer pairs that include restriction enzyme sites, such as those shown below, to allow cloning into pKLink, a pBluescript II SK (pBSII) plasmid that contains a flexible linker sequence, $(Gly_4Ser)_3$ (SEQ ID NO:13) (FIG. 5). This forms the single chain antibody cDNA (FIG. 6). A double stranded oligonucleotide encoding a translation initiation, Kozak sequence and the human Ig kappa light chain signal peptide for secretion, similar to that described in the construction of the scFv to 5T4 (see WO 01/36486), is then cloned upstream of the scFv (FIG. 6).

Figure 9:
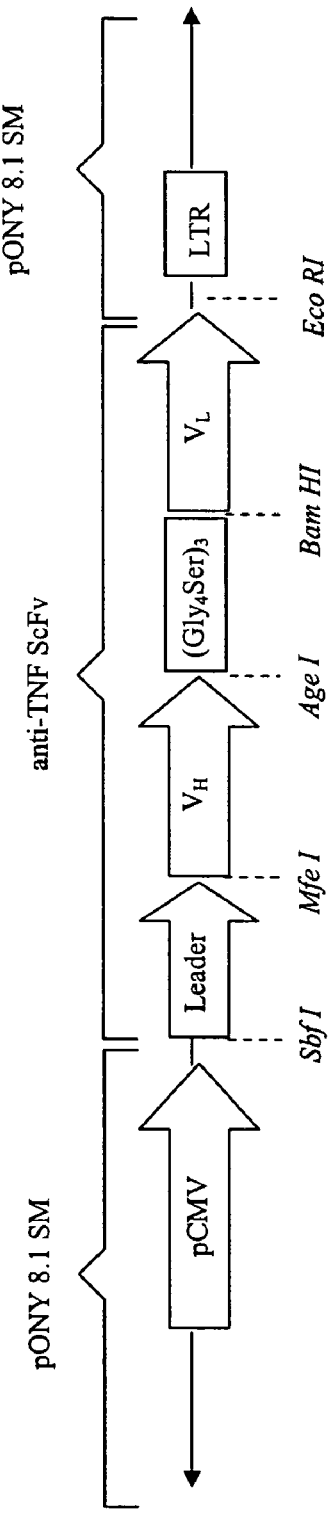
FIG. 9 shows Leader-anti-TNF alpha scFv in pONY 8.1SM.

The whole construct can then be excised with Sbf I and Eco RI and cloned into a lentivector such as pONY 8.1SM (FIG. 9). In this example the VH is amplified with additional Spe I and Mfe I restriction sites at the 5' end and an additional Age I site at the 3' end. The Spe I and Age I sites are used to clone into pKlink. The VL is amplified with an additional Bam HI restriction site at the 5' end and an additional Eco RI site at the 3' end, which are used for cloning into pKlink. The leader signal peptide is synthesized as two complementary oligonucleotides, that are annealed to give restriction enzyme overhangs and then cloned as a double stranded oligonucleotide between the Spe I and Mfe I sites at the 5' end of the scFv cDNA. The Kozak sequence including the ATG start codon (underlined) is in bold and italics.

The VH and VL sequences are shown as SEQ ID NO: 8 and 9, respectively. The recombinant virus can be used as a pharmaceutical composition for the prevention and/or treatment of arthritis.

Example 19

Assembly and Cloning of scFv Specific for Human VEGF for Treatment of Retina Disease The recombinant human anti-VEGF antibodies are isolated as described in Vitaliti et al. Cancer Res 2000 Aug 15; 60(16):4311-4. (Inhibition of tumor angiogenesis by a single-chain antibody directed against vascular endothelial growth factor). Below is described an example based on the antibody sequence available in the GenBank database (submitted by Yan et al; accession no. AB014341). Template cDNAs are amplified by PCR with VH and VL gene specific primer pairs that include restriction enzyme sites, such as those shown below, to allow cloning into pKLink, a pBluescript II SK (pBSII) plasmid that contains a flexible linker sequence, $(Gly_4Ser)_3$ (SEQ ID NO:13) (FIG. 5). This forms the single chain antibody cDNA (FIG. 6). A double stranded oligonucleotide encoding a translation initiation, Kozak sequence and the human Ig kappa light chain signal peptide for secretion, similar to that described in the construction of the scFv to 5T4 (see WO 01/36486), is then cloned upstream of the scFv (FIG. 6).

Figure 10:
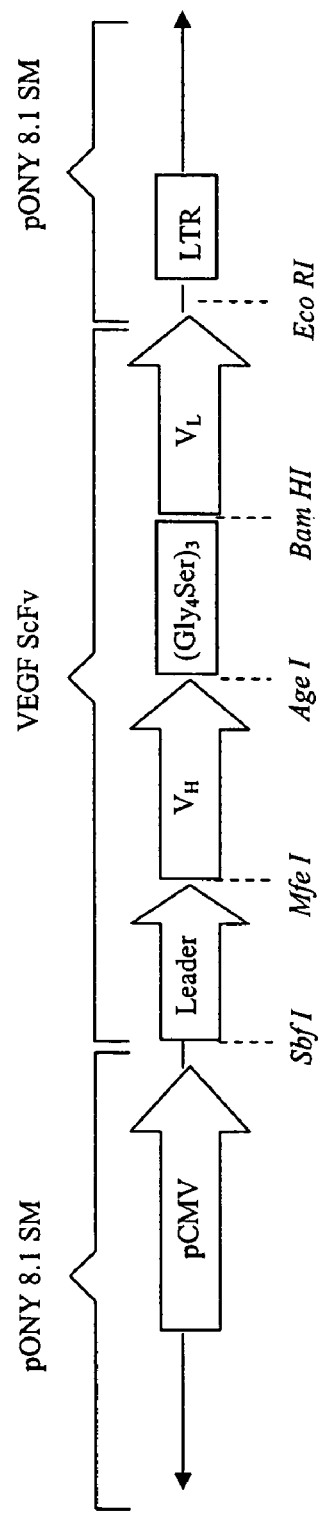
FIG. 10 shows Leader-VEGF scFv in pONY 8.1SM.

The whole construct is then be excised with Sbf I and Eco RI and cloned into a lentivector such as pONY 8.1SM (FIG. 10). In this example the VH is amplified with additional Spe I and Mfe I restriction sites at the 5' end and an additional Age I site at the 3' end. The Spe I and Age I sites are used to clone into pKlink. The VL is amplified with an additional Bam HI restriction site at the 5' end and an additional Eco RI site at the 3' end, which are used for cloning into pKlink.

The leader signal peptide is synthesized as two complementary oligonucleotides, that are annealed to give restriction enzyme overhangs and then cloned as a double stranded oligonucleotide between the Spe I and Mfe I sites at the 5' end of the scFv cDNA. The Kozak sequence including the ATG start codon (underlined) is in bold and italics. The ScFv sequence is shown as SEQ ID NO: 10.

The recombinant virus can be used as a pharmaceutical composition for the prevention and/or treatment of arthritis.

Example 20

Gene Transfer of scFv Proteins In Vivo

The aim of this study was to verify the expression of scFv following intratumor administration of a viral vector encoding scFv that has been tagged with myc and His polypeptides.

Experimental Design

An adenoviral vector expressing murine B7.1 fused to scFvmycHis (AdB7-scFv) was used to demonstrate the intra-tumoural delivery of genes that encode for scFv proteins specific to 5T4. A control adenoviral vector expressing the lac z gene (Adlac z) was also used. Both vectors used were of the human Ad5 serotype that lacks the genes encoding for E1 and E3.

CT26 cells expressing h5T4 (CT26-h5T4) were washed twice in PBS and $5\times10^5$ cells were injected sc into both flanks of a female Balb/c mouse. Each tumor was established to an average diameter of 5 mm and received 3 daily injections of $4\times10^8$ pfu Adenovirus in 50 µl. 48 hours after the final injection tumors were excised and snap frozen and 100 8 µm sections were cut prior to staining for murine B7.1 or c-myc proteins.

Results

There was no positive staining for c-myc or B7.1 in sections adjacent to those that were positive for lac z (FIG. 11). This confirms the specificity of staining by the anti-bodies used and also verifies that B7.1 positive staining seen is due to gene transfer of the scFv fusion protein and not the presence of adenovirus.

Gene transfer of B7-scFv was verified on adjacent sections that stained positive for B7.1 as well as for the c-myc tag (FIG. 12). Specificity of staining was verified by the absence of positive cells in those sections that were incubated in the secondary antibody alone.

Example 21

Lentiviral Vector Encoding a Cancer Immunotherapeutic

This example describes a procedure for producing a lentiviral vector that was delivered to target cells in Example 22. The lentiviral vector was produced by transfecting three plasmids into producer cells. One plasmid, which is referred to as SMART2 LscFvB7.1 5'cPPT, encoded the lentiviral EIAV genome, lacked sequences encoding env and gag/pol, and included a nucleotide sequence that encoded a conjugate comprising an antibody fragment that binds to 5T4 and a B7.1 effector protein that induces an immune response. The nucleotide sequence encoding the conjugate is referred to as LscFvB7.1, and the SMART2LscFvB7.1 5'cPPT plasmid was constructed by inserting the LscFvB7.1 nucleotide sequence isolated from a bluescript plasmid into the EIAV genome plasmid SMART25'cPPT, as described below.

The plasmid pBSIILscFvB7.1 was digested with Xba I to release a DNA fragment containing the sequence for LscFvB7.1. pBSIILscFvB7.1 was previously constructed by inserting the LscFvB7.1 sequence into the Spe I and Xba I sites of a modified pBSII plasmid (pBS/B7Link) described in more detail by Myers et al., *Cancer Gene Therapy* 9: 884-896 (2002). pBSII is manufactured by Stratagene. The overhanging sequences were filled using the klenow fragment polymerase and appropriate nucleotides to produce a blunt ended fragment. A subsequent digest with Hind III produced a Hind III 5' overhang and blunt ended 3' fragment of LscFvB7.1 (HIII- LscFvB7.1 -bl).

The ampicillin resistant EIAV genome plasmid, SMART25'cPPT, was digested with Xho I, filled with klenow fragment polymerase, and then digested with Hind III to produce bl-SMART25'cPPT-HIII. The resultant ~7Kb bl-SMART25'cPPT-HIII fragment was gel purified and ligated with the 1.6Kb gel purified fragment of HIII-LscFvB7.1-b. Stable II competent *E. coli* cells (GIBCO Cat #10268-019) were transformed with the ligation product, and individual colonies were selected from ampicillin plates following incubation as described by the manufacturer of the competent cell line. Clones of SMART25'cPPT containing the LscFvB7.1 insert were identified (following mini-prep and appropriate diagnostic digests of the isolated DNA) and endotoxin free DNA was prepared using a Quiagen kit. FIG. 13 shows the nucleotide sequence of the resulting SMART2 LscFvB7.1 5'cPPT plasmid and the nucleotide sequence of the scFvB7.1 insert subcloned from the bluescript plasmid is depicted as underlined text.

pSMART25'cPPT, which has the nucleotide sequence set forth in FIG. 14, was derived from pSMART1G, which already had the cPPT located to the 5' of the CMV eGFP cassette by digestion with SphI and BstEII, flushing the protruding termini with T4 DNA polymerase treatment in the presence of dNTP's, followed by religation. pSMART1G was derived from pONY8G 5'cPPT POS delCTS by routine cloning steps. The nucleotide sequence of the post-transcriptional regulatory element of woodchuck hepatitis virus (WPRE) was inserted into the filled-in SapI site (cuts after nucleotide 7897 of EIAV Accession No. U01866) and the LTR was converted to a self-inactivating (SIN) configuration by deleting nucleotides 7996 to 8170. The sequences representing the WPRE are nucleotides 4835 to 5428 of SMART2G (FIG. 14), thus the WPRE had flanking sequences that extend 30 nucleotides in length from the 5' end and 55 nucleotides in length from the 3' end. The WPRE represents nucleotides 1091 to 1684 of Woodchuck hepatitis B virus (Accession No. J04514). The SIN LTR was deleted with respect to all transcription factor binding sites and the TATA-box. The EIAV sequence resumes at the first nucleotide of the Muni recognition sequence at nucleotide 8171, with respect to Accession No. U01866.

The SMART2 LscFvB7.1 5'cPPT genome plasmid was cotransfected with plasmids encoding VSV-G envelope and gag/pol, which are disclosed in U.S. Pat. No. 6,312,683, to generate the EIAV recombinant virus SMT2scFvB7.15'cPPT.

Example 22

Delivery of a Single Chain Fv Fragment (scFv) Specific to a Tumor

Associated antigen (TAA) for Directing Cellular Immune Responses to Tumors In Vivo The aim of this study was to direct an immune response specifically to tumors positive for the human TAA, 5T4.

Chimeric proteins based on a scFv specific for the oncofetal glycoprotein, 5T4 were constructed. This TAA is expressed by a wide variety of carcinomas and in a number of these has been shown to be associated with poor prognosis. In order to direct an immune response specifically to tumors positive for human 5T4, fusion proteins of the scFv linked to the extracellular domain of murine B7.1 (scFv-B7.1) have been constructed.

Delivery vectors based on equine infectious anemia virus (EIAV) and adenovirus have been engineered for the gene transfer of scFv proteins that are specific to 5T4.

Transduction of tumor cell lines with these recombinant viral vectors has shown that genetic delivery of the constructs in vitro leads to successful production of scFvB7.1 fusion proteins that are secreted into the cell media. These proteins are able to bind to 5T4 expressed at the surface of transduced cells.

Figure 15:
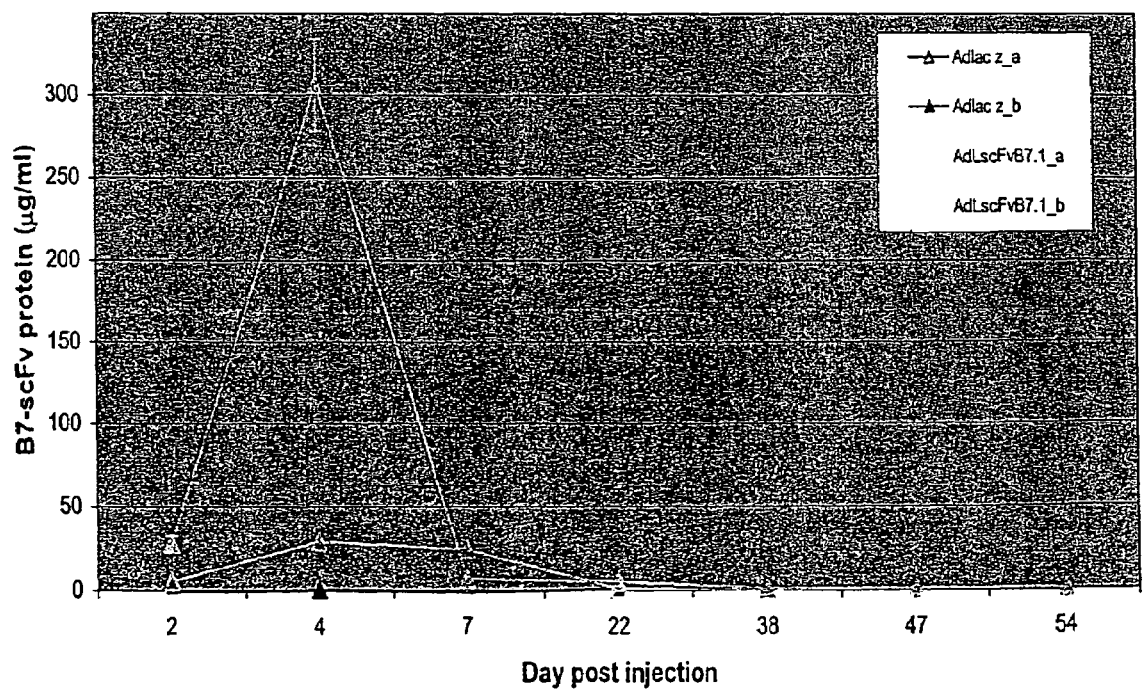
FIG. 15 shows levels of scFvB7.1 detected in the sera of Balb/c mice following administration of 1.5×10$^9$ IU AdscFvB7.1.

Following systemic administration of AdscFv-B7.1, scFv-B7.1 protein is present in 5T4 positive tumors established sub-cutaneously in Balb/c mice (FIG. 15).

On day 4, the concentration of scFv in the sera of mice injected with AdscFvB7.1 is much greater (up to 437 fold) than that seen in mice injected with EIAV expressing scFvB7.1 (SMTscFvB7.1). This is determined after taking into account non-specific antibodies in the sera of mice injected with the equivalent constructs that express LacZ (Table 1).

Table 1 illustrates the sera concentrations of scFv-B7.1 (µg/ml) following ion of adenovirus or EIAV that expresses scFv-B7.1 specific to human 5T4.

TABLE 1

| Day post injection | Adlacz a | Adlacz b | AdscFvB 7a | AdscFvB 7b | SMTIacz a | SMTIacz b | SMTscFvB 7a | SMTscFv b |
|---|---|---|---|---|---|---|---|---|
| 2 | 0.00 | 0.00 | 5.30 | 27.66 | 0.34 | 0.34 | 0.45 | 0.86 |
| 4 | 0.00 | 0.32 | 29.03 | 306.29 | 0.70 | 0.67 | 1.40 | 1.35 |
| 7 | 0.00 | 0.00 | 24.10 | 6.62 | 0.72 | 0.66 | 1.93 | 1.21 |
| 22 | 0.30 | 0.28 | 0.54 | 4.98 | 0.36 | 0.27 | 2.01 | 1.60 |
| 38 | 0.36 | 0.64 | Nd | 0.83 | 0.63 | 0.55 | 1.93 | 1.73 |
| 47 | 0.28 | 0.60 | 0.96 | 0.73 | 1.04 | 0.70 | 1.95 | 2.77 |
| 54 | 0.18 | 0.46 | 0.45 | 0.60 | 1.00 | 0.85 | 1.32 | 3.18 |

By day 22 this level drops almost 60 fold and continues to wane very closely to background levels by day 38. Therefore, by day 38 the net serum concentration in mice administered with SMTscFv is approximately 3 fold higher than that seen in the AdscFvB7.1 group. The levels of scFvB7.1 in the sera of mice injected with SMTscFvB7.1 does not fall below 1 µg/ml before day 54 whereas in mice injected with AdscFvB7.1 the concentration of scFvB7.1 is well below 1 µg/ml on day 38.

Although serum protein levels achieved with $1.5 \times 10^9$ IU of AdscFv-B7.1 results in 16 µg/ml of protein 4 days after iv injection, 18 days later this drops to 2 µg/ml.

Figure 16:
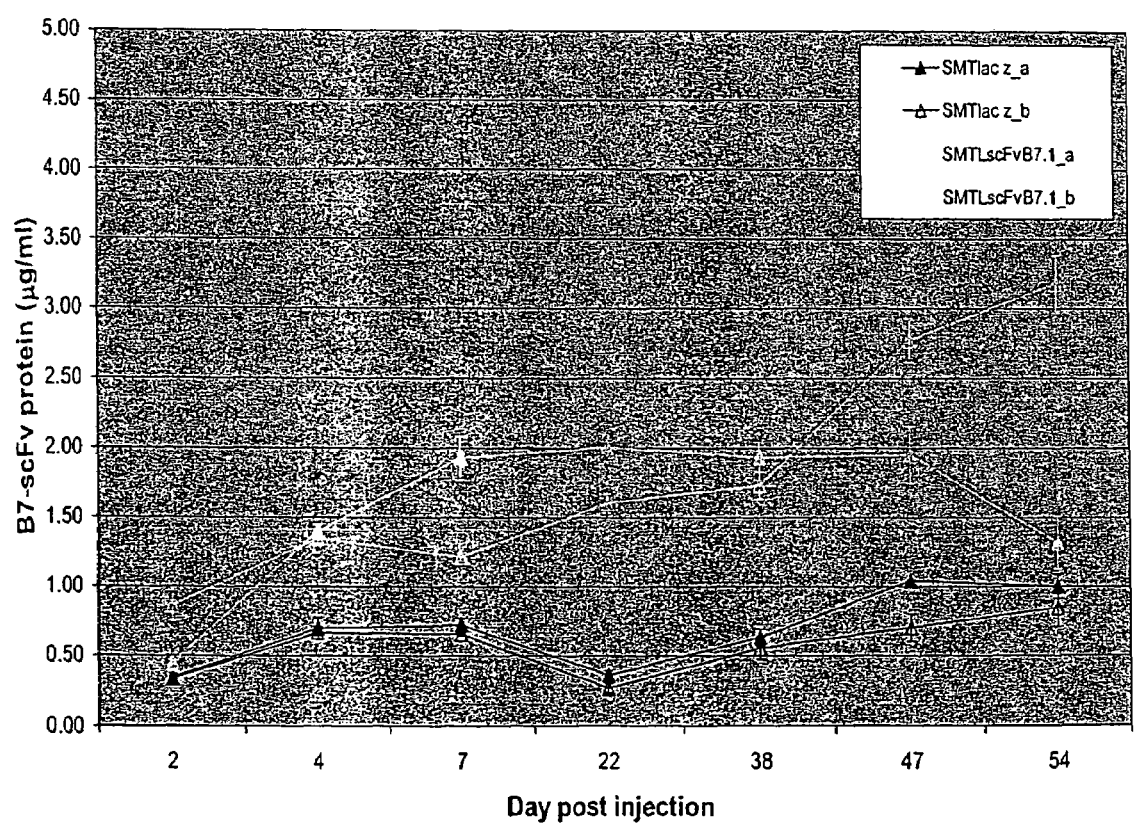
FIG. 16 depicts levels of scFvB7.1 detected in the sera of Balb/c mice following administration of 2×10$^7$ TU EIAV expressing scFvB7.1 (SMTscFvB7.1).

Conversely, serum levels of protein achieved with $2 \times 10^7$ TU of EIAV 4 days after iv administration is less (0.6 µg/ml) but continues to increase to 1.4 and 1.2 µg/ml by days 22 and 29 respectively. By day 47, scFv-B7.1 delivered by EIAV can still be detected (~1.3 µg/ml) whilst protein delivered by Adenovirus is ~0.4 µg/ml (FIG. 16).

This example demonstrates the utility of EIAV vectors for the genetic delivery of antibodies for cancer therapy.

Reference is made in this application to the following applications: U.S. patent application Ser. No. 09/532,909 filed 22 Mar. 2000 claiming priority from PCT/GB98/02867 and GB 0005846.1; U.S. patent application Ser. No. 09/533,276 filed 22 Mar. 2000 claiming priority from PCT/GB98/02867 and GB 0005841.2; U.S. patent application Ser. No. 09/533,295 filed 22 Mar. 2000 claiming priority from PCT/GB98/02867 and GB 0005844.6; PCT No. PCT/GB98/02867 filed 23rd Sep. 1998 claiming priority of GB 9720465.5 designating inter alia the U.S.; PCT No. PCT/GB98/02885 filed 23rd Sep. 1998 claiming priority of GB 9720216.2 designating inter alia the U.S.; U.S. Ser. No. 09/238,356 filed 27th Jan. 1999 claiming priority of GB 9811037.2 and GB 9727135.7; PCT No. PCT/GB99/00325 filed 17th Feb. 1999 claiming priority of GB 9803351.7 designating inter alia the U.S.; PCT No. PCT/GB99/00672 filed 5th May 1999 claiming priority of GB 9902081.0, GB 9818103.5 and GB 9804841.6 designating inter alia the U.S.; PCT No. PCT/GB99/00764 filed 5th May 1999 claiming priority of GB 9902081.0, GB 9818103.5 and GB 9804841.6 designating inter alia the U.S.; U.S. Ser. No. 60/093,149 filed 17th Jul. 1998 claiming priority of GB 9811152.9; PCT No. PCT/GB99/03866 filed 19th Nov. 1999 claiming priority of GB 9825524.3 designating inter alia the U.S.; PCT No. PCT/GB00/00520 filed 15th Feb. 2000 claiming priority of GB 9903408.4 designating inter alia the U.S.; and PCT No. PCT/GB99/03181 filed 22nd Sep. 1999 claiming priority of GB 9903538.8, GB 9901906.9 and PCT/GB98/02885 designating inter alia the US.

Each of the aforementioned patent and patent application cited herein, and each document cited in each patent and patent application, either in the text thereof or during the prosecution thereof, and each document referenced or cited in each patent and patent application, is hereby incorporated herein by reference. Likewise, each document cited in this text and each document referenced or cited in herein-cited documents is hereby incorporated herein by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method delivering an antibody to a target cell, said method comprising directly administering to the target cell a lentiviral vector comprising a nucleotide sequence of interest (NOI) encoding an antibody, wherein the antibody comprises the amino acid sequence encoded by the nucleic acid sequence of SEQ ID NO: 2 and wherein the antibody is expressed in the target cell.

2. The method of claim 1, wherein the expression of the antibody is sustained for 20 days or more.

3. The method of claim 1, wherein the expression of the antibody is sustained for 30 days or more.

4. The method of claim 1, wherein the expression of the antibody is sustained for 40 days or more.

5. The method of claim 1, wherein the expression of the antibody is sustained for 50 days or more.

6. The method of claim 1, wherein the expression of the antibody is sustained for 60 days or more.

7. The method of claim 1, wherein the lentiviral vector is an EIAV vector.

* * * * *